(12) United States Patent
Rees et al.

(10) Patent No.: US 7,589,123 B2
(45) Date of Patent: Sep. 15, 2009

(54) CHEMICAL COMPOUNDS

(75) Inventors: Daryl David Rees, Godmanchester (GB); Phillip James Gunning, Godmanchester (GB); Antonia Orsi, Godmanchester (GB); Patrick A. Howson, Godmanchester (GB); Paul Barraclough, Maidstone (GB); Noelle Callizot, Godmanchester (GB)

(73) Assignee: Phytopharm PLC, Godmanchester (GB)

( * ) Notice: Subject to any disclaimer, the term of this patent is extended or adjusted under 35 U.S.C. 154(b) by 0 days.

(21) Appl. No.: 11/773,952

(22) Filed: Jul. 5, 2007

(65) Prior Publication Data

US 2008/0045591 A1 Feb. 21, 2008

(30) Foreign Application Priority Data

Jul. 6, 2006 (GB) ................................. 0613518.0

(51) Int. Cl.
*A61K 31/12* (2006.01)
*C07C 49/00* (2006.01)
*C07C 69/78* (2006.01)

(52) U.S. Cl. .................. 514/533; 514/590; 514/678; 514/690; 568/306; 568/308; 568/328; 568/329; 560/55

(58) Field of Classification Search ................ 514/533, 514/590, 678, 690
See application file for complete search history.

(56) References Cited

U.S. PATENT DOCUMENTS

| | | | | |
|---|---|---|---|---|
| 4,649,157 | A | * | 3/1987 | Partis et al. ................. 514/545 |
| 4,810,716 | A | | 3/1989 | Connor et al. |
| 6,518,315 | B1 | * | 2/2003 | Roufogalis et al. .......... 514/678 |
| 2006/0148830 | A1 | * | 7/2006 | Terakado et al. ......... 514/264.1 |

FOREIGN PATENT DOCUMENTS

| | | |
|---|---|---|
| EP | 0402469 | 12/1990 |
| EP | 1553075 | 7/2005 |
| JP | 6340618 | 12/1994 |
| JP | 2003-306438 A | 10/2003 |
| WO | WO-94/19358 | 9/1994 |
| WO | WO-2004/031118 | 4/2004 |
| WO | WO-2004/037793 | 5/2004 |
| WO | WO 2004/089911 | 10/2004 |

OTHER PUBLICATIONS

Zhang et al. Mild Conversion of B-Diketones and B-ketoesters to Carboxylic Acids, Journal of Organic Chemistry, 2006, vol. 71, pp. 4516-4520.*
Inoue et al. Synthesis of 2-Alkyl-Substituted 1,3-Diketones via the 1,4-Addition of the Grigards Reagents to alpha, beta-Unsaturated Imidates. Bulletin of the Chemical Society of Japan, 1989, vol. 62, pp. 1601-1605.*

Beam et al. Cyclization at the Less Nucleophilic Center of a B-diketone Dicarbanion through a Dicarbonion-Benzene Intermediate. Journal of Organic Chemistry, 1970, vol. 35 (6), pp. 2083-2085.*

(Continued)

*Primary Examiner*—Sikarl A Witherspoon
(74) *Attorney, Agent, or Firm*—Marshall, Gerstein & Borun LLP

(57) ABSTRACT

Compounds of general formula I:

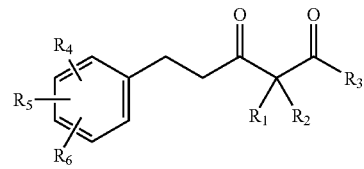

wherein:

$R_1$ and $R_2$ are, independently of each other, selected from hydrogen, optionally substituted $C_{1-10}$alkyl, optionally substituted —CO—($C_{1-10}$alkyl), optionally substituted $C_{3-10}$cycloalkyl, optionally substituted —CO—($C_{3-10}$cycloalkyl), optionally substituted $C_{2-10}$alkenyl, optionally substituted —CO—($C_{2-10}$alkenyl), optionally substituted aryl, and optionally substituted —CO-aryl, or $R_1$ and $R_2$ together represent an optionally substituted saturated or unsaturated $C_{1-10}$alkylidene group, or an optionally substituted saturated or unsaturated $C_{3-10}$cycloalkylidene group, or $R_1$ and $R_2$ together with the carbon atom to which they are attached represent an optionally substituted saturated or unsaturated organic ring containing 3, 4, 5, 6, 7 or 8 ring carbon atoms and optionally 1, 2 or 3 ring heteroatoms selected from O, N and S;

$R_3$, which may be the same as, or different from, either of $R_1$ and $R_2$, is selected from optionally substituted $C_{1-10}$alkyl, optionally substituted $C_{3-10}$cycloalkyl, optionally substituted $C_{2-10}$alkenyl, and optionally substituted aryl;

$R_4$, $R_5$ and $R_6$ are, independently of each other, selected from hydrogen, optionally substituted $C_{1-10}$alkyl, OH, optionally substituted $C_{1-10}$ alkoxy, halo, optionally substituted aryloxy, optionally substituted ($C_{1-10}$alkyl)-S(O)$_n$— where n=0, 1 or 2, optionally substituted aryl-S(O)$_n$— where n=0, 1 or 2, or $R_4$ is hydrogen and $R_5$ and $R_6$ together represent an optionally substituted saturated or unsaturated organic chain containing 1, 2, 3, 4, 5, 6 or 7 chain carbon atoms and optionally 1, 2 or 3 chain heteroatoms selected from O, N and S, provided that the chain is at least 3 atoms long;

with the proviso that, when $R_1$=$R_2$=hydrogen, then any optionally substituted $C_{1-10}$alkyl or optionally substituted $C_{2-10}$alkenyl for $R_3$ must have a branch point at one or more of the α and β positions counted from the carbonyl group (or tautomeric form thereof) to which $R_3$ is attached;

or a physiologically acceptable salt, complex or prodrug thereof;

are disclosed per se and for use in the treatment or prophylaxis of hypersensitivity, smooth muscle disorders, spasmodic conditions, allergic conditions, inflammatory conditions and/or pain.

37 Claims, 1 Drawing Sheet

OTHER PUBLICATIONS

Berge et al., "Pharmaceutical salts," Journal of Pharmaceutical Sciences, 66:1-19 (1977).

Borsche et al., "366. Untersuchungen über die bestandteile der kawawurzel, XIV. mitteil. 1): über cinnamoyl-essigester," European Journal of Inorganic Chemistry, 66:1792-1801 (1933).

International Search Report and Written Opinion of the International Searching Authority for corresponding international application No. PCT/GB2007/002527, dated Nov. 6, 2008.

Kawano et al., "Preparation of pyrazole-4-alkanoic acid derivatives as cyclooxygenase and 5-lipoxygenase inhibitors," Chemical Abstracts Service, 140:391278 (2004).

Onoe et al., "Preparation of 4-(3-carboxy-2-hydroxypropyl)-2-azetidinone derivatives as intermediate for beta-lactam antibiotic carbapenem," Chemical Abstracts Service, 122:187262 (2003).

Pedersen et al., "Synthesis of naturally occurring curcuminoids and related compounds," Liebigs Ann. Chem., 1557-1569 (1985).

Venugopalan et al., "Metal chelates of 6-aryl-5-hexene-2,4-diones," J. Indian Chem. Soc., 78:472-473 (2001).

Wuryantoko et al., "The reduction ability of curcumin and its derivative (4-alkyl-curcumin) toward ferric ion assayed using an ortho-phenanthroline complex," Chemical Abstracts Service, 129:22910 (1997).

Combined Search and Examination Report from the UK Intellectual Property Office for corresponding British application No. GB0713117.0, dated Oct. 31, 2007.

Flynn et al., "Styrylpyrazoles, styrylisoxazoles, and styrylisothiazoles. Novel 5-lipoxygenase and cyclooxygenase inhibitors", J. Med. Chem., 34:518-525 (1991).

Hashimoto et al., "A new chromone from agarwood and pyrolysis products of chromone derivatives," Chem. Pharm. Bull., 33:5088-5091 (1985).

Invitation to Pay Additional Fees with Annex to Form PCT/ISA/206 for corresponding international application No. PCT/GB2007/002527, dated May 11, 2007.

Kaplan et al., "Reaction of sec- and tert-butyllithium with esters of benzoic, phenylacetic, hydrocinnamic, and cyclohexanecarboxylic acids," Zhurnal Obshchei Khimii, 33:2103-2106 (1963)—abstract only.

Kiuchi et al., "Inhibition of prostaglandin and leukotriene biosynthesis by gingerols and diarylheptanoids," Chem. Pharm. Bull. (Tokyo), 40:387-391 (1992).

Koo, "Synthesis in the chromone series. 5,8-Dimethoxy-2-substituted chromones and nitrogen analogs," J. Org. Chem., 26:2440-2442 (1961).

Lampe et al., "Coupling ability of both methyl groups in the quaternary base derived from 3,5-dimethylisoxazole. IV. Syntheses of diacylmethane," Bulletin de L'Academie Polonaise des Sciences, 11:49-53 (1963).

Mukhopadhyay et al., "Anti-inflammatory and irritant activities of curcumin analogues in rats," Agents Actions, 12:508-515 (1982).

Picker et al., "The chemical constituents of Australian Flindersia species. XXI. An examination of the bark and the leaves of *F. laevicarpa*," Aust. J. Chem., 29:2023-2036 (1976).

Standard Search Report from the European Patent Office for corresponding British application No. GB0613518, dated Jan. 3, 2007.

Surh, "Anti-tumor promoting potential of selected spice ingredients with antioxidative and anti-inflammatory activities: a short review," Food Chem. Toxicol., 40:1091-1097 (2002).

Van Baar et al., "Electron ionization mass spectrometry of curcumin analogs: an olefin metathesis reaction in the fragmentation of radical cations," J. Mass Spectrometry, 33:319-327 (1998).

Venkateswarlu et al., "Synthesis of 1,7-bis(4-hydroxypenyl)-4-hydroxy-1,3-heptadiene-5-one, an antiplatelet diarylheptanoid from Alpinia blepharocalyx K. schum," J. Asian Nat. Prod. Res., 2:111-120 (2000).

Weber et al., "Activation of NFkB is inhibited by curcumin and related enones," Bioorganic & Medicinal Chem., 14:2450-2461 (2006).

Xue et al., "Triphenylphosphine-catalyzed reaction of aldehydes and acetylenic ketones with 1,3-dicarbonyl moieties: synthesis of multicarbonyl compounds," Synlett., 19: 2990-2992 (2005).

* cited by examiner

CHEMICAL COMPOUNDS

FIELD OF THE INVENTION

The present invention relates to novel substituted dioxo-alkanes and dioxo-alkenes, as well as compositions and uses thereof.

BACKGROUND OF THE INVENTION

U.S. Pat. No. 4,649,157 (G D Searle & Co.), the disclosure of which is incorporated herein by reference, discloses certain generic definitions of phenyl-substituted dioxo-alkenes and substituted derivatives thereof which are said to possess activity as inhibitors of leukotriene biosynthesis. The compounds are proposed as agents against diseases and conditions associated with leukotrienes, such as allergic conditions, inflammatory conditions, certain skin disorders, hyperalgetic conditions and coronary vasoconstriction.

European Patent Application No. EP-A-0402469 (Terumo K. K.), the disclosure of which is incorporated herein by reference, discloses certain generic definitions of catechol compounds which are said to possess activity as inhibitors of 5-lipoxygenase in leukotriene biosynthesis. The compounds are proposed as agents against diseases and conditions associated with leukotrienes, such as nephritis, hepatitis, rheumatism and gastric ulcers, as well as allergic diseases such as asthma and rhinitis.

U.S. Pat. No. 4,810,716 (Warner-Lambert Company), the disclosure of which is incorporated herein by reference, discloses certain generic definitions of diarylalkanoids which are said to possess activity as lipoxygenase inhibitors. The compounds are proposed as agents for treating a disease such as allergy, asthma, arthritis, psoriasis, acne, inflammation, pain, ulcerogenic, or cardiovascular disorders.

U.S. Pat. No. 6,518,315 (The University of Sydney), the disclosure of which is incorporated herein by reference, discloses certain generic definitions of phenylalkanols which are said to provide for treatment or prophylaxis of pain by action on sensory nerves and/or through anti-inflammatory and/or through neurokinin inhibitory action (column 6, lines 31 to 36).

US Patent Application No. 2006/0148830 (Ono Pharmaceutical Co. Ltd), corresponding to WO-A-2004/031118, the disclosure of which is incorporated herein by reference, discloses certain generic and specific compound definitions which are said to engage in lysophosphatidic acid receptor bonding and antagonism and hence are useful for prevention and/or treatment of diseases such as urinary system disease, carcinoma-associated disease, proliferative disease, inflammation/immune system disease, disease by secretory dysfunction, brain related disease or chronic disease. Examples 34 and 35 of this prior art describe the preparation of 2-[4-[3-oxo-5-phenyl-2-(3,4,5-trimethoxybenzoyl)-pentyl]-phenoxy]-benzoic acid benzyl ester and 2-[4-[3-oxo-5-phenyl-2-(3,4,5-trimethoxybenzoyl)-pentyl]-phenoxy]-benzoic acid. However, the prior art provides no biological data for these compounds, and there is no suggestion that any compounds similar to them would have activity. The very highly extrapolated generic definitions, apparently constructed purely for the purpose of giving formalistic legal "unity" to the claims for patent purposes, cannot be said to hold out any credible promise of activity, or at least possibly outside a limited extrapolation from the four compounds that were biologically tested for EGD-2 antagonistic activity, namely the compounds of Examples 2(1), 2(4), 3(33) and 8(1), none of which is a dioxo compound of the type with which the present invention is concerned.

In addition, Surh, Y. J., *Food Chem. Toxicol.*, 1091-1097, 40(8), (2002); Kiuchi, F et al., *Chem. Pharm. Bull*, 387-391, 40 (1992); and Mukhopadhay, A. et al., *Agents and Actions*, 508-515, 12(4) (1982) report anti-inflammatory activity in an number of dioxo-alkanes. The disclosure of each of these publications is incorporated herein by reference.

Picker et al., *Aust. J. Chem.*, 29, 2023-2036 (1976), the disclosure of which is incorporated herein by reference, describes the preparation of 1-(2-hydroxy-3-methoxyphenyl)-5-phenylpentane-1,3-dione and 1-(2-hydroxyphenyl)-5-phenylpentane-1,3-dione.

Xue et al., Synlett, 19, 2990-2992 (2005), the disclosure of which is incorporated herein by reference, describes the preparation of 3-acetyl-4-(4-nitrobenzoyl)-7-phenyl-heptane-2,5-dione (compound 10).

Inoue et al., *Bull Chem. Soc. Japan*, 62, 1601-1605 (1989), the disclosure of which is incorporated herein by reference, describes the preparation of 1,9-diphenyl-4-(3-phenylpropyl)-3,5-nonanedione (compound 3b), 1,5-diphenyl-2-benzyl-1,3-pentanedione (compound 3c), 7-methyl-4-(1-methyl-3-phenylpropyl)-1,9-diphenyl-3,5-nonanedione (compound 3e) and 1,7,9-triphenyl-4-(1,3-diphenylpropyl)-3,5-nonanedione (compound 3g).

Koo, *Journal of Organic Chemistry*, 26, 2440-2442 (1961), the disclosure of which is incorporated herein by reference, describes the preparation of 1-(3,6-dimethoxy-2-hydroxyphenyl)-5-(3,4-dimethoxyphenyl)pentane-1,3-dione.

Beam et al., *Journal of Organic Chemistry*, 35, 2083-2085 (1970), the disclosure of which is incorporated herein by reference, describes the preparation of 5-(6-chlorophenyl)-1-phenylpentane-1,3-dione.

Venkateswarlu et al., *Journal of Asian Natural Products Research*, 2, 111-120 (2000), the disclosure of which is incorporated herein by reference, describes the preparation of 4-acetyl-1,7-bis-(4-methoxyphenyl)-hept-1-ene-3,5-dione.

Zhang et al., *Journal of Organic Chemistry*, 71, 4516-4520 (2006), the disclosure of which is incorporated herein by reference, describes the preparation of 1,5-diphenylpentane-1,3-dione.

Hashimoto et al., *Chemical and Pharmaceutical Bulletin*, 33, 5088-5091 (1985), the disclosure of which is incorporated herein by reference, describes the preparation of 1-(2-hydroxyphenyl)-5-(4-methoxyphenyl)pentane-1,3-dione.

Lampe and Smolinska, *Bulletin de L'Academie Polonaise des Sciences*, 11, 49-53 (1963), the disclosure of which is incorporated herein by reference, describes the preparation of 5-(4-hydroxy-3-methoxyphenyl)-1-phenylpentane-1,3-dione and 5-(4-hydroxy-3-ethoxyphenyl)-1-phenylpentane-1,3-dione.

Flynn et al., *Journal of Medicinal Chemistry*, 34, 518-525 (1991), the disclosure of which is incorporated herein by reference, describes the preparation of 5-(4-hydroxy-3-methoxyphenyl)-1-phenylpent-4-ene-1,3-dione.

The present invention is based on our surprising finding that certain known and novel compounds have an unexpected combination of activities which provide advantageous use in the treatment or prophylaxis of hypersensitivity, smooth muscle disorders, spasmodic conditions, allergic conditions, inflammatory conditions and/or pain such as, for example but not limited to, asthma, cough, pruritus, food intolerance, psoriasis, croup, irritable bowel syndrome, tinnitus, Meniere's disease, stress-induced ulceration or acetylsalicylic acid-induced ulceration, primary dysmenorrhea, pre-term labour, pre-term contractions, diarrhoea, gastrointestinal cramps, diverticular disease, achalasia, Hirschsprung's disease, gastro-oesophageal reflux disease, myotonic dystrophy, gallstone disease, constipation, post-surgical gastroparesis syndrome, paralytic ileus, post-operative ileus, diabetic gastroparesis, bowel paresis, intestinal pseudo-obstruction, peripheral arterial disease, Raynaud's syndrome, coronary artery spasm, angina, hypertension, hypotension, vascular paresis and other vascular disorders, bladder disorders, nausea, allergic rhinitis, allergic dermatitis, inflammation, inflammatory bowel disease, ileitis, pancreatitis, cholecystitis, non-allergic rhinitis, oesophagitis, osteoarthritis, rheumatoid arthritis, Huntington's disease, cerebral ischemia, acute inflammatory pain, neuropathic pain, visceral pain, dental pain and headaches.

The compounds may be useful as non-pharmaceuticals, for example in foods or beverages (for example in a functional food or beverage), providing health benefits (whether for diseased or non-diseased humans or animals), for example health benefits relating to hypersensitivity, smooth muscle conditions, spasmodic conditions, the immune-system and/or pain, such as, but not limited to, the maintenance of normal gut function, as a calmative for the gut, to maintain normal breathing, to ease motion sickness and vertigo, to soothe sore throats and coughs, to ease nausea and vomiting, as an aid to maintain normal digestion, to ease upset stomachs, to warm hands and feet, to aid normal menstruation, to maintain normal blood pressure, to normalise bowel movement, to maintain a healthy immune system, to aid in the recovery from colds and flu, as a decongestant, to soothe headaches, to relieve muscle soreness, to ease mild aches and pains, to provide relief from toothache, to provide relief from mouth ulcers, to maintain healthy joints, to help limit cellulite occurrence and as an aid to weight loss.

BRIEF DESCRIPTION OF THE INVENTION

According to a first aspect of the present invention, there is provided a compound of general formula I:

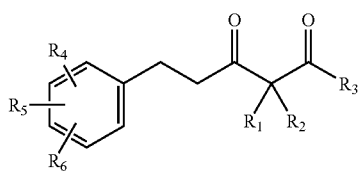

I wherein:
$R_1$ and $R_2$ are, independently of each other, selected from hydrogen, optionally substituted $C_{1-10}$ alkyl, optionally substituted —CO—($C_{1-10}$ alkyl), optionally substituted $C_{3-10}$ cycloalkyl, optionally substituted —CO—($C_{3-10}$ cycloalkyl), optionally substituted $C_{2-10}$ alkenyl, optionally substituted —CO—($C_{2-10}$ alkenyl), optionally substituted aryl, and optionally substituted —CO-aryl, or $R_1$ and $R_2$ together represent an optionally substituted saturated or unsaturated $C_{1-10}$ alkylidene group, or an optionally substituted saturated or unsaturated $C_{3-10}$ cycloalkylidene group, or $R_1$ and $R_2$ together with the carbon atom to which they are attached represent an optionally substituted saturated or unsaturated organic ring containing 3, 4, 5, 6, 7 or 8 ring carbon atoms and optionally 1, 2 or 3 ring heteroatoms selected from O, N and S;
$R_3$, which may be the same as, or different from, either of $R_1$ and $R_2$, is selected from optionally substituted $C_{1-10}$ alkyl, optionally substituted $C_{3-10}$ cycloalkyl, optionally substituted $C_{2-10}$ alkenyl, and optionally substituted aryl;
$R_4$, $R_5$ and $R_6$ are, independently of each other, selected from hydrogen, optionally substituted $C_{1-10}$ alkyl, OH, optionally substituted $C_{1-10}$ alkoxy, halo, optionally substituted aryloxy, optionally substituted ($C_{1-10}$ alkyl)-S(O)$_n$— where n=0, 1 or 2, optionally substituted aryl-S(O)$_n$— where n=0, 1 or 2, or $R_4$ and $R_5$ together represent an optionally substituted saturated or unsaturated organic chain containing 1, 2, 3, 4, 5, 6 or 7 chain carbon atoms and optionally 1, 2 or 3 chain heteroatoms selected from O, N and S, provided that the chain is at least 3 atoms long;
with the proviso that, when $R_1$=$R_2$=hydrogen, then any optionally substituted $C_{1-10}$ alkyl or optionally substituted $C_{2-10}$ alkenyl for $R_3$ must have a branch point at one or more of the α and β positions counted from the carbonyl group (or tautomeric form thereof) to which $R_3$ is attached;
or a physiologically acceptable salt, complex or prodrug thereof;
for use as a medicament, or when used as a medicament, or when presented and packaged as a medicament, or for use in a foodstuff or beverage (for example in a functional food or beverage), or when used in a foodstuff or beverage (for example in a functional food or beverage), or for use as a food supplement or beverage supplement, or when used as a food supplement or beverage supplement, or when presented and packaged as a food supplement or beverage supplement, or as a composition for any other use in treatment of a human or non-human animal.

Although the structure shown in Formula I indicates one particular tautomeric (keto) form, it will be understood that this representation is for convenience only and that the scope of the present invention includes equally all tautomeric (keto and enol) forms for the compounds. This applies also to the compounds of general formulae Ia II, Ia and IV mentioned below.

If it is to be held by any Patent Office or Court that WO-A-2004/031118, referred to above, discloses or renders obvious any one or more of the uses stated herein for any one or more particular compounds according to the present invention, then we reserve the right to exclude such use(s) of such compound(s) from the scope of protection of this application and/or its resulting patents.

For example, we reserve the right to exclude from the present invention the use of the compounds 2-[4-[3-oxo-5-phenyl-2-(3,4,5-trimethoxybenzoyl)-pentyl]-phenoxy]-benzoic acid benzyl ester and 2-[4-[3-oxo-5-phenyl-2-(3,4,5-trimethoxybenzoyl)-pentyl]-phenoxy]-benzoic acid. The term "the use of the compounds" includes all the use-related definitions of the compounds as set out above in the first aspect of the present invention.

Alternatively, for example, we reserve the right to exclude from the present invention the use of all compounds of Formula I in which one of $R_1$ and $R_2$ is CH$_2$-Ph-O-Ph-COOH, the other of $R_1$ and $R_2$ is hydrogen, and $R_4$=$R_5$=$R_6$=hydrogen, and any salt, complex or prodrug (e.g. ester) thereof (in which Ph represents a phenyl group).

Alternatively, for example, we reserve the right to exclude from the present invention the use of all compounds of Formula I in which one, but not both, of $R_1$ and $R_2$ is CH$_2$-Ph-O-Ph-COOH and any salt, complex or prodrug (e.g. ester) thereof.

Alternatively, for example, we reserve the right to exclude from the present invention the use of all compounds of Formula I in which both of $R_1$ and $R_2$ are CH$_2$-Ph-O-Ph-COOH and any salt, complex or prodrug (e.g. ester) thereof.

Alternatively, for example, we reserve the right to exclude from the present invention the use of all compounds of Formula I in which one, but not both, of $R_1$ and $R_2$ is optionally substituted $CH_2$-Ph-O-Ph-COOH and any salt, complex or prodrug (e.g. ester) thereof.

Alternatively, for example, we reserve the right to exclude from the present invention the use of all compounds of Formula I in which both of $R_1$ and $R_2$ are, independently of each other, optionally substituted $CH_2$-Ph-O-Ph-COOH and any salt, complex or prodrug (e.g. ester) thereof.

Alternatively, for example, we reserve the right to exclude from the present invention any of the uses of specific groups of compounds just mentioned, but only to the extent that in those excluded compounds $R_3$ is an aryl group, such as optionally substituted phenyl.

Alternatively, for example, we reserve the right to exclude from the present invention the use of all compounds of Formula I in which one, but not both, of $R_1$ and $R_2$ is within the definition of the moiety -Q-D-L-(E)$_r$-M-Z or -Q-D-L-(E)$_r$-M-A as defined in claim 1 of PCT Patent Application No. WO-A-2004/031118 or US Patent Application No. US-A-2006/0148830, and the other of $R_1$ and $R_2$ is hydrogen, and any salt, complex or prodrug thereof.

Alternatively, for example, we reserve the right to exclude from the present invention the use of all compounds of Formula I in which one or both of $R_1$ and $R_2$ is within the definition of the moiety -Q-D-L-(E)$_r$-M-Z or -Q-D-L-(E)$_r$-M-A as defined in claim 1 of PCT Patent Application No. WO-A-2004/031118 or US Patent Application No. US-A-2006/0148830, and any salt, complex or prodrug thereof.

Alternatively, for example, we reserve the right to exclude from the present invention the use of all compounds of Formula I which are within the definition of compounds of formula I-A in claim 68 of US Patent Application No. US-A-2006/0148830, and any salt, complex or prodrug thereof.

Alternatively, for example, we reserve the right to exclude from the present invention the use of all compounds of Formula I which are within the definition of compounds of formula I in claim 1 of US Patent Application No. US-A-2006/0148830, and any salt, complex or prodrug thereof.

The compound may particularly be used in the treatment or prophylaxis of hypersensitivity, smooth muscle disorders, spasmodic conditions, allergic conditions, inflammatory conditions and/or pain such as, for example but not limited to, asthma, cough, pruritus, food intolerance, psoriasis, croup, irritable bowel syndrome, tinnitus, Meniere's disease, stress-induced ulceration or acetylsalicylic acid-induced ulceration, primary dysmenorrhea, pre-term labour, pre-term contractions, diarrhoea, gastrointestinal cramps, diverticular disease, achalasia, Hirschsprung's disease, gastro-oesophageal reflux disease, myotonic dystrophy, gallstone disease, constipation, post-surgical gastroparesis syndrome, paralytic ileus, post-operative ileus, diabetic gastroparesis, bowel paresis, intestinal pseudo-obstruction, peripheral arterial diseases, Raynaud's syndrome and coronary artery spasm, angina, peripheral arterial disease, hypertension, hypotension, vascular paresis and other vascular disorders, bladder disorders, nausea, allergic rhinitis, allergic dermatitis, inflammation, inflammatory bowel disease, ileitis, pancreatitis, cholecystitis, non-allergic rhinitis, oesophagitis, osteoarthritis, rheumatoid arthritis, Huntington's disease, cerebral ischemia, acute inflammatory pain, neuropathic pain, visceral pain, dental pain and headaches, for the maintenance of normal gut function, as a calmative for the gut, to maintain normal breathing, to ease motion sickness and vertigo, to soothe sore throats and coughs, to ease nausea and vomiting, as an aid to maintain normal digestion, to ease upset stomachs, to warm hands and feet, to aid normal menstruation, to maintain normal blood pressure, to normalise bowel movement, to maintain a healthy immune system, to aid in the recovery from colds and flu, as a decongestant, to soothe headaches, to relieve muscle soreness, to ease mild aches and pains, to provide relief from toothache, to provide relief from mouth ulcers, to maintain healthy joints, to help limit cellulite occurrence and as an aid to weight loss.

According to a second aspect of the present invention, there is provided the use of a compound of formula I or a physiologically acceptable salt, complex or prodrug thereof, in the treatment or prophylaxis of, or in the preparation of a medicament, foodstuff, beverage (for example in a functional food or beverage), food supplement, beverage supplement or other physiologically compatible composition for the treatment or prophylaxis of, hypersensitivity, smooth muscle disorders, spasmodic conditions, allergic conditions, inflammatory conditions and/or pain such as, for example but not limited to, asthma, cough, pruritus, food intolerance, psoriasis, croup, irritable bowel syndrome, tinnitus, Meniere's disease, stress-induced ulceration or acetylsalicylic acid-induced ulceration, primary dysmenorrhea, pre-term labour, pre-term contractions, diarrhoea, gastrointestinal cramps, diverticular disease, achalasia, Hirschsprung's disease, gastro-oesophageal reflux disease, myotonic dystrophy, gallstone disease, constipation, post-surgical gastroparesis syndrome, paralytic ileus, post-operative ileus, diabetic gastroparesis, bowel paresis, intestinal pseudo-obstruction, peripheral arterial diseases, Raynaud's syndrome and coronary artery spasm, angina, peripheral arterial disease, hypertension, hypotension, vascular paresis and other vascular disorders, bladder disorders, nausea, allergic rhinitis, allergic dermatitis, inflammation, inflammatory bowel disease, ileitis, pancreatitis, cholecystitis, non-allergic rhinitis, oesophagitis, osteoarthritis, rheumatoid arthritis, Huntington's disease, cerebral ischemia, acute inflammatory pain, neuropathic pain, visceral pain, dental pain and headaches, for the maintenance of normal gut function, as a calmative for the gut, to maintain normal breathing, to ease motion sickness and vertigo, to soothe sore throats and coughs, to ease nausea and vomiting, as an aid to maintain normal digestion, to ease upset stomachs, to warm hands and feet, to aid normal menstruation, to maintain normal blood pressure, to normalise bowel movement, to maintain a healthy immune system, to aid in the recovery from colds and flu, as a decongestant, to soothe headaches, to relieve muscle soreness, to ease mild aches and pains, to provide relief from toothache, to provide relief from mouth ulcers, to maintain healthy joints, to help limit cellulite occurrence and as an aid to weight loss.

According to a third aspect of the present invention, there is provided a method for treating or preventing hypersensitivity, smooth muscle disorders, spasmodic conditions, allergic conditions, inflammatory conditions and/or pain in a human or non-human subject in need thereof, the method comprising administering to the subject an effective amount of a compound of formula I or a physiologically acceptable salt, complex or prodrug thereof.

Therapeutic use of the compounds may be under medical or veterinary supervision or control, or may be self-administered (in the case of humans) or under the control of a person not veterinarily qualified (in the case of non-human animals).

Non-therapeutic use of the compounds is also possible, and constitutes an embodiment of the third aspect of the present invention. Such non-therapeutic use will typically comprise the precautionary taking of the compound by a healthy human or the precautionary administration of the compound to a healthy non-human animal outside the context of medical or veterinary supervision and control, e.g. self-administration (in the case of humans), for example in foodstuffs to maintain normal blood pressure.

According to a fourth aspect of the present invention, there is provided a pharmaceutical composition (medicament), foodstuff or beverage (for example, a functional foodstuff or beverage), food supplement, beverage supplement or other physiologically compatible composition, comprising a compound of formula I or a physiologically acceptable salt, complex or prodrug thereof and a physiologically acceptable carrier thereof.

The pharmaceutical composition, foodstuff, beverage, food supplement, beverage supplement or the other physiologically compatible composition, is preferably suitable and intended for use in the treatment or prophylaxis of hypersensitivity, smooth muscle disorders, spasmodic conditions, allergic conditions, inflammatory conditions and/or pain in a human or non-human subject, and the compound of formula I or a physiologically acceptable salt, complex or prodrug thereof is preferably present in an amount which is effective for that purpose when administered in an appropriate dosage to the subject.

The pharmaceutical composition, foodstuff, beverage, food supplement, beverage supplement or the physiologically compatible composition, may be provided in unit dosage form, whereby typically one or more unit dosages are administered to the subject. Alternatively, the pharmaceutical composition, foodstuff, beverage, food supplement, beverage supplement or the physiologically compatible composition, may be provided in a form which does not comprise unit dosages, and in that case a suitable dosage is typically measured out for administration.

A compound of general formula I or a physiologically acceptable salt, complex or prodrug thereof may, if desired, be used in association with one or more additional compounds of general formula I or physiologically acceptable salt, complex or prodrug thereof, or with one or more additional agent having activity against hypersensitivity, smooth muscle disorders, spasmodic conditions, allergic conditions, inflammatory conditions and/or pain or against side effects of such an agent. All such compounds, whether used singly or in combination, are referred to herein as "active agents", provided that the active agent as used in the present invention includes at least one compound of general formula I or a physiologically acceptable salt, complex or prodrug thereof.

According to a fifth aspect of the present invention, there is provided a method of manufacturing a pharmaceutical composition (medicament), foodstuff, beverage, food supplement, beverage supplement or the physiologically compatible composition, comprising a compound of formula I or a physiologically acceptable salt, complex or prodrug thereof and a physiologically acceptable carrier therefor, the method comprising bringing into admixture the said compound of formula I or a physiologically acceptable salt, complex or prodrug thereof and the physiologically acceptable carrier therefor.

After the ingredients of the pharmaceutical composition, foodstuff, beverage, foodstuff additive, beverage additive or other physiologically compatible composition have been brought into admixture, the composition is preferably packaged with instructions for use in the treatment or prophylaxis of hypersensitivity, smooth muscle disorders, spasmodic conditions, allergic conditions, inflammatory conditions and/or pain in a human or non-human subject, the said instructions typically including dosage information, information concerning the appropriate administration route and protocol, and safety information relevant to the said intended use.

Certain of the compounds of formula I and their physiologically acceptable salts, complexes and prodrugs are novel per se, and these chemical compounds themselves constitute a further aspect of the present invention.

According to a sixth aspect of the present invention, there is provided a compound of general formula Ia:

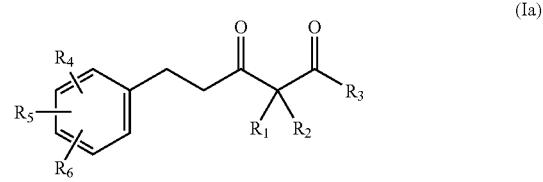

wherein:
$R_1$ and $R_2$ are, independently of each other, selected from hydrogen, optionally substituted $C_{1-10}$ alkyl, optionally substituted —CO—($C_{1-10}$ alkyl), optionally substituted $C_{3-10}$ cycloalkyl, optionally substituted —CO—($C_{3-10}$ cycloalkyl), optionally substituted $C_{2-10}$ alkenyl, optionally substituted —CO—($C_{2-10}$ alkenyl), optionally substituted aryl, and optionally substituted —CO-aryl, or $R_1$ and $R_2$ together represent an optionally substituted saturated or unsaturated $C_{1-10}$ alkylidene group, or an optionally substituted saturated or unsaturated $C_{3-10}$ cycloalkylidene group, or $R_1$ and $R_2$ together with the carbon atom to which they are attached represent an optionally substituted saturated or unsaturated organic ring containing 3, 4, 5, 6, 7 or 8 ring carbon atoms and optionally 1, 2 or 3 ring heteroatoms selected from O, N and S;

$R_3$, which may be the same as, or different from, either of $R_1$ and $R_2$, is selected from optionally substituted $C_{1-10}$ alkyl, optionally substituted $C_{3-10}$ cycloalkyl, optionally substituted $C_{2-10}$ alkenyl, and optionally substituted aryl;

$R_4$, $R_5$ and $R_6$ are, independently of each other, selected from hydrogen, optionally substituted $C_{1-10}$ alkyl, OH, optionally substituted $C_{1-10}$ alkoxy, halo, optionally substituted aryloxy, optionally substituted ($C_{1-10}$ alkyl)-S—(O)$_n$— where n=0, 1 or 2, optionally substituted aryl-S(O)$_n$— where n=0, 1 or 2, or $R_4$ and $R_5$ together represent an optionally substituted saturated or unsaturated organic chain containing 1, 2, 3, 4, 5, 6 or 7 chain carbon atoms and optionally 1, 2 or 3 chain heteroatoms selected from O, N and S, provided that the chain is at least 3 atoms long;

with the provisos that, when $R_1$=$R_2$=hydrogen, then:
(i) any optionally substituted $C_{1-10}$ alkyl or optionally substituted $C_{2-10}$ alkenyl for $R_3$ must have a branch point at one or more of the α and β positions counted from the carbonyl group (or tautomeric form thereof) to which $R_3$ is attached;
(ii) when additionally $R_3$ is un-substituted phenyl and $R_6$ is hydrogen, then (a) $R_4$ cannot be a group selected from 4-vinyl or 2-chloro when $R_5$=hydrogen, (b) $R_5$ cannot be 3-methoxy or 3-ethoxy when $R_4$ is 4-hydroxy, and (c) $R_4$ and $R_5$ cannot both be hydrogen; and
(iii) when additionally $R_4$ is 4-methoxy and $R_6$ is hydrogen, then (a) $R_3$ cannot be 2-hydroxy-3,6-dimethoxyphenyl when $R_5$ is 3-methoxy and (b) $R_3$ cannot be 2-hydroxyphenyl or 4-hydroxyphenyl when $R_5$ is hydrogen;

and with the further proviso that, when $R_2$=$R_5$=$R_6$=hydrogen, $R_3$ is methyl and $R_4$ is 4-methoxy, then $R_1$ cannot be —CO—CH=CH—($C_6H_4$)OMe in which —($C_6H_4$)OMe represents a 4-methoxyphenyl group;

or a physiologically acceptable salt, complex or prodrug thereof;

but not including

2-[4-[3-oxo-5-phenyl-2-(3,4,5-trimethoxybenzoyl)-pentyl]-phenoxy]-benzoic acid benzyl ester;
2-[4-[3-oxo-5-phenyl-2-(3,4,5-trimethoxybenzoyl)-pentyl]-phenoxy]-benzoic acid;
1-(2-hydroxy-3-methoxyphenyl)-5-phenylpentane-1,3-dione;
1-(2-hydroxyphenyl)-5-phenylpentane-1,3-dione;
3-acetyl-4-(4-nitro-benzoyl)-7-phenyl-heptane-2,5-dione;
1,9-diphenyl-4-(3-phenylpropyl)-3,5-nonanedione;
1,5-diphenyl-2-benzyl-1,3-pentanedione;
7-methyl-4-(1-methyl-3-phenylpropyl)-1,9-diphenyl-3,5-nonanedione; and
1,7,9-triphenyl-4-(1,3-diphenylpropyl)-3,5-nonanedione.

If it is to be held by any Patent Office or Court that WO-A-2004/031118, referred to above, discloses or renders obvious any one or more of the above compounds according to the sixth aspect of the present invention, then we reserve the right to further exclude such compounds from the scope of protection of this application and/or its resulting patents.

For example, we reserve the right to exclude from the sixth aspect of the present invention all compounds of Formula Ia in which one of $R_1$ and $R_2$ is $CH_2$-Ph-O-Ph-COOH, the other of $R_1$ and $R_2$ is hydrogen, and $R_4=R_5=R_6=$hydrogen, and any salt, complex or prodrug (e.g. ester) thereof (in which Ph represents a phenyl group).

Alternatively, for example, we reserve the right to exclude from the sixth aspect of the present invention all compounds of Formula Ia in which one, but not both, of $R_1$ and $R_2$ is $CH_2$-Ph-O-Ph-COOH and any salt, complex or prodrug (e.g. ester) thereof.

Alternatively, for example, we reserve the right to exclude from the sixth aspect of the present invention all compounds of Formula Ia in which both of $R_1$ and $R_2$ are $CH_2$-Ph-O-Ph-COOH and any salt, complex or prodrug (e.g. ester) thereof.

Alternatively, for example, we reserve the right to exclude from the sixth aspect of the present invention all compounds of Formula Ia in which one, but not both, of $R_1$ and $R_2$ is optionally substituted $CH_2$-Ph-O-Ph-COOH and any salt, complex or prodrug (e.g. ester) thereof.

Alternatively, for example, we reserve the right to exclude from the sixth aspect of the present invention all compounds of Formula Ia in which both of $R_1$ and $R_2$ are, independently of each other, optionally substituted $CH_2$-Ph-O-Ph-COOH and any salt, complex or prodrug (e.g. ester) thereof.

Alternatively, for example, we reserve the right to exclude from the sixth aspect of the present invention any of the specific groups of compounds just mentioned, but only to the extent that in those excluded compounds $R_3$ is an aryl group, such as optionally substituted phenyl.

Alternatively, for example, we reserve the right to exclude from the sixth aspect of the present invention all compounds of Formula Ia in which one, but not both, of $R_1$ and $R_2$ is within the definition of the moiety -Q-D-L-(E)$_r$-M-Z or -Q-D-L-(E)$_r$-M-A as defined in claim 1 of PCT Patent Application No. WO-A-2004/031118 or US Patent Application No. US-A-2006/0148830, and the other of $R_1$ and $R_2$ is hydrogen, and any salt, complex or prodrug thereof.

Alternatively, for example, we reserve the right to exclude from the sixth aspect of the present invention all compounds of Formula Ia in which one or both of $R_1$ and $R_2$ is within the definition of the moiety -Q-D-L-(E)$_r$-M-Z or -Q-D-L-(E)$_r$-M-A as defined in claim 1 of PCT Patent Application No. WO-A-2004/031118 or US Patent Application No. US-A-2006/0148830, and any salt, complex or prodrug thereof.

Alternatively, for example, we reserve the right to exclude from the sixth aspect of the present invention all compounds of Formula Ia which are within the definition of compounds of formula I-A in claim 68 of US Patent Application No. US-A-2006/0148830, and any salt, complex or prodrug thereof.

Alternatively, for example, we reserve the right to exclude from the sixth aspect of the present invention the use of all compounds of Formula Ia which are within the definition of compounds of formula I in claim 1 of US Patent Application No. US-A-2006/0148830, and any salt, complex or prodrug thereof.

The physiologically unacceptable salts and complexes of the compounds of general formula I are new per se, and constitute a seventh aspect of the present invention. They may be used as intermediates in the preparation of the compounds of general formula I and their physiologically acceptable salts, complexes and prodrugs. In one embodiment of this aspect of the present invention, the physiologically unacceptable salts and complexes of the compounds of general formula Ia as defined above may be particularly mentioned.

The compounds of formula I and their salts, complexes and physiologically acceptable prodrugs may be obtained from readily available starting materials by chemical reactions which will be well known and understood by those skilled in the art. The compounds are relatively simple organic molecules and their synthesis will present no undue difficulty to the skilled worker.

The preferred methods for the preparation of the compounds of formula I and their salts, complexes and physiologically acceptable prodrugs are themselves novel in view of the novelty of the compounds themselves, and constitute further aspects of the present invention.

According to an eighth aspect of the present invention, there is provided a method of preparing a compound of general formula I as defined above or a salt, complex or physiologically acceptable prodrug thereof, which method comprises selectively reducing the aliphatic carbon-carbon double bond marked * in a compound of general formula II:

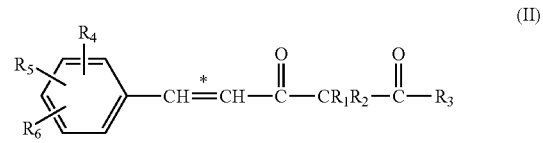

wherein $R_1$ to $R_6$ are as defined above for general formula I, or a salt or complex thereof, to obtain the compound of general formula I.

An example of a suitable reducing agent for effecting the selective reduction is hydrogen in the presence of a metal catalyst such as Raney nickel or palladium on carbon.

Functional groups such as the carbonyl groups, which are susceptible to reduction but are not desired to be reduced, may be protected for the reduction in a generally known manner. The protecting group(s) used will subsequently be removed in a conventional manner to provide the deprotected product.

The reaction, and any subsequent deprotection that may be necessary, yields a compound of general formula I, which may be converted into a salt, complex or prodrug thereof by standard chemical reactions. If initially a salt or complex is formed which is not physiologically compatible, such a compound may subsequently be converted by standard chemical techniques into a physiologically acceptable salt or complex of the compound of general formula I, and optionally then to a physiologically acceptable prodrug.

According to a ninth aspect of the present invention, there is provided a method for preparing a compound of general formula I as defined above or a salt, complex or physiologically acceptable prodrug thereof, which method comprises condensing a compound of general formula III with a compound of general formula IV:

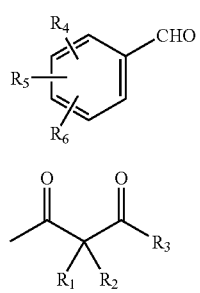

wherein $R_1$ to $R_6$ are as defined above for general formula I, optionally in the presence of a chelating agent, to deactivate the carbon between the two carbonyl groups (or other tautomeric form) in formula IV in favour of the terminal methyl carbon atom, to obtain the compound of general formula I after reduction of the resulting double bond.

Examples of such chelating agents are boron trioxide and titanium tetrachloride.

The reaction yields a compound of general formula I, which may be converted into a salt, complex or physiologically acceptable prodrug thereof by standard chemical reactions. If initially a salt or complex is formed which is not physiologically compatible, such a compound may subsequently be converted by standard chemical techniques (salt or ligand displacement) into a physiologically acceptable salt or complex of the compound of general formula I, and optionally then to a physiologically acceptable prodrug.

Certain of the compounds of general formula II and their salts, complexes and protected forms are novel per se, and these chemical compounds themselves constitute a further aspect of the present invention.

According to a tenth aspect of the present invention, therefore, there is provided a compound of general formula IIa:

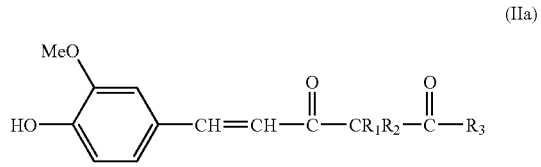

wherein:
$R_1$ and $R_2$ are, independently of each other, selected from hydrogen, optionally substituted $C_{1-10}$ alkyl, optionally substituted —CO—($C_{1-10}$ alkyl), optionally substituted $C_{3-10}$ cycloalkyl, optionally substituted —CO—($C_{3-10}$ cycloalkyl), optionally substituted $C_{2-10}$ alkenyl, optionally substituted —CO—($C_{2-10}$ alkenyl), optionally substituted aryl and optionally substituted —CO-aryl, or $R_1$ and $R_2$ together represent an optionally substituted saturated or unsaturated $C_{1-10}$ alkylidene group or an optionally substituted saturated or unsaturated organic ring containing 3, 4, 5, 6, 7 or 8 ring carbon atoms and optionally 1, 2 or 3 ring heteroatoms selected from O, N and S;

$R_3$, which may be the same as, or different from, either of $R_1$ and $R_2$, is selected from optionally substituted $C_{1-10}$ alkyl, optionally substituted $C_{3-10}$ cycloalkyl, optionally substituted $C_{2-10}$ alkenyl, and optionally substituted aryl;

or a salt, complex or protected form thereof;

with the proviso that, when $R_1=R_2$=hydrogen, then (a) any optionally substituted $C_{1-10}$ alkyl or optionally substituted $C_{2-10}$ alkenyl for $R_3$ must have a branch point at one or more of the α and β positions counted from the carbonyl group (or tautomeric form thereof) to which $R_3$ is attached; and (b) $R_3$ cannot be unsubstituted phenyl.

Furthermore, the protected forms of the compounds of general formula Ia and their salts and complexes, which are initially prepared if a protected form of the compound of general formula Ia or a salt or complex thereof is used as starting material, are also novel per se, and these chemical compounds themselves constitute a further (eleventh) aspect of the present invention.

If it is to be held by any Patent Office or Court that WO-A-2004/031118, referred to above, discloses or renders obvious any one or more of the above compounds according to the tenth and eleventh aspects of the present invention, then we reserve the right to further exclude such compounds from the scope of protection of this application and/or its resulting patents.

For example, we reserve the right to exclude from the tenth and eleventh aspects of the present invention all protected forms, salts and complexes of compounds of Formula Ia and all compounds of Formula IIa and salts, complexes and protected forms thereof in which one of $R_1$ and $R_2$ is $CH_2$-Ph-O-Ph-COOH, the other of $R_1$ and $R_2$ is hydrogen, and $R_4=R_5=R_6$=hydrogen.

Alternatively, for example, we reserve the right to exclude from the tenth and eleventh aspects of the present invention all protected forms, salts and complexes of compounds of Formula Ia and all compounds of Formula IIa and salts, complexes and protected forms thereof in which one, but not both, of $R_1$ and $R_2$ is $CH_2$-Ph-O-Ph-COOH.

Alternatively, for example, we reserve the right to exclude from the tenth and eleventh aspects of the present invention all protected forms, salts and complexes of compounds of Formula Ia and all compounds of Formula IIa and salts, complexes and protected forms thereof in which both of $R_1$ and $R_2$ are $CH_2$-Ph-O-Ph-COOH.

Alternatively, for example, we reserve the right to exclude from the tenth and eleventh aspects of the present invention all protected forms, salts and complexes of compounds of Formula Ia and all compounds of Formula Ia and salts, complexes and protected forms thereof in which one, but not both, of $R_1$ and $R_2$ is optionally substituted $CH_2$-Ph-O-Ph-COOH.

Alternatively, for example, we reserve the right to exclude from the tenth and eleventh aspects of the present invention all protected forms, salts and complexes of compounds of Formula Ia and all compounds of Formula Ia and salts, complexes and protected forms thereof in which both of $R_1$ and $R_2$ are, independently of each other, optionally substituted $CH_2$-Ph-O-Ph-COOH.

Alternatively, for example, we reserve the right to exclude from the tenth and eleventh aspects of the present invention any of the specific groups of compounds just mentioned, but only to the extent that in those excluded compounds $R_3$ is an aryl group, such as optionally substituted phenyl.

Alternatively, for example, we reserve the right to exclude from the tenth and eleventh aspects of the present invention all protected forms, salts and complexes of compounds of Formula Ia and all compounds of Formula Ia and salts, complexes and protected forms thereof in which one, but not both, of $R_1$ and $R_2$ is within the definition of the moiety -Q-D-L-(E)$_r$-M-Z or -Q-D-L-(E)$_r$-M-A as defined in claim 1 of PCT Patent Application No. WO-A-2004/031118 or US Patent Application No. US-A-2006/0148830, and the other of $R_1$ and $R_2$ is hydrogen.

Alternatively, for example, we reserve the right to exclude from the tenth and eleventh aspects of the present invention all protected forms, salts and complexes of compounds of Formula Ia and all compounds of Formula Ia and salts, complexes and protected forms thereof in which one or both of $R_1$ and $R_2$ is within the definition of the moiety -Q-D-L-(E)$_r$-M-Z or -Q-D-L-(E)$_r$-M-A as defined in claim 1 of PCT Patent Application No. WO-A-2004/031118 or US Patent Application No. US-A-2006/0148830.

Alternatively, for example, we reserve the right to exclude from the tenth and eleventh aspects of the present invention all protected forms, salts and complexes of compounds of Formula Ia and all compounds of Formula Ia and salts, complexes and protected forms thereof which are within the definition of compounds of formula I-A in claim 68 of US Patent Application No. US-A-2006/0148830.

Alternatively, for example, we reserve the right to exclude from the tenth and eleventh aspects of the present invention all protected forms, salts and complexes of compounds of Formula Ia and all compounds of Formula IIa and salts, complexes and protected forms thereof which are within the definition of compounds of formula I in claim 1 of US Patent Application No. US-A-2006/0148830.

According to a twelfth aspect of the present invention, there is provided a method for preparing a compound of general formula I or II as defined above or a salt or complex thereof in which one or both of $R_1$ and $R_2$ is an alkyl group and the other of $R_1$ and $R_2$, if not an alkyl group, is a hydrogen atom, the method comprising alkylating the corresponding compound of general formula I or II or salt thereof in which both of $R_1$ and $R_2$ are hydrogen atoms by initially protecting any phenolic groups of the said compound using a base, (e.g. sodium hydride (NaH)) and a protecting group, (e.g. trimethylsilyl) in the presence of a suitable solvent (e.g. tetrahydrofuran (THF)) and subsequently reacting the treated compound with an alkylating agent (e.g. an alkyl iodide, for example methyl iodide), in the presence of a base (e.g. potassium carbonate, sodium hydride or potassium t-butoxide), to obtain the alkylated compound.

According to a thirteenth aspect of the present invention, there is provided a method for preparing a compound of general formula I or II as defined above or a salt or complex thereof the method comprising reacting a compound of general formula V.

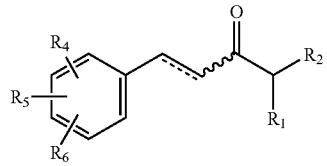

(V)

or a suitably protected form thereof, wherein $R_1$, $R_2$, $R_4$, $R_5$ and $R_6$ are as defined respectively for formulae I and II, wherein ⋯⋯ represents a single or double bond and the wavy line represents either the (E) or (Z) isomer when ⋯⋯ is a double bond;

with an activated carboxylic acid having the formula HO.COR$_3$ or a suitably protected form thereof, where $R_3$ is as defined respectively for formula I and II, in the presence of base and optionally in a suitable solvent (e.g. THF), to obtain the desired compound.

The reaction may conveniently be carried out, for example, in the presence of lithium hexamethyldisylazide (LHMDS) as the base.

The compounds of general formula I show activity in the modulation of the TRPV1 receptor, modulation of smooth muscle tone, inhibition of tissue remodelling, and inhibition of inflammatory mediator production. From this, it is seen more generally that the compounds of general formula I and their salts, complexes and prodrugs have one or more of the following biological activities: (1) they modulate the TRPV1 receptor; (2) they modulate smooth muscle tone; (3) they inhibit tissue remodeling; and (4) they have anti-inflammatory activity.

The data show that the compounds of general formula I can bind to and modulate the TRPV1 receptor and affect the release of calcitonin gene-related peptide (CGRP) in dorsal root ganglions (DRGs), and that the compounds can behave in this respect as agonists, partial agonists or antagonists of the TRPV1 receptor.

Preferably, therefore, the compounds of general formula I have one or more of the following biological activities: modulation of the TRPV1 receptor; modulation of smooth muscle tone; inhibition of tissue remodelling; and anti-inflammatory activity. More preferably, the compounds have at least two of these activities, for example at least three of the said activities. Most preferably, the compounds have all of the said activities.

This combination of activities is strongly indicative of compounds that will provide for treatment or prophylaxis of hypersensitivity, smooth muscle disorders, spasmodic conditions, allergic conditions, inflammatory conditions and/or pain such as, for example but not limited to, asthma, cough, pruritus, food intolerance, psoriasis, croup, irritable bowel syndrome, tinnitus, Meniere's disease, stress-induced ulceration or acetylsalicylic acid-induced ulceration, primary dysmenorrhea, pre-term labour, pre-term contractions, diarrhoea, gastrointestinal cramps, diverticular disease, achalasia, Hirschsprung's disease, gastro-oesophageal reflux disease, myotonic dystrophy, gallstone disease, constipation, post-surgical gastroparesis syndrome, paralytic ileus, post-operative ileus, diabetic gastroparesis, bowel paresis, intestinal pseudo-obstruction, peripheral arterial diseases, Raynaud's syndrome and coronary artery spasm, angina, peripheral arterial disease, hypertension, hypotension, vascular paresis and other vascular disorders, bladder disorders, nausea, allergic rhinitis, allergic dermatitis, inflammation, inflammatory bowel disease, ileitis, pancreatitis, cholecystitis, non-allergic rhinitis, oesophagitis, osteoarthritis, rheumatoid arthritis, Huntington's disease, cerebral ischemia, acute inflammatory pain, neuropathic pain, visceral pain, dental pain and headaches, for the maintenance of normal gut function, as a calmative for the gut, to maintain normal breathing, to ease motion sickness and vertigo, to soothe sore throats and coughs, to ease nausea and vomiting, as an aid to maintain normal digestion, to ease upset stomachs, to warm hands and feet, to aid normal menstruation, to maintain normal blood pressure, to normalise bowel movement, to maintain a healthy immune system, to aid in the recovery from colds and flu, as a decongestant, to soothe headaches, to relieve muscle soreness, to ease mild aches and pains, to provide relief from toothache, to provide relief from mouth ulcers, to maintain healthy joints, to help limit cellulite occurrence and as an aid to weight loss.

In accordance with a further aspect of the present invention, therefore, there is provided a method for obtaining at least one, for example two, more preferably three and most preferably all of the following biological activities in human or other tissue in vitro or in vivo: modulation of the TRPV1 receptor; modulation of smooth muscle tone; inhibition of tissue remodelling; and anti-inflammatory activity; the method comprising contacting the said tissue in vitro or in vivo with an effective amount of a compound of general formula I or a salt, complex or prodrug thereof.

DETAILED DESCRIPTION OF THE INVENTION

The Compounds of Formulae I and II

Chirality

Certain of the compounds of general formulae I and II contain asymmetric carbon atoms, and are therefore chiral.

The present invention extends to all optical isomers of such compounds, whether in the form of racemates or resolved enantiomers.

Double Bond Isomerism

The compounds of general formula II and those compounds of general formula I and II that contain a double bond in one or more of the variable R groups are capable of double bond isomerism whereby each double bond may in principle exist in an (E) or a (Z) form.

The present invention extends to all double bond isomers of such compounds, whether in the form of isomer mixtures in any relative proportion or as substantially pure isomers.

Substitution Position Isomerism

The compounds of general formula I and II are capable of substitution position isomerism, for example in the locations of the groups $R_4$, $R_5$ and $R_6$ and in the location of any optional substituents of the R groups.

The present invention extends to all substitution position isomers of such compounds, whether in the form of isomer mixtures in any relative proportion or as substantially pure isomers.

For example, in one possible realisation of the compounds of formulae I and II, $R_6$ may be hydrogen, $R_4$ may be meta to the dioxo-containing chain and $R_5$ may be para to the dioxo-containing chain. It is most preferred that in this realisation $R_4$ represents an unsubstituted $C_{1-4}$ alkoxy group such as methoxy and $R_5$ represents hydroxyl.

Tautomerism

The compounds of general formulae I and II (and Ia and IIa) in which one or both of $R_1$ and $R_2$ are hydrogen are capable of tautomerisation, particularly in solution, to form enols having a carbon-carbon double bond between one of the carbonyl carbon atoms and the central carbon atom between the carbonyl groups. Such enol tautomers of the compounds and their uses are included within the scope of the present application and subsequent patents.

Alkyl

"$C_{x-y}$ alkyl" where x and y are any integers means an aliphatic hydrocarbon group having from x to y carbon atoms.

The alkyl group may be straight or branched. "Branched" means that at least one carbon branch point is present in the group.

The alkyl group is preferably a lower alkyl group. "Lower alkyl" means an alkyl group, straight or branched, having 1 to about 6 carbon atoms, e.g. 2, 3, 4, 5 or 6 carbon atoms.

Exemplary alkyl groups include methyl, ethyl, n-propyl, i-propyl, n-butyl, t-butyl, s-butyl, n-pentyl, 2-pentyl, 3-pentyl, n-hexyl, 2-hexyl, 3-hexyl, n-heptyl, 2-heptyl, 3-heptyl, 4-heptyl, 2-methyl-but-1-yl, 2-methyl-but-3-yl, 2-methyl-pent-1-yl, 2-methyl-pent-3-yl.

The alkyl group may be optionally substituted, e.g. as exemplified below. The phenylmethyl, phenylethyl and phenylpropyl groups are thus examples of substituted alkyl groups.

Cycloalkyl

"$C_{x-y}$ cycloalkyl" where x and y are any integers means a cyclic non-aromatic hydrocarbon group having from x to y carbon atoms. The cycloalkyl group may include non-aromatic unsaturation.

The cycloalkyl group preferably has 3 to about 6 carbon atoms, e.g. 3, 4, 5 or 6 carbon atoms.

Exemplary cycloalkyl groups include cyclopropyl, cyclobutyl, cyclopentyl, cyclohexyl, cyclopentenyl, cyclohexenyl.

The cycloalkyl group may be optionally substituted, as defined below, e.g. as exemplified below.

Alkenyl

"$C_{x-y}$ alkenyl" where x and y are any integers means an unsaturated aliphatic hydrocarbon group having from x to y carbon atoms. The unsaturation may include one or more double bond, one or more triple bond or any combination thereof. The alkenyl group may be straight or branched. "Branched" means that at least one carbon branch point is present in the group.

Any double bond may, independently of any other double bond in the group, be in either the (E) or the (Z) configuration.

The alkenyl group is preferably a lower alkenyl group. "Lower alkenyl" means an alkenyl group, straight or branched, having 2 to about 6 carbon atoms, e.g. 2, 3, 4, 5 or 6 carbon atoms.

Exemplary alkenyl groups include ethenyl, n-propenyl, i-propenyl, but-1-en-1-yl, but-2-en-1-yl, but-3-en-1-yl, pent-1-en-1-yl, pent-2-en-1-yl, pent-3-en-1-yl, pent-4-en-1-yl, pent-1-en-2-yl, pent-2-en-2-yl, pent-3-en-2-yl, pent-4-en-2-yl, pent-1-en-3-yl, pent-2-en-3-yl, pentadien-1-yl, pentadien-2-yl, pentadien-3-yl. Where alternative (E) and (Z) forms are possible, each is to be considered as individually identified.

The alkenyl group may be optionally substituted, e.g. as exemplified below.

Aryl

"Aryl" means any aromatic group, preferably having up to about 12 carbon atoms, e.g. 6, 7, 8, 9, 10, 11 or 12 carbon atoms. The aryl group may comprise one, two or more rings. Where two or more rings are present they may if desired be fused.

The ring system of the aryl group may include one or more heteroatoms such as, for example, O, N and S.

The aryl group preferably comprises one or more phenyl ring.

Exemplary aryl groups include phenyl, naphthyl, biphenyl, pyridyl, pyrazinyl, pyrimidinyl, furyl, thiophenyl, pyrrolyl, oxazolyl, thiazolyl, pyrazolyl, imidazolyl, 1,2,3-triazolyl, 1,2,4-triazolyl, tetrazolyl, indolyl and purinyl.

The aryl group may be optionally substituted, e.g. as exemplified below.

Alkylidene Group

"Alkylidene" means any alkyl or alkenyl group linked to the remainder of the molecule via a double bond. The definitions and illustrations provided herein for alkyl and alkenyl groups apply with appropriate modification also to alkylidene groups.

Cycloalkylidene Group

"Cycloalkylidene" means any cycloalkyl group linked to the remainder of the molecule via a double bond. The definitions and illustrations provided herein for cycloalkyl groups apply with appropriate modification also to cycloalkylidene groups.

Organic Ring Containing Ring Carbon Atoms and Optionally Ring Heteroatoms

The expression "organic ring containing x chain ring atoms and optionally y ring heteroatoms" where x and y are integers means any cyclic organic group consisting of a ring of x carbon atoms and optionally y heteroatoms. The ring may comprise one or more branch point. The bonds between the atoms of the chain may be selected from single, double or triple bonds. At least some of the atoms of the chain will also be linked to side hydrogen atoms unless the chain is substituted or branched in such a way that side hydrogen atoms are not possible at that location.

If variable configurations of any double bond are possible, such a double bond may, independently of any other double bond in the chain, be in either the (E) or the (Z) configuration.

The organic chain is preferably a saturated or unsaturated alkylene group containing 2, 3, 4, 5 or 6 carbon atoms.

Exemplary organic chains include ethylene, n-propylene, i-propylene, n-butylene, s-butylene, n-pentylene.

Optionally Substituted

"Optionally substituted" as applied to any group means that the said group may if desired be substituted with one or more substituents, which may be the same or different, preferably one or more substituents which individually have a size which is small in relation to the parent group being substituted (e.g. less than about 20% of the largest molecular dimension).

A group cannot be a substituent of its own kind if it would thereby form a group of that kind which would then fall outside the definition of the compounds of formulae I and II (or Ia and IIa) (e.g. an alkyl group cannot be a substituent of another alkyl group so that an alkyl group having too many carbon atoms would result).

Examples of suitable substituents include halo (e.g. fluoro, chloro, bromo or iodo), $C_{1-6}$ alkyl, $C_{3-6}$ cycloalkyl, hydroxy, $C_{1-6}$ alkoxy, $C_{2-6}$ alkenloxy, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{6-12}$ aryl, $C_{6-12}$ arylamino, di-$C_{6-12}$ arylamino, $C_{6-12}$ aroylamino, di-$C_{6-12}$ aroylamino, $C_{6-12}$ arylamido, carboxy, $C_{1-6}$ alkoxycarbonyl or $(C_{6-12}$ ar)$(C_{1-10}$ alkoxy)carbonyl, carbamoyl, or any of the above in which a hydrocarbyl moiety is itself substituted by halo, hydroxy, amino, nitro, carbamoyl or carboxy, subject to the size limitation set out above. The word fragment "ar" shall be understood as "aryl" and the word fragment "alk" shall be understood as "alkyl" or "alkenyl".

"Acyl" means an H—CO— or $C_{1-10}$ alkyl-CO— group wherein the alkyl group is as defined below. Preferred acyls contain a lower alkyl. Exemplary acyl groups include formyl, acetyl, propanoyl, 2-methylpropanoyl and butanoyl;

Exemplary substituted alkyl groups include mono- or poly-aryl-substituted alkyl groups such as phenylmethyl, naphthylmethyl, diphenylmethyl, phenylethyl, naphthylethyl, diphenylethyl, phenylpropyl, naphthylpropyl, diphenylpropyl.

Exemplary substituted cycloalkyl groups include mono- or poly-alkyl-substituted cycloalkyl groups such as 1-methylcyclopropyl, 1-methylcyclobutyl, 1-methylcyclopentyl, 1-methylcyclohexyl, 2-methylcyclopropyl, 2-methylcyclobutyl, 2-methylcyclopentyl, 2-methylcyclohexyl.

Exemplary substituted aryl groups include, at any substitution position or combination of positions, $C_{1-6}$ alkoxyphenyl such as methoxyphenyl, hydroxyphenyl, ($C_{1-6}$ alkoxy)(hydroxy)phenyl such as methoxy-hydroxyphenyl, $C_{1-6}$ alkylphenyl such as methylphenyl, ($C_{1-6}$ alkyl)(hydroxy)phenyl such as methyl-hydroxyphenyl, monohalophenyl such as monofluorophenyl or monochlorophenyl, dihalophenyl such as dichlorophenyl or chlorofluorophenyl, carboxyphenyl, $C_{1-6}$ alkoxycarbonylphenyl such as methoxycarbonylphenyl.

Branch Point

The term "branch point" used herein refers to a carbon atom or heteroatom which is connected directly to 3 or 4 other atoms forming part of the skeleton of the compound, particularly carbon atoms or skeletal heteroatoms.

In the following examples, the branch points are denoted by the letter C:

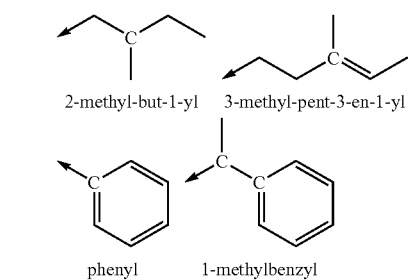

2-methyl-but-1-yl    3-methyl-pent-3-en-1-yl phenyl    1-methylbenzyl

A branch point which is at a carbon atom is referred to herein as a carbon branch point.

In the following example, the branch point is denoted by the letter N (nitrogen)

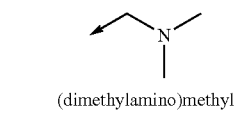

(dimethylamino)methyl

A branch point which is at a heteroatom is referred to herein as a heteroatom branch point. In the definition of a branch point, an atom is considered to form part of the compound (i.e. be "skeletal") if it itself links directly or indirectly to one or more carbon containing moieties. Thus, for example, hydrogen atoms or carbon-free moieties are not considered to form part of the skeleton of the compound.

Where a branch point in $R_3$ is stated to be at an α position counted from the carbonyl group to which $R_3$ is attached, this means that the branch point is directly linked to the carbon atom of the said carbonyl group, for example in the following compound of general formula I (compound 2 as described below):

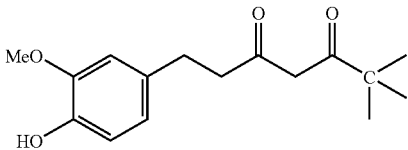

Where a branch point in $R_3$ is stated to be at a β position counted from the carbonyl group to which $R_3$ is attached, this means that the branch is linked through one linker atom (e.g. a carbon atom) to the carbon atom of the said carbonyl group, for example in the following compound of general formula I (compound 28 as described below):

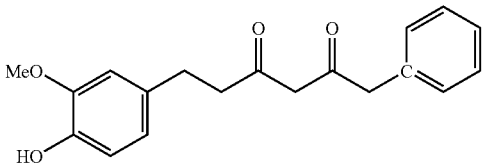

In the compound 31 described below, it will be seen for example that carbon branch points exist at both α and β positions counted from the carbonyl group to which $R_3$ is attached, i.e.,

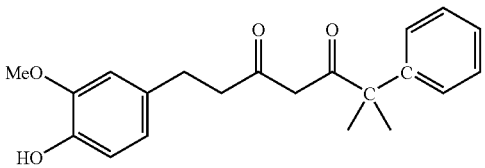

The proviso requirement that any optionally substituted alkyl or optionally substituted alkenyl for $R_3$ must have a branch point at one or more of the α and β positions counted from the carbonyl group to which $R_3$ is attached does not exclude that other branch points may exist in the molecule or that more than one β branch point may exist in the molecule, optionally with or without an α branch point.

Preferences

Preferred are compounds of general formula I and II and their salts, complexes and prodrugs in which, independently of each other, $R_1$ is selected from hydrogen and optionally substituted $C_{1-10}$ alkyl;

$R_2$ is selected from hydrogen and optionally substituted $C_{1-10}$ alkyl;

$R_3$ is selected from optionally substituted $C_{1-10}$ alkyl, optionally substituted $C_{3-10}$ cycloalkyl and optionally substituted aryl;

$R_4$ is hydroxyl or optionally substituted $C_{1-4}$ alkoxy;

$R_5$ is hydroxyl or optionally substituted $C_{1-4}$ alkoxy;

$R_6$ is hydrogen.

Most preferred are such compounds in which, independently of each other:

$R_1$ is selected from hydrogen, unsubstituted $C_{1-6}$ alkyl and phenyl-substituted $C_{1-6}$ alkyl;

$R_2$ is selected from hydrogen, unsubstituted $C_{1-6}$ alkyl and phenyl-substituted $C_{1-6}$ alkyl;

$R_3$ is selected from unsubstituted $C_{1-6}$ alkyl, ($C_{3-6}$ cycloalkyl)-substituted $C_{1-6}$ alkyl, unsubstituted $C_{3-6}$ cycloalkyl, unsubstituted phenyl, mono or poly phenyl-substituted phenyl, ($C_{1-6}$ alkyl)-substituted phenyl, ($C_{1-6}$ alkoxy)-substituted phenyl, mono or poly halo-substituted phenyl where polyhalo substituents may be the same or different, hydroxyl-substituted phenyl, ($C_{1-6}$ alkoxy)(hydroxyl)-disubstituted phenyl, ($C_{1-6}$ alkoxy) carbonyl-substituted phenyl and unsubstituted naphthyl;

$R_4$ is unsubstituted methoxy;

$R_5$ is hydroxyl; and $R_6$ is hydrogen.

$R_4$ may be meta to the dioxo-containing chain and $R_5$ may be para to the dioxo-containing chain.

The halo groups in the mono or poly halo-substituted phenyl for $R_3$ may be selected from fluoro, chloro and iodo. Wherein $R_3$ a phenyl or naphthyl moiety is present, it may be linked at any carbon atom of the moiety and any substituent(s) may be at any other carbon atom(s) of the moiety.

Physiologically Acceptable

"Physiologically acceptable" means it is, within the scope of sound medical and veterinary judgement, suitable for use in contact with the cells of humans and lower animals without undue toxicity, irritation, allergic response and the like, and are commensurate with a reasonable benefit/risk ratio. "Physiologically unacceptable" means it is not suitable for such use.

Salts

"Salt" means the inorganic and organic acid addition salts, and base addition salts, of any compounds of the present invention where such salt formation is possible. These salts can be prepared in situ during the final isolation and purification of the compounds. In particular, acid addition salts can be prepared by separately reacting the purified compound in its free base form with a suitable organic or inorganic acid and isolating the salt thus formed. See, for example S. M. Berge, et al., Pharmaceutical Salts, J. Pharm. Sci., 66: p. 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts.

Examples of suitable acid addition salts are those formed with acids selected from hydrochloric, sulphuric, phosphoric and nitric acids. Examples of suitable base addition salts are those formed with bases selected from sodium hydroxide, potassium hydroxide and ammonium hydroxide.

Complexes

"Complex" means the chemical entity resulting from the non-covalent coordination of any suitable element, ion or compound with moieties of the compounds of general formulae I and II (or Ia and IIa) to provide a stable chemical entity.

In particular, the compounds of general formulae I and II (and Ia and IIa) are β-diketones (or their tautomers), which are well known to complex with transition metal or alkaline earth metal atoms, ions and compounds. The complexes may further include one or more co-ligand, preferably containing an electron donating atom or group such as an oxygen or nitrogen atom. Suitable co-ligands can readily be selected from known chelating agents for the metals in question, and may include, for example, water and organic heterocycles containing nitrogen atoms.

Thus, for example, such complexes may be formed in generally known manner between the compounds of formulae I and II and the following metals: copper, nickel, iron, magnesium, calcium, strontium or barium, optionally with one or more suitable co-ligand.

Prodrugs

"Prodrug" means any compound that is rapidly transformed in vivo to yield the parent compound of the formula I by cleavage of one or more physiologically labile leaving group or by operation of a physiologically initiated chemical reaction, for example by hydrolysis in the gastrointestinal tract or in blood. For example, certain functional groups can be pre-reacted with a carboxyl or other group to become chemically part of a prodrug form of the compound of formula I or II, and such groups may after administration to the patient be rapidly split off or transformed by metabolic processes in vivo (e.g. hydrolysis) to provide the compound of formula I or II in situ. A thorough discussion of prodrugs is provided in the following: Design of Prodrugs, H. Bundgaard, ed., Elsevier, 1985; Methods in Enzymology, K. Widder et al, Ed., Academic Press, 42, p. 309-396, 1985; A Textbook of Drug Design and Development, Krogsgaard-Larsen and H. Bundgaard, ed., Chapter 5; Design and Applications of Prodrugs p. 113-191, 1991; Advanced Drug Delivery Reviews, H. Bundgard, 8, p. 1-38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

Protection/Deprotection

Protection refers to the use of protecting groups to protect reactive functional groups, for example hydroxyl, carboxy or carbonyl groups, where these are desired in the final product, to avoid unwanted participation in the reactions. The protecting group(s) will be removed after the reaction has been completed, to provide the final ("deprotected") compound. Conventional protecting groups may be introduced, removed and generally used in accordance with standard practice, for example see T. W. Green and P. G. M. Wuts in "Protective Groups in Organic Chemistry" John Wiley and Sons, 1991; J. F. W. McOmie in "Protective Groups in Organic Chemistry" Plenum Press, 1973.

Examples of Compounds of General Formula I

Of the compounds of general formula I, particularly preferred are the compounds shown in Tables 1 and 2 and their salts, complexes, prodrugs and protected forms:

TABLE 1

Examples of Compounds of General Formula I

| | $R_1$ | $R_2$ | $R_3$ | $R_4$ | $R_5$ | $R_6$ |
|---|---|---|---|---|---|---|
| 2 | H | H | $C(CH_3)_3$ | 4-OH | 3-OMe | H |
| 1 | H | H | $CH(CH_3)_2$ | 4-OH | 3-OMe | H |
| 28 | H | H | $CH_2Ph$ | 4-OH | 3-OMe | H |
| 31 | H | H | $C(Me)_2Ph$ | 4-OH | 3-OMe | H |
| 29 | H | H | $CH_2Napth$ | 4-OH | 3-OMe | H |
| 30 | H | H | $CHPh_2$ | 4-OH | 3-OMe | H |
| 3 | H | H | $CH_2C(CH_3)_3$ | 4-OH | 3-OMe | H |
| 4 | Me | H | $C(CH_3)_3$ | 4-OH | 3-OMe | H |
| 5 | H | H | cyclopropyl-methyl | 4-OH | 3-OMe | H |
| 6 | H | H | cyclopropyl-dimethyl | 4-OH | 3-OMe | H |
| 7 | Me | H | cyclopropyl-dimethyl | 4-OH | 3-OMe | H |
| 70 | Me | Me | cyclopropyl-dimethyl | 4-OH | 3-OMe | H |
| 8 | H | H | cyclopentyl | 4-OH | 3-OMe | H |
| 9 | H | H | $CH(CH_3)CH_2CH_3$ | 4-OH | 3-OMe | H |
| 10 | H | H | cyclohexyl-methyl | 4-OH | 3-OMe | H |
| 71 | Me | Me | $C(CH_3)_3$ | 4-OH | 3-OMe | H |

In the above formulae, Me = methyl, Napth = 1-napthyl and Ph = phenyl.

TABLE 2

Examples of Compounds of General Formula I

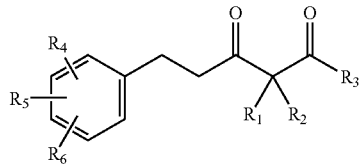

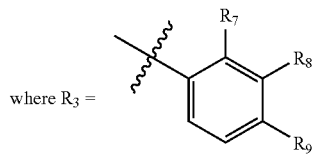

where $R_3$ =

| | $R_1$ | $R_2$ | $R_4$ | $R_5$ | $R_6$ | $R_7$ | $R_8$ | $R_9$ |
|---|---|---|---|---|---|---|---|---|
| 69 | H | H | 4-OH | 3-OMe | H | H | H | H |
| 11 | Me | H | 4-OH | 3-OMe | H | H | H | H |
| 12 | Ft | H | 4-OH | 3-OMe | H | H | H | H |
| 13 | Bn | H | 4-OH | 3-OMe | H | H | H | H |
| 14 | Me | H | 4-OH | 3-OMe | H | H | H | Me |
| 15 | H | H | 4-OH | 3-OMe | H | H | OMe | OH |
| 16 | Me | H | 4-OH | 3-OMe | H | H | OMe | OH |
| 72 | Me | Me | 4-OH | 3-OMe | H | H | OMe | OH |
| 18 | H | H | 4-OH | 3-OMe | H | H | H | Ph |
| 19 | H | H | 4-OH | 3-OMe | H | Ph | H | H |
| 20 | H | H | 4-OH | 3-OMe | H | H | H | F |
| 21 | H | H | 4-OH | 3-OMe | H | H | H | Cl |
| 73 | Me | Me | 4-OH | 3-OMe | H | H | H | F |
| 22 | H | H | 4-OH | 3-OMe | H | H | Cl | H |
| 74 | H | H | 4-OH | 3-OMe | H | Cl | H | H |
| 23 | H | H | 4-OH | 3-OMe | H | H | Cl | Cl |
| 24 | H | H | 4-OH | 3-OMe | H | Cl | H | Cl |
| 75 | H | H | 4-OH | 3-OMe | H | H | Me | Cl |
| 76 | H | H | 4-OH | 3-OMe | H | Me | H | Cl |
| 77 | H | H | 4-OH | 3-OMe | H | Me | Cl | H |
| 78 | H | H | 4-OH | 3-OMe | H | H | Cl | Me |
| 25 | H | H | 4-OH | 3-OMe | H | H | H | $CO_2Me$ |
| 26 | H | H | 4-OH | 3-OMe | H | H | CH=CH—CH=CH | |
| 27 | H | H | 4-OH | 3-OMe | H | CH=CH—CH=CH | | H |
| 32 | Me | Me | 4-OH | 3-OMe | H | H | H | H |
| 79 | Me | Me | 4-OH | 3-OMe | H | H | CH=CH—CH=CH | |
| 80 | H | H | 4-OH | 3-OMe | H | H | H | Me |
| 81 | Me | Me | 4-OH | 3-OMe | H | H | H | Me |
| 17 | Me | H | 4-OH | 3-OMe | H | H | H | OMe |
| 82 | H | H | 4-OH | 3-OMe | H | H | H | CN |
| 83 | H | H | 4-OH | 3-OMe | H | H | H | $C(CH_3)_3$ |
| 84 | H | H | 4-OH | 3-OMe | H | Me | H | H |
| 85 | H | H | 4-OH | 3-OMe | H | H | Me | H |
| 86 | H | H | 4-OH | 3-OMe | 6-Cl | H | CH=CH—CH=CH | |
| 87 | Me | Me | 4-$O(CH_2)_2NH_2.HCl$ | 3-OMe | H | H | H | H |
| 88 | H | H | 4-$O(CH_2)_2NH_2.HCl$ | 3-OMe | H | H | H | H |
| 89 | H | H | 4-OH | 3-OEt | H | H | H | H |

In the above formulae, Me = methyl, Et = ethyl, Bn = benzyl and Ph = phenyl.

Examples of Compounds of General Formula II

Of the compounds of general formula II, particularly preferred are the compounds shown in Tables 3 and 4 and their salts, complexes and protected forms:

TABLE 3

Examples of Compounds of General Formula II

| | $R_1$ | $R_2$ | $R_3$ | $R_4$ | $R_5$ | $R_6$ |
|---|---|---|---|---|---|---|
| 34 | H | H | $C(CH_3)_3$ | 4-OH | 3-OMe | H |
| 33 | H | H | $CH(CH_3)_2$ | 4-OH | 3-OMe | H |
| 60 | H | H | $CH_2Ph$ | 4-OH | 3-OMe | H |
| 63 | H | H | $C(Me)_2Ph$ | 4-OH | 3-OMe | H |
| 61 | H | H | $CH_2Napth$ | 4-OH | 3-OMe | H |
| 62 | H | H | $CHPh_2$ | 4-OH | 3-OMe | H |
| 35 | H | H | $CH_2C(CH_3)_3$ | 4-OH | 3-OMe | H |
| 36 | Me | H | $C(CH_3)_3$ | 4-OH | 3-OMe | H |
| 37 | H | H | cyclopropyl | 4-OH | 3-OMe | H |
| 38 | H | H | 2,2-dimethylcyclopropyl | 4-OH | 3-OMe | H |
| 39 | Me | H | 2,2-dimethylcyclopropyl | 4-OH | 3-OMe | H |

TABLE 3-continued

Examples of Compounds of General Formula II

| | $R_1$ | $R_2$ | $R_3$ | $R_4$ | $R_5$ | $R_6$ |
|---|---|---|---|---|---|---|
| 90 | Me | Me | 1-methylcyclopropyl | 4-OH | 3-OMe | H |
| 40 | H | H | cyclopentyl | 4-OH | 3-OMe | H |
| 41 | H | H | $CH(CH_3)CH_2CH_3$ | 4-OH | 3-OMe | H |
| 42 | H | H | 1-methylcyclohexyl | 4-OH | 3-OMe | H |
| 91 | Me | Me | $C(CH_3)_3$ | 4-OH | 3-OMe | H |

In the above formulae, Me = methyl, Napth = 1-napthyl and Ph = phenyl.

TABLE 4

Examples of Compounds of General Formula II where $R_3 =$ substituted phenyl with $R_7$, $R_8$, $R_9$

| | $R_1$ | $R_2$ | $R_4$ | $R_5$ | $R_6$ | $R_7$ | $R_8$ | $R_9$ |
|---|---|---|---|---|---|---|---|---|
| 68 | H | H | 4-OH | 3-OMe | H | H | H | H |
| 43 | Me | H | 4-OH | 3-OMe | H | H | H | H |
| 44 | Et | H | 4-OH | 3-OMe | H | H | H | H |
| 45 | Bn | H | 4-OH | 3-OMe | H | H | H | H |
| 46 | Me | H | 4-OH | 3-OMe | H | H | H | Me |

TABLE 4-continued

Examples of Compounds of General Formula II

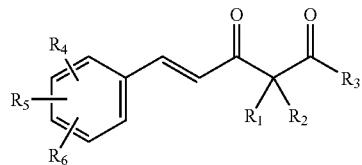

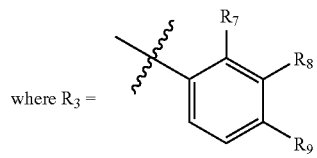

where $R_3 =$

| | $R_1$ | $R_2$ | $R_4$ | $R_5$ | $R_6$ | $R_7$ | $R_8$ | $R_9$ |
|---|---|---|---|---|---|---|---|---|
| 47 | H | H | 4-OH | 3-OMe | H | H | OMe | OH |
| 48 | Me | H | 4-OTBDMS | 3-OMe | H | H | OMe | OTBDMS |
| 92 | Me | Me | 4-OH | 3-OMe | H | H | OMe | OH |
| 50 | H | H | 4-OH | 3-OMe | H | H | H | Ph |
| 51 | H | H | 4-OH | 3-OMe | H | Ph | H | H |
| 52 | H | H | 4-OH | 3-OMe | H | H | H | F |
| 53 | H | H | 4-OH | 3-OMe | H | H | H | Cl |
| 67 | H | H | 4-OH | 3-OMe | H | H | H | I |
| 93 | Me | Me | 4-OH | 3-OMe | H | H | H | F |
| 54 | H | H | 4-OH | 3-OMe | H | H | Cl | H |
| 94 | H | H | 4-OH | 3-OMe | H | Cl | H | H |
| 55 | H | H | 4-OH | 3-OMe | H | H | Cl | Cl |
| 56 | H | H | 4-OH | 3-OMe | H | Cl | H | Cl |
| 95 | H | H | 4-OH | 3-OMe | H | H | Me | Cl |
| 96 | H | H | 4-OH | 3-OMe | H | Me | H | Cl |
| 97 | H | H | 4-OH | 3-OMe | H | Me | Cl | H |
| 98 | H | H | 4-OH | 3-OMe | H | H | Cl | Me |
| 57 | H | H | 4-OH | 3-OMe | H | H | H | $CO_2Me$ |
| 58 | H | H | 4-OH | 3-OMe | H | H | CH=CH— CH=CH | |
| 59 | H | H | 4-OH | 3-OMe | H | CH=CH— CH=CH | | H |
| 64 | Me | Me | 4-OH | 3-OMe | H | H | H | H |
| 99 | Me | Me | 4-OH | 3-OMe | H | H | CH=CH— CH=CH | |
| 65 | H | H | 4-OH | 3-OMe | H | H | H | Me |
| 100 | Me | Me | 4-OH | 3-OMe | H | H | H | Me |
| 49 | Me | H | 4-OH | 3-OMe | H | H | H | OMe |
| 66 | H | H | 4-OH | 3-OMe | H | H | H | OMe |
| 101 | H | H | 4-OH | 3-OMe | H | H | H | CN |
| 102 | H | H | 4-OH | 3-OMe | H | H | H | $C(CH_3)_3$ |
| 103 | H | H | 4-OH | 3-OMe | H | Me | H | H |
| 104 | H | H | 4-OH | 3-OMe | H | H | Me | H |
| 105 | H | H | 4-OH | 3-OMe | 6-Cl | H | CH=CH— CH=CH | |
| 106 | H | H | 4-OH | 3-OEt | H | H | H | H |

In the above formulae, Me = methyl, Et = ethyl, Bn = benzyl, Ph = phenyl and OTBDMS = tert-butyldimethylsilyloxy.

Compositions and Uses of Compounds of Formula I

The present invention thus enables and provides a method for treating or preventing hypersensitivity, smooth muscle disorders, spasmodic conditions, allergic conditions, inflammatory conditions and/or pain in a human or non-human animal.

Such conditions include, for example, asthma, cough, pruritus, food intolerance, psoriasis, croup, irritable bowel syndrome, tinnitus, Meniere's disease, stress-induced ulceration or acetylsalicylic acid-induced ulceration, primary dysmenorrhea, pre-term labour, pre-term contractions, diarrhoea, gastrointestinal cramps, diverticular disease, achalasia, Hirschsprung's disease, gastro-oesophageal reflux disease, myotonic dystrophy, gallstone disease, constipation, post-surgical gastroparesis syndrome, paralytic ileus, post-operative ileus, diabetic gastroparesis, bowel paresis, intestinal pseudo-obstruction, peripheral arterial diseases, Raynaud's syndrome and coronary artery spasm, angina, peripheral arterial disease, hypertension, hypotension, vascular paresis and other vascular disorders, bladder disorders, nausea, allergic rhinitis, allergic dermatitis, inflammation, inflammatory bowel disease, ileitis, pancreatitis, cholecystitis, non-allergic rhinitis, oesophagitis, osteoarthritis, rheumatoid arthritis, Huntington's disease, cerebral ischemia, acute inflammatory pain, neuropathic pain, visceral pain, dental pain and headaches. The compounds are also useful, for example, in the maintenance of normal gut function, as a calmative for the gut, to maintain normal breathing, to ease motion sickness and vertigo, to soothe sore throats and coughs, to ease nausea and vomiting, as an aid to maintain normal digestion, to ease upset stomachs, to warm hands and feet, to aid normal menstruation, to maintain normal blood pressure, to normalise bowel movement, to maintain a healthy immune system, to aid in the recovery from colds and flu, as a decongestant, to soothe headaches, to relieve muscle soreness, to ease mild aches and pains, to provide relief from toothache, to provide relief from mouth ulcers, to maintain healthy joints, to help limit cellulite occurrence and as an aid to weight loss.

The active agent according to the present invention may be administered in the form of a composition comprising the active agent and any suitable additional component. The composition may, for example, be a pharmaceutical composition (medicament). The composition may alternatively, for example, be a foodstuff, food supplement, beverage or beverage supplement. The composition is preferably adapted for oral administration, although all other administration routes are possible too, particularly, inhalation, parenteral (e.g. injection, implantation or infusion), topical, transdermal, rectal and vaginal.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations. Techniques and formulations generally may be found in Remington, The Science and Practice of Pharmacy, Mack Publishing Co., Easton, Pa., latest edition.

Solid compositions preferably contain from 5 or 10 to about 70 percent by weight of the active ingredient.

Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions suitable for oral use can be prepared by dissolving the active component in water and adding suitable colourants, flavours, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container or apparatus. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavourings, colourants, stabilizers, buffers, artificial and natural sweeteners, dispersants, thickeners, solubilising agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

The terms "foodstuff", "food supplement", "beverage" and "beverage supplement" used herein have the normal meanings for those terms, and are not restricted to pharmaceutical preparations. Other composition forms are also included within the present invention. These may, for example, include pure or substantially pure compound as such, a foodstuff precursor such as a rehydratable powder or a beverage precursor such as a powder dispersible in water, milk or other liquid.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound of formula I will, of course, vary with the nature of the severity of the condition to be treated and with the particular compound of formula I and its route of administration. The selection of appropriate dosages is within the ability of one of ordinary skill in this art, without undue burden. In general, the daily dose range may be from about 10 µg to about 30 mg per kg body weight of a human and non-human animal, preferably from about 50 µg to about 30 mg per kg of body weight of a human and non-human animal, for example from about 50 µg to about 10 mg per kg of body weight of a human and non-human animal, for example from about 100 µg to about 30 mg per kg of body weight of a human and non-human animal, for example from about 100 µg to about 10 mg per kg of body weight of a human and non-human animal and most preferably from about 100 µg to about 3 mg per kg of body weight of a human and non-human animal.

For human use, the dosage may conveniently be between about 0.1 mg and about 2 g per day, for example between about 0.1 mg and about 1 g per day, preferably between about 1 mg and about 200 mg per day according to the particular application and the potency of the active ingredient.

In addition to one or more compound of general formula I, the compositions can also contain other active ingredients, such as cyclooxygenase inhibitors, non-steroidal anti-inflammatory drugs (SAIDs), peripheral analgesic agents such as diflunisal and the like. The weight ratio of the compound of the formula I to the second active ingredient may be varied and will depend upon the effective dose of each ingredient. Generally, an effective dose of each will be used. Thus, for example, when a compound of the formula I is combined with an NSAID, the weight ratio of the compound of the formula I to the NSAID will generally range from about 1000:1 to about 1:1000, preferably about 200:1 to about 1:200. Combinations of a compound of the general formula I and other active ingredients will generally also be within the aforementioned range, but in each case, an effective dose of each active ingredient should be used. Pharmaceutical compositions comprising the formula I compounds may also contain, as the second active ingredient, antihistamine agents such as cetirizine, diphenhydrinate, chlorpheniramine, promethazine and the like. Alternatively, they may include prostaglandin antagonists such as those disclosed in European Patent Application 11,067 or thromboxane antagonists such as those disclosed in U.S. Pat. No. 4,237,160. They may also contain histidine decarboxylase inhibitors such as α-fluoromethyl-histidine, described in U.S. Pat. No. 4,325,961. The compounds of the formula I may also be advantageously combined with an $H_1$ or $H_2$-receptor antagonist, such as for instance cimetidine, ranitidine, famotidine, temelastine, acrivastine, loratadine, cetrizine, tazifylline, azelastine, aminothiadiazoles disclosed in EP 81102976.8 and like compounds, such as those disclosed in U.S. Pat. Nos. 4,283,408; 4,362,736; 4,394,508 and European Patent Application No. 40,696. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

Discussion of Biological Test Data

Modulation of the TRPV1 receptor and/or modulation of smooth muscle tone and/or anti-remodelling and/or anti-inflammatory activity may be therapeutic (including prophylactic) or non-therapeutic. A therapeutic use of the method will typically comprise the treatment or prevention of a disease or disorder from which the human or non human animal is suffering or to which it is susceptible, such as, for example, hypersensitivity, smooth muscle disorders, spasmodic conditions, allergic conditions, inflammatory conditions and/or pain.

The TRPV1 receptor is a modestly calcium-selective ion channel and a member of the transient receptor potential family of ion channels. The TRPV1 receptor functions as a polymodal nociceptor sensitive to signals such as heat, lipoxygenase products and protons, and exogenous compounds such as capsaicin. It is known that modulation (agonist and antagonist) of the TRPV1 receptor has been exploited to treat a variety of conditions such as certain types of pain (Robbins, W., *Clin. J. Pain*, S86-S89, 16(2 Suppl), (2000); Rami, H. K. et al., *Drug Discov. Today*, 97-104, 1(1), (2004)).

The compounds described herein demonstrate effectiveness as good controllers of hypersensitivity, smooth muscle disorders, spasmodic conditions, allergic conditions, inflammatory conditions and/or pain in that they show modulation of some or all of the TRPV1 receptor, modulation of smooth muscle tone, inhibition of tissue remodelling, and inhibition of inflammatory mediator production. This group of compounds represents a new series of agents which have potential therapeutic benefit in treating or preventing hypersensitivity, smooth muscle disorders, spasmodic conditions, allergic conditions, inflammatory conditions and/or pain in a human or non-human animal.

Preparation of the Compounds

Reduction of Compounds of Formula II

The preparative method of the eighth aspect of the present invention involves selectively reducing the aliphatic carbon-carbon double bond in a compound of general formula II, to obtain the compound of general formula I.

Examples of the method, for the preparation of compounds 3 and 2 from compounds 35 and 34 respectively, are shown below in Reaction Schemes 1 and 2.

Another example of the method, for the preparation of compound 69 from compound 68, is shown below in Reaction Scheme 3.

The process is essentially a selective catalytic reduction of the 5-(4-hydroxy-3-methoxyphenyl)-1,3-dioxoalkenyl compound of formula II in the presence of hydrogen gas using either palladium on carbon or Raney nickel as catalyst. When palladium on carbon is used as catalyst, the reaction is preferably carried out in a suitable organic solvent such as a mixture of toluene and pyridine.

The catalytic selective reduction of the carbon-carbon double bond in the compounds of general formula II is a well-known synthetic step in organic chemistry, which will be readily achievable by the skilled worker. As a result, detailed discussion is not required here.

Condensation of a Benzaldehyde with a β-diketone

The preparative method of the ninth aspect of the present invention preferably includes condensing a benzaldehyde compound of general formula III as defined above with a β-diketone compound of general formula IV as defined above, in the presence of a chelating agent to deactivate the carbon between the two carbonyl groups in formula IV in favour of the terminal methyl carbon atom, to obtain the compound of general formula II.

For a discussion of the conditions required for this reaction, see, for example, U.S. Pat. No. 4,761,503, the disclosure of which is incorporated herein by reference. The chelating agent may for example, be a boron or transition metal Lewis acid, by which is meant a chemical compound comprised of a central boron or transition metal atom and appropriate ligands, such that the central boron or metal atom can form chemical complexes by interaction with electron-rich atoms of other compounds.

Examples of such chelating agents are boron trioxide and titanium tetrachloride. For further details of synthetic methods using titanium tetrachloride, see (1) B. Weidmann and D. Seebach, *Angew. Chem. Int. Ed. Engl.* 22, 31-45 (1983) or (2) M. T. Reetz, "Organotitanium Reagents in Organic Synthesis. A Simple Means to Adjust Reactivity and Selectivity of Carbanions" in *Top. Curr. Chem.* 106, 1-54 (1982) or (3) T. Mukaiyama, *Angew. Chem. Int. Ed. Engl.* 16, 817-826 (1977), the disclosures of which are incorporated herein by reference.

Suitable solvents for the reaction include alkanes, cycloalkanes, ethers, cyclic ethers such as tetrahydrofuran, aromatic hydrocarbons, and halocarbons such as chloroform, dichloromethane or ethylene dichloride.

Co-ligands such as organic amines may also be present, as described in more detail in the US Patent mentioned above.

As also shown in Reaction Schemes 1 and 2, the 5-(4-hydroxy-3-methoxyphenyl)-1,3-dioxoalkenyl compound of formula II ($R_1$=$R_2$=H) can itself be synthesised by (1) first preparing the imidazole derivative of the appropriate carboxylic acid (e.g. by reacting the carboxylic acid with carbodiimidazole (CDI) in a suitable solvent such as tetrahydrofuran (THF)) and then reacting the imidazole product with 4-(4-hydroxy-3-methoxyphenyl)-but-3-en-2-one in the presence of base (for example, lithium hexamethyldisilazide (LHDMS)) in a suitable solvent such as THF (Reaction Scheme 1), or (2) first preparing the appropriate 2,4-diketone (e.g. by reacting a ketone of formula $CH_3$—CO—$R_3$ with ethyl acetate (EtOAc) in the presence of sodium hydride) and then reacting the 2,4-diketone product with 4-hydroxy-3-methoxybenzaldehyde in a boron-mediated coupling reaction (boron trioxide ($B_2O_3$) and tri-n-butyl borate ($(BuO)_3B$) in the presence of ethyl acetate (EtOAc) and butylamine ($BuNH_2$) (Reaction Scheme 2).

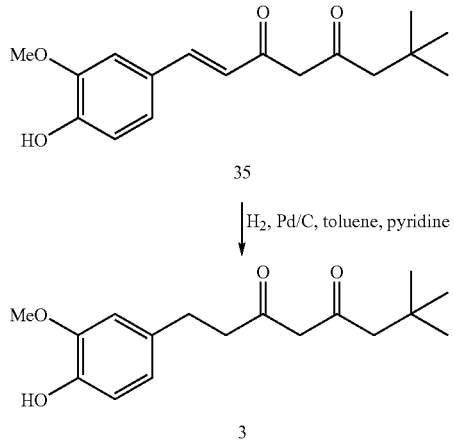

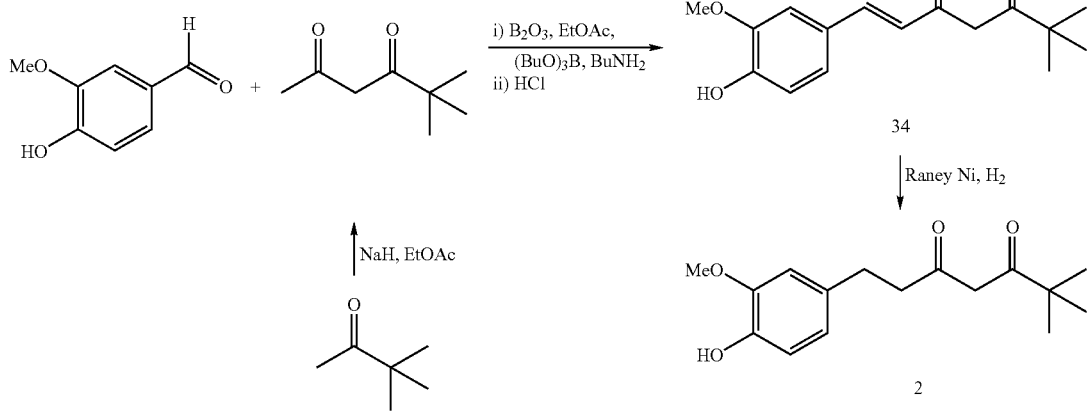

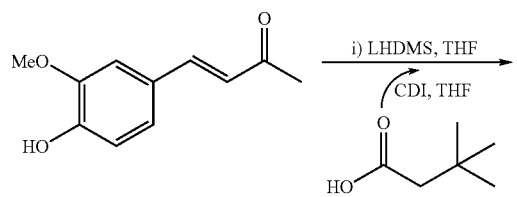

Alkylation Between the Ketone Groups

In accordance with the twelfth aspect of the present invention, compounds of formulae I or II which have an alkyl functionality at the central carbon between the two ketone groups or their tautomers can be produced by alkylation of the corresponding unalkylated compound (Reaction Scheme 3).

The starting material (e.g. compound 68 as shown in Reaction Scheme 3) is initially treated with sodium hydride (NaH) and trimethylsilyl chloride (TMSCl) in a suitable solvent such as tetrahydrofuran (THF). Subsequently an alkylating agent such as an alkyl iodide (e.g. methyl iodide (MeI) as shown in Reaction Scheme 3) is used in the presence of a base such as potassium carbonate.

The starting material 68 can, of course, also be selectively reduced analogously to the final stage of Reaction scheme 1. This option is also shown in Reaction Scheme 3, for completeness.

Reaction Scheme 3

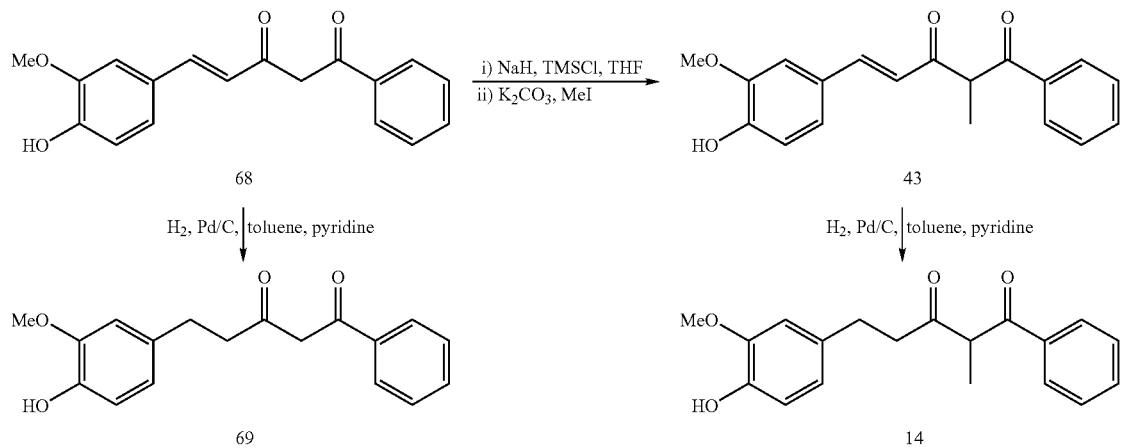

Reaction of Imidazole and Ketone

In accordance with the thirteenth aspect of the present invention, the compounds of general formulae I or II which have an alkyl functionality at the central carbon between the two ketone groups (or their tautomers) can alternatively be produced by reaction of, for example, a 5-(4-hydroxy-3-methoxyphenyl)pent-4-en-3-one with the imidazole derivative of a carboxylic acid in the presence of base, analogously to the preparation of the compounds of general formula II as illustrated in Reaction Scheme 1.

The compound thus prepared may be recovered from the reaction mixture by conventional means.

Salts, Complexes and Prodrugs

See the discussion under these separate headings in connection with the compounds of formulae I and II above.

BRIEF DESCRIPTION OF THE DRAWING

The accompanying drawing, identified as FIG. 1, shows the results of the experimental work reported in Example 68. In the FIGURE, the effects of compound 2, compound 32, budesonide and montelukast on enhanced pause (penH) in the test animals is shown.

EXAMPLES

Figure 1:
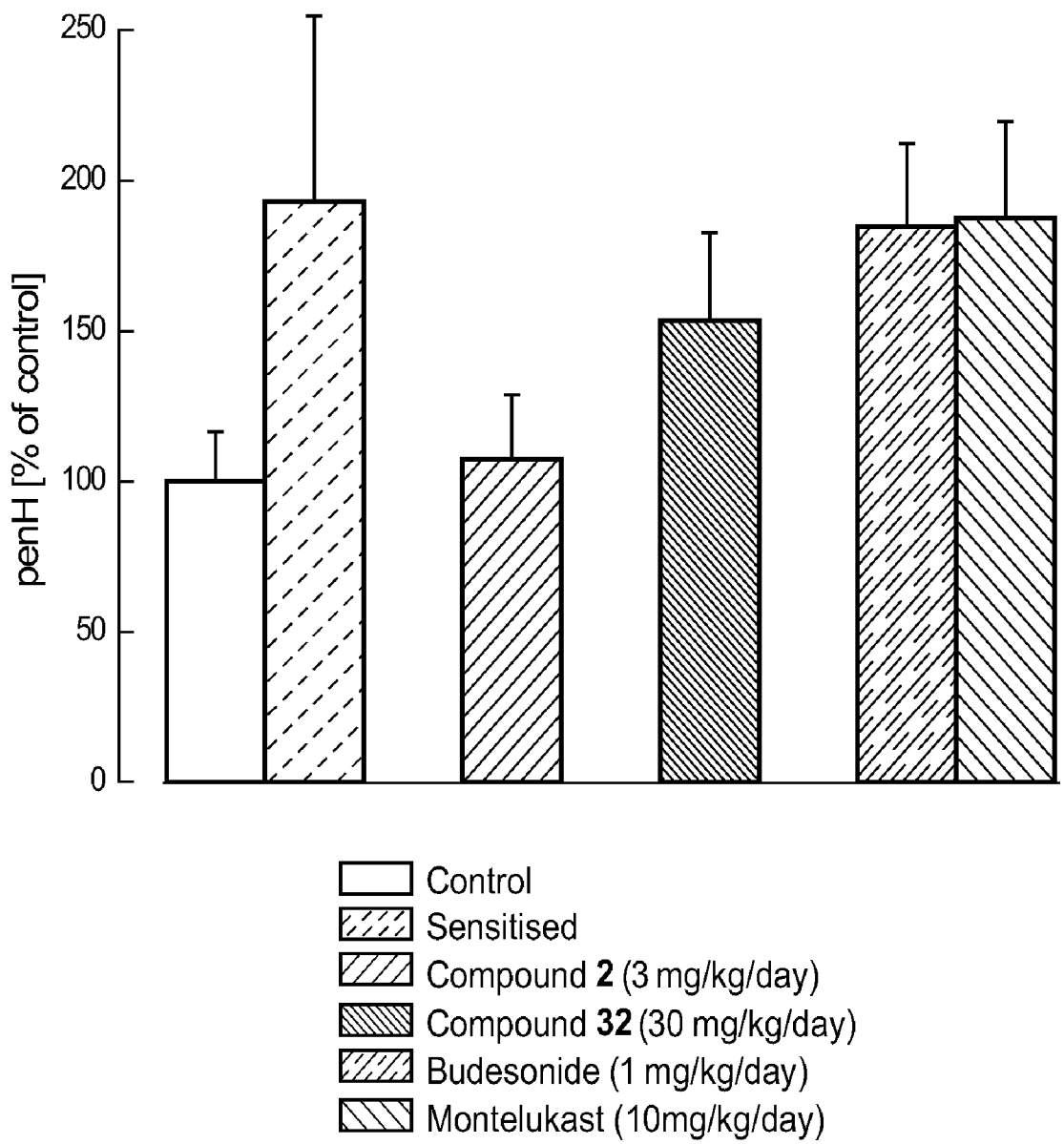

In the following non-limiting Examples of the present invention, the following abbreviations are used: g=grams; mol=moles; M=molar; ml=millilitres; l=litres; min=minute(s); h=hour(s); aq=aqueous; anh=anhydrous; atm=atmosphere (pressure); LHMDS=lithium hexamethyldisilazide; RT=room temperature; EFS=electrical field stimulation; THF=tetrahydrofuran; TBAF=tetrabutylammonium fluoride; TLC=thin layer chromatography; HPLC=high performance liquid chromatography; LRMS=low resolution mass spectrometry; LCMS=HPLC mass spectrometry; NMR=nuclear magnetic resonance; DMF=dimethylformamide. Abbreviations and symbols used in the NMR data follow the established convention. Percentages are by weight unless stated otherwise.

For each compound prepared in the synthesis Examples 1 to 60, the compound number allocated in the previous description has been indicated. These compound numbers are used to identify the compounds in the biological Examples 61 to 68. Many of the compounds exist in enol form in solution, as indicated by the NMR spectrum.

Example 1

(E)-1-(4-Hydroxy-3-methoxylphenyl)-6,6-dimethyl-hept-1-ene-3,5-dione (Compound 34)

5,5-Dimethylhexane-2,4-dione (2.84 g, 0.02 mol, prepared by reaction of pinacolone with ethyl acetate in the presence of sodium hydride), boron oxide (1.00 g, 0.014 mol) and dry ethyl acetate (20 ml) were stirred and heated at 40° C. for 30 min under $N_2$. To this solution of the boron complex was added 4-hydroxy-3-methoxybenzaldehyde (vanillin, 3.04 g, 0.02 mol) and tri-n-butyl borate (9.21 g, 10.8 ml, 0.04 mol). After stirring for 30 min, a solution of n-butylamine (1.10 g, 0.015 mol) in dry ethyl acetate (5 ml) was then added dropwise over 15 min. Stirring was continued at 40° C. for 24 h. Dilute hydrochloric acid (15 ml of 1.2 M) was added and the mixture rapidly stirred at 40° C. for 1 h, cooled to room temperature and filtered. The solid was washed with ethyl acetate (50 ml), adding the washings to filtrate. The aqueous layer was separated and extracted with ethyl acetate (100 ml). The organic phases were combined and washed with water (50 ml), then with several portions of saturated $NaHCO_{3\ (aq)}$, then water and dried over $MgSO_{4\ (anh)}$. Filtration and evaporation of the solvent in vacuo gave an orange-yellow oil (12.4 g). This oil was dissolved in a small amount of dichloromethane and the solution passed through a silica gel pad, eluting with further portions of dichloromethane. Combination of fractions judged pure by TLC ($R_f$ 0.5) afforded (E)-1-(4-hydroxy-3-methoxyphenyl) 6,6-dimethyl-hept-1-ene-3,5-dione (3.10 g, 56%) as an orange-yellow oil: $^1H$ NMR (500 MHz, $CDCl_3$) δ 1.20 (9H, s, $C(CH_3)_3$), 3.93 (3H, s, $OCH_3$), 5.77 (1H, s, H-4), 5.93 (1H, brs, OH), 6.39 (1H, d, J=15.8 Hz, H-2), 6.92 (1H, d, J=8.2 Hz, H-5'), 7.02 (1H, d, J=1.7 Hz, H-2'), 7.08 (1H, dd, J=8.2, 1.7 Hz, H-6'), 7.53 (1H, d, J=15.8 Hz, H-1), 15.8 (1H, s, OH) ppm; TLC $R_f$=0.5 (silica, dichloromethane). The NMR spectrum indicates that this com-

Example 2

(E)-1-(4-Hydroxy-3-methoxyphenyl)-6-methyl-hept-1-ene-3,5-dione (Compound 33)

By a similar procedure as described in Example 1 using 5-methylhexane-2,4-dione in place of 5,5-dimethylhexane-2,4-dione, (E)-1-(4-hydroxy-3-methoxyphenyl)-6-methyl-hept-1-ene-3,5-dione) (0.85 g, 16%) was obtained as a yellow-tan solid with no defined melting point: LRMS m/z 262 (M$^+$); $^1$H NMR (500 MHz, CDCl$_3$) δ 1.18 (6H, d, J=6.9 Hz, C(CH$_3$)$_2$), 2.56 (1H, heptet, J=6.9 Hz, CH, H-6), 3.93 (3H, s, OCH$_3$), 5.65 (1H, s, H-4), 5.94 (1H, brs, OH), 6.36 (1H, J=15.8 Hz, H-2), 6.92 (1H, d, J=8.2 Hz, H-5'), 7.02 (1H, d, J=1.6 Hz, H-2"), 7.08 (1H, dd, J=8.2, 1.6 Hz, H-6"), 7.52 (1H, d, J=15.8 Hz, H-1), 15.6 (1H, brs, OH) ppm. HPLC analysis indicated a purity of 98.3%.

Example 3

(E)-5-(4-Hydroxy-3-methoxyphenyl)-1-phenyl-pent-4-ene-1,3-dione (Compound 68)

By a similar procedure as described in Example 1 using 1-phenyl-1,3-butanedione in place of 5,5-dimethylhexane-2,4-dione, (E)-5-(4-hydroxy-3-methoxyphenyl)-1-phenyl-pent-4-ene-1,3-dione (1.78 g, 30%) was obtained as yellow needles: mp 159-161.5° C.; LRMS m/z 296 (M$^+$);

$^1$H NMR (500 MHz, CDCl$_3$) δ 3.94 (3H, s, OCH$_3$), 5.89 (1H, brs), 6.32 (1H, s, OH), 6.52 (1H, d, J=15.7 Hz, H-4), 6.94 (1H, d, J=8.2 Hz, H-5'), 7.06 (1H, brs, H-2'), 7.13 (1H, brd, J=8.2 Hz, H-6'), 7.47 (2H, brt, J=7.3 Hz, H-3", H-5"), 7.54 (1H, brt, J=7.2 Hz, H-4"), 7.63 (1H, d, J=15.7 Hz, H-5), 7.95 (2H, d, J=7.3 Hz, H-2", H-6") ppm; TLC R$_f$=0.3 (silica, dichloromethane); HPLC R$_t$ 6 min, 99.7% purity.

Example 4

(E)-1-Cyclopropyl-5-(4-hydroxy-3-methoxyphenyl)-pent-4-ene-1,3-dione (Compound 37)

By a similar procedure as described in Example 1 using 1-cyclopropylbutane-1,3-dione in place of 5,5-dimethylhexane-2,4-dione, (E)-1-cyclopropyl-5-(4-hydroxy-3-methoxyphenyl)-pent-4-ene-1,3-dione (0.38 g, 7%) was obtained as a yellow solid: mp 74.5-79° C.; LRMS m/z 260 (M$^+$); $^1$H NMR (500 MHz, CDCl$_3$) δ 0.94 (2H, m, cycloCH$_2$), 1.13 (2H, m, cycloCH$_2$), 1.76 (1H, m, cycloCH), 3.92 (3H, s, OCH$_3$), 5.72 (1H, s, H-2), 5.98 (1H, brs, OH), 6.31 (1H, d, J=15.8 Hz, H-4), 6.91 (1H, d, J=7.8 Hz, H-5'), 7.00 (1H, brs, H-2'), 7.06 (1H, brd, J=7.8 Hz, H-6'), 7.49 (1H, d, J=15.8 Hz, H-5), 15.4 (1H, brs, OH) ppm. HPLC analysis indicated a purity of 98.4%.

Example 5

(E)-5-(4-Hydroxy-3-methoxylphenyl)-1-(1-methylcyclopropyl)-pent-4-ene-1,3-dione (Compound 38)

By a similar procedure as described in Example 1 using 1-(1-methylcyclopropyl)butane-1,3-dione in place of 5,5-dimethylhexane-2,4-dione, (E)-5-(4-hydroxy-3-methoxyphenyl)-1-(1-methylcyclopropyl)-pent-4-ene-1,3-dione (3.12 g, 34%) was obtained as yellow crystals: mp 78-80° C.; LRMS m/z 274 (M$^+$); $^1$H NMR (500 MHz, CDCl$_3$) δ 0.78 (2H, m, cyclopropyl CH$_2$), 1.33 (2H, m, cyclopropylCH$_2$), 1.36 (3H, s, CH$_3$), 3.93 (3H, s, OCH$_3$), 5.71 (1H, s, H-2), 5.87 (1H, brs, OH), 6.36 (1H, d, J=15.8 Hz, H-4), 6.92 (1H, d, J=8.2 Hz, H-5'), 7.02 (1H, d, J=1.8 Hz, H-2'), 7.08 (1H, dd, J=8.2, 1.8 Hz, H-6'), 7.51 (1H, d, J=15.8 Hz, H-5), 15.9 (1H, brs, OH) ppm; TLC R$_f$=0.75 (ethyl acetate-hexane, 1:1). HPLC analysis indicated a purity of 97.1%.

Example 6

(E)-1-(4-Hydroxy-3-methoxyphenyl)-6-methyl-oct-1-ene-3,5-dione (Compound 41)

By a similar procedure as described in Example 1 using 5-methylheptane-2,4-dione in place of 5,5-dimethylhexane-2,4-dione, (E)-1-(4-hydroxy-3-methoxyphenyl)-6-methyl-oct-1-ene-3,5-dione (350 mg, 1.27 mmol, 2%) was obtained as an orange oil: $^1$H NMR (400 MHz, CDCl$_3$) δ 0.91 (3H, t, J=7.2 Hz, CH$_3$), 1.15 (3H, d, J=7.2 Hz, CH$_3$), 1.41-1.49 (1H, m, H-7) and 1.63-1.72 (1H, m, H-7), 2.29-2.38 (1H, m, H-6), 3.91 (3H, s, OCH$_3$), 5.62 (1H, s, H-4), 6.35 (1H, d, J=15.6 Hz, H-2), 6.90 (1H, d, J=8.4 Hz, H-5'), 7.00 (1H, d, J=2.0 Hz, H-2'), 7.07 (1H, dd, J=8.4, 2.0 Hz, H-6'), 7.52 (1H, d, J=15.6 Hz, H-1), 15.64 (1H, s, OH) ppm; $^{13}$C NMR (100 MHz, CDCl$_3$) δ 203.9, 178.6, 147.8, 146.9, 139.9, 127.8, 122.7, 120.7, 114.9, 109.5, 99.4, 56.0, 45.6, 27.2, 17.2, 12.0 ppm.

Example 7

(E)-1,5-Bis-(4-hydroxy-3-methoxyphenyl)-pent-4-ene-1,3-dione (Compound 47)

By a similar procedure as described in Example 1 using 1-(4-hydroxy-3-methoxyphenyl)-butane-1,3-dione (prepared by reaction of 4-hydroxy-3-methoxyacetophenone with ethyl acetate in the presence of sodium hydride) in place of 5,5-dimethylhexane-2,4-dione, (E)-1,5-bis-(4-hydroxy-3-methoxyphenyl)-pent-4-ene-1,3-dione (920 mg, 39%) was obtained as yellow needles: mp 170-172° C.; LRMS m/z 342 (M$^+$); $^1$H NMR (500 MHz, CDCl$_3$) δ 3.95 (3H, s, OCH$_3$), 3.98 (3H, s, OCH$_3$), 5.85 (1H, brs, OH), 6.04 (1H, brs, OH), 6.26 (1H, s, H-2), 6.48 (1H, d, J=15.7 Hz, H-4), 6.94 (1H, d, J=7.2 Hz, H-5"), 6.97 (1H, d, J=8.3 Hz, H-5'), 7.05 (1H, brs, H-2"), 7.12 (1H, brd, J=8.3 Hz, H-6"), 7.51 (1H, brd, J=7.2 Hz, H-6'), 7.56 (1H, brs, H-2'), 7.60 (1H, J=15.7 Hz, H-5), 16.2 (1H, brs, OH) ppm; TLC R$_f$=0.5 (silica, dichloromethane); HPLC R$_t$ 14 min 99.6% purity.

Example 8

(E)-5-(4-Hydroxy-3-methoxyphenyl)-1-(4-iodophenyl)-pent-4-ene-1,3-dione (Compound 67)

By a similar procedure as described in Example 1 using 1-(4-iodophenyl)-butane-1,3-dione (prepared by reaction of 4-iodoacetophenone with ethyl acetate in the presence of sodium hydride) in place of 5,5-dimethylhexane-2,4-dione, (E)-5-(4-hydroxy-3-methoxyphenyl)-1-(4-iodophenyl)-pent-4-ene-1,3-dione (0.40 g, 0.95 mmol, 31%) was obtained pound exists mainly in the enol form in solution. A less pure fraction (1.16 g) was also isolated.

as a yellow solid: mp 139-141° C.; $^1$H NMR (400 MHz; CDCl$_3$) δ 3.95 (3H, s, OCH$_3$), 5.87 (1H, s, OH), 6.27 (1H, s, H-2), 6.42 (1H, d, J=16.0 Hz, H-4), 6.87 (1H, d, J=8.4 Hz, H-5'), 6.99 (1H, s, H-2'), 7.06 (1H, d, J=8.4 Hz, H-6'), 7.54-7.60 (3H, m, H-5, H-3", H-5"), 7.41-7.62 (2H, m, H-2", H-6"), 16.18 (1H, s, OH) ppm; $^{13}$C NMR (100 MHz; CDCl$_3$) δ 187.5, 180.8, 148.1, 146.9, 140.9, 138.0, 135.5, 128.9, 127.6, 123.2, 120.9, 115.1, 109.6, 100.0, 97.1, 56.0 ppm.

Example 9

(E)-6-(4-Hydroxy-3-methoxyphenyl)-1-phenyl-hex-5-ene-2,4-dione (Compound 60)

By a similar procedure as described in Example 1 using 1-phenylpentane-2,4-dione in place of 5,5-dimethylhexane-2,4-dione, (E)-6-(4-hydroxy-3-methoxyphenyl)-1-phenyl-hex-5-ene-2,4-dione (0.15 g, 2%) was obtained as a tan solid: mp 106° C.; LRMS m/z 310 (M$^+$); $^1$H NMR (500 MHz, CDCl$_3$) δ 3.42 (2H, s, CH$_2$Ph), 3.90 (3H, s, OCH$_3$), 5.40 and 6.33 (1H, s, H-3), 5.73 and 5.80 (1H, 2×brs, OH), 6.29 (1H, d, J=15.7 Hz, H-5), 6.79 (m), 6.88 (1H, d, J=8.1 Hz, H-5'), 6.99 (1H, s, H-2'), 7.03 (1H, brd, J=8.2 Hz, H-6'), 7.30 (2H, d, J=7.7 Hz, H-3", H-5"), 7.42-7.54 (4H, m, phenylH, H-6), 16.50 (1H, brs, OH) ppm; TLC R$_f$=0.6 (ethyl acetate-hexane, 1:1). The NMR spectrum was very complex and only a partial interpretation is given. The compound probably exists as a mixture of two enols and the keto form in solution. HPLC analysis indicated a purity of 93.7%.

Example 10

(E)-7,7-Dimethyl-1-(4-hydroxy-3-methoxyphenyl)-oct-1-ene-3,5-dione (Compound 35)

Solution A 1,1-Carbonyldiimidazole (1.69 g, 10.4 mmol) was added to a stirred solution of 3,3-dimethylbutyric acid (1.32 ml, 10.4 mmol) in dry THF (50 ml) under a nitrogen atmosphere. Stirring was continued for 18 h.

Solution B

A solution of 1-(4-hydroxy-3-methoxyphenyl)-but-1-ene-3-one (prepared by the method of Denniff, P., Macleod, I., and Whiting, D. A. *JCS Perkin I*. 82-87 (1979); 2.0 g, 10.4 mmol) in dry THF (20 ml) was added dropwise over 1.5 h to stirred LHMDS (20.8 ml, 1 M in hexane) with ice cooling under a nitrogen atmosphere. The orange suspension was allowed to warm to room temperature slowly overnight.

Solution A was then added dropwise over 30 min to solution B with ice cooling under a nitrogen atmosphere. Stirring was continued at low temperature for 3 h, and the solution then allowed to warm to room temperature slowly overnight. Ethyl acetate (50 ml) and dilute hydrochloric acid (50 ml, 2 M) were added and the mixture stirred for 10 min. The separated aqueous layer was extracted with ethyl acetate (2×100 ml) and the combined organic extracts dried (Na$_2$SO$_{4\ (anh)}$), filtered and evaporated in vacuo to leave an orange oily solid. Purification by column chromatography using ethyl acetate: petroleum ether (1:4) as eluent gave (E)-7,7-dimethyl-1-(4-hydroxy-3-methoxyphenyl)-oct-1-ene-3,5-dione (195 mg, 0.67 mmol, 6%) as a yellow solid: mp 130-132° C.; $^1$H NMR (400 MHz; CDCl$_3$) δ 1.03 (9H, s, C(CH$_3$)$_3$), 2.22 (2H, s, t-BuCH$_2$), 3.93 (3H, s, OCH$_3$), 5.57 (1H, s, H-4), 6.35 (1H, d, J=15.8 Hz, H-2), 6.91 (1H, d, J=8 Hz, H-6'), 7.01 (1H, s, H-2'), 7.04-7.10 (1H, m, H-6'), 7.54 (1H, d, J=15.8 Hz, H-1), 15.83 (1H, s, OH) ppm; $^{13}$C NMR (100 MHz; CDCl$_3$) δ 197.5, 179.6, 147.8, 146.8, 140.3, 127.8, 122.7, 121.1, 114.9, 109.5, 102.4, 56.1, 53.3, 31.1, 30.1 ppm.

Example 11

(E)-1-Cyclopentyl-5-(4-hydroxy-3-methoxyphenyl)-pent-4-ene-1,3-dione (Compound 40)

By a similar procedure as described in Example 10 using cyclopentanecarboxylic acid in place of 3,3-dimethylbutyric acid, (E)-1-cyclopentyl-5-(4-hydroxy-3-methoxyphenyl)-pent-4-ene-1,3-dione (200 mg, 0.69 mmol, 7%) was obtained as a yellow oily solid: $^1$H NMR (400 MHz; CDCl$_3$) δ 1.54-1.93 (8H, m, cyclopentyl CH$_2$), 2.78 (1H, quintet, J=8.4 Hz, cyclopentyl CH), 3.92 (3H, s, OCH$_3$), 5.63 (1H, s, H-2), 6.33 (1H, d, J=15.8 Hz, H-4), 6.87-6.92 (1H, m, H-5'), 7.00 (1H, s, H-2'), 7.07 (1H, d, J=8.1 Hz, H-6'), 7.50 (1H, d, J=15.8 Hz, H-5), 15.51 (1H, s, OH) ppm; $^{13}$C NMR (100 MHz; CDCl$_3$) δ 203.7, 177.5, 147.7, 146.9, 139.6, 127.9, 122.6, 120.6, 114.9, 109.5, 99.6, 56.0, 49.3, 30.3, 26.1 ppm.

Example 12

(E)-5-(4-Hydroxy-3-methoxyphenyl)-1-(1-methylcyclohexyl)-pent-4-ene-1,3-dione (Compound 42)

By a similar procedure as described in Example 10 using 1-methylcyclohexanecarboxylic acid in place of 3,3-dimethylbutyric acid, (E)-5-(4-hydroxy-3-methoxyphenyl)-1-(1-methyl-cyclohexyl)-pent-4-ene-1,3-dione (170 mg, 0.54 mmol, 4%) was obtained as an orange-coloured oil: $^1$H NMR (400 MHz; CDCl$_3$) δ 1.14 (3H, s, CH$_3$), 1.14-1.62 (10H, m, cyclohexyl CH$_2$), 3.84 (3H, s, OCH$_3$), 5.81 (1H, s, H-2), 6.45 (1H, d, J=15.8 Hz, H-4), 6.99 (1H, d, J=8.4 Hz, H-5'), 7.07-7.15 (2H, m, H-2', H-6'), 7.53 (1H, d, J=15.8 Hz, H-5), 15.73 (1H, s, OH) ppm; $^{13}$C NMR (100 MHz; CDCl$_3$) δ 207.7, 177.0, 175.8, 151.6, 141.6, 138.5, 134.0, 123.4, 121.0, 111.2, 97.8, 55.9, 45.1, 43.7, 35.5, 26.0, 23.0 ppm.

Example 13

(E)-1-(Biphenyl-4-yl)-5-(4-hydroxy-3-methoxyphenyl)-pent-4-ene-1,3-dione (Compound 50)

By a similar procedure as described in Example 10 using 4-biphenylcarboxylic acid in place of 3,3-dimethylbutyric acid, (E)-1-(biphenyl-4-yl)-5-(4-hydroxy-3-methoxyphenyl)-pent-4-ene-1,3-dione (0.979 g, 17%) was obtained as a yellow powdery solid: LCMS m/z 373 (MH$^+$); $^1$H NMR (400 MHz, CDCl$_3$) δ 3.97 (3H, s, OCH$_3$), 5.88 (1H, br s, H-2), 6.37 (1H, s, OH), 6.54 (1H, d, J=15.6 Hz, H-5), 6.96 (1H, d, J=8.4 Hz, H-5'), 7.08 (1H, d, J=1.6 Hz, H-2'), 7.15 (1H, dd, J=8.0, 1.6 Hz, H-6'), 7.39-7.50 (3H, m, 2×ArH, H-1), 7.64-7.72 (5H, m, 5×ArH), 8.04 (2H, d, J=8.4 Hz, 2×ArH) ppm; $^{13}$C NMR (100 MHz, CDCl$_3$) δ 187.91, 180.37, 147.82, 146.78, 145.11, 140.33, 139.92, 134.95, 128.91, 128.11, 127.79, 127.65, 127.22, 127.19, 122.86, 120.99, 114.82, 109.52, 97.24, 55.92 ppm.

Example 14

(E)-1-(Biphenyl-2-yl)-5-(4-hydroxy-3-methoxyphenyl)-pent-4-ene-1,3-dione (Compound 51)

By a similar procedure as described in Example 10 using 2-biphenylcarboxylic acid in place of 3,3-dimethylbutyric acid, (E)-1-(biphenyl-2-yl)-5-(4-hydroxy-3-methoxyphenyl)-pent-4-ene-1,3-dione (348 mg, 6%) was obtained as a yellow foamy solid: $^1$H NMR (400 MHz, CDCl$_3$) δ 3.92 (3H, s, OCH$_3$), 5.50 (1H, s, H-2), 5.90 (1H, brs, OH), 6.14 (1H, d, J=16.0 Hz, H-4), 6.91 (1H, d, J=8.0 Hz, H-5'), 6.96 (1H, d, J=2.0 Hz, H-2'), 7.03 (1H, dd, J=8.0, 2.0 Hz, H-6'), 7.36-7.48 (8H, m, 7×ArH, H-5), 7.53 (1H, td, J=8.0, 2.0 Hz, ArH), 7.73 (1H, brd, J=8.0 Hz, ArH) ppm; $^{13}$C NMR (100 MHz, CDCl$_3$) δ 193.54, 177.84, 147.66, 146.69, 140.74, 139.89, 137.56, 130.67, 129.07, 128.77, 128.36, 127.60, 127.49, 127.39, 122.62, 120.53, 114.73, 109.48, 102.55, 55.90 ppm.

Example 15

(E)-1-(4-Fluorophenyl)-5-(4-hydroxy-3-methoxyphenyl)-pent-4-ene-1,3-dione (Compound 52)

By a similar procedure as described in Example 10 using 4-fluorobenzoic acid in place of 3,3-dimethylbutyric acid, (E)-1-(4-fluorophenyl)-5-(4-hydroxy-3-methoxyphenyl)-pent-4-ene-1,3-dione (3.16 g, 47%) was obtained as a yellow powdery solid: $^1$H NMR (400 MHz, CDCl$_3$) δ 3.95 (3H, s, OCH$_3$), 5.95 (1H, brs, H-2 or phenol OH), 6.27 (1H, s, OH), 6.50 (1H, d, J=16.0 Hz, H-4), 6.95 (1H, d, J=8.0 Hz, ArH), 7.05 (1H, d, J=2.0 Hz, ArH), 7.12-7.17 (4H, m, 4×ArH), 7.63 (1H, d, J=16.0 Hz, H-5), 7.94-7.99 (2H, m, 2×ArH) ppm; $^{13}$C NMR (100 MHz, CDCl$_3$) δ 55.90, 96.86, 109.53, 114.83, 115.59, 115.81, 120.64, 127.56, 129.62, 129.71, 132.58, 140.42, 146.78, 147.86, 164.09, 166.61, 179.87, 187.59 ppm.

Example 16

Methyl 4-[(E)-1,3-dioxo-5-(4-hydroxy-3-methoxyphenyl)pent-4-enyl]benzoate (Compound 57)

By a similar procedure as described in Example 10 using monomethyl terephthalate in place of 3,3-dimethylbutyric acid, methyl 4-[(E)-1,3-dioxo-5-(4-hydroxy-3-methoxyphenyl)-pent-4-enyl]benzoate (0.22 g, 3%) was obtained as a yellow solid: mp 187-189° C.; LRMS m/z 354 (M$^+$); $^1$H NMR (500 MHz, CDCl$_3$) δ 3.96 (6H, s, 2×OCH$_3$), 5.89 (1H, brs, OH), 6.35 (1H, s, H-2), 6.53 (1H, d, J=15.8 Hz, H-4), 6.95 (1H, d, J=8.2 Hz, H-5'), 7.07 (1H, brs, H-2'), 7.14 (1H, brd, J=8.2 Hz, H-6'), 7.67 (1H, d, J=15.8 Hz, H-5), 7.99 (1H, d, J=8.1 Hz, H-2", H-6"), 8.13 (1H, d, J=8.1 Hz, H-3", H-5"), 16.20 (1H, brs, OH) ppm; TLC R$_f$=0.5 (ethyl acetate-hexane, 1:1).

Example 17

(E)-5-(4-Hydroxy-3-methoxyphenyl)-1-(naphthalene-2-yl)-pent-4-ene-1,3-dione (Compound 58)

By a similar procedure as described in Example 10 using 2-naphthoic acid in place of 3,3-dimethylbutyric acid, (E)-5-(4-hydroxy-3-methoxyphenyl)-1-(naphthalene-2-yl)-pent-4-ene-1,3-dione (2.77 g, 46%) was obtained as a yellow powdery solid: $^1$H NMR (400 MHz, CDCl$_3$) δ 3.97 (3H, s, OCH$_3$), 5.90 (1H, br s, OH), 6.49 (1H, s, H-2), 6.57 (1H, d, J=16.0 Hz, H-4), 6.96 (1H, d, J=8.4 Hz, H-5'), 7.09 (1H, d, J=2.0 Hz, H-2'), 7.16 (1H, dd, J=8.0, 2.0 Hz, H-6'), 7.54-7.62 (2H, m, 2×ArH), 7.67 (1H, d, J=16.0 Hz, H-5), 7.88-7.93 (2H, m, 2×ArH), 7.97 (1H, d, J=8.0 Hz, ArH), 8.00 (1H, dd, J=8.0, 2.0 Hz, ArH), 8.51 (1H, brs, ArH) ppm; $^{13}$C NMR (100 MHz, CDCl$_3$) δ 188.22, 180.39, 147.83, 146.78, 140.38, 135.28, 133.51, 132.69, 129.37, 128.41, 128.10, 127.75, 127.68, 126.72, 123.36, 122.90, 121.02, 114.82, 109.49, 97.55, 55.93 ppm.

Example 18

(E)-5-(4-Hydroxy-3-methoxylphenyl)-1-(naphthalene-1-yl)-pent-4-ene-1,3-dione (Compound 59)

By a similar procedure as described in Example 10 using 1-naphthoic acid in place of 3,3-dimethylbutyric acid, (E)-5-(4-hydroxy-3-methoxyphenyl)-1-(naphthalene-1-yl)-pent-4-ene-1,3-dione (1.21 g, 20%) was obtained as a yellow foamy solid: $^1$H NMR (400 MHz, CDCl$_3$) δ 3.96 (3H, s,), 5.88 (1H, brs, OH), 6.19 (1H, s, H-2), 6.50 (1H, d, J=15.6 Hz, H-4), 6.95 (1H, d, J=8.4 Hz, H-5'), 7.08 (1H, d, J=1.6 Hz, H-2'), 7.15 (1H, dd, J=8.0, 1.6 Hz, H-6'), 7.51-7.62 (3H, m, 3×ArH), 7.67 (1H, d, J=15.6 Hz, H-5), 7.80 (1H, dd, J=7.0, 1.0 Hz, ArH), 7.91 (1H, d, J=8.0 Hz, ArH), 7.98 (1H, d, J=8.0 Hz, ArH), 8.55 (1H, d, J=8.4 Hz, ArH), 16.11 (1H, brs, OH) ppm; $^{13}$C NMR (100 MHz, CDCl$_3$) δ 193.36, 179.19, 147.85, 146.78, 140.43, 135.74, 133.83, 131.70, 130.10, 128.47, 127.63, 127.25, 126.94, 126.35, 125.69, 124.74, 122.91, 120.60, 114.82, 109.48, 102.01, 55.94 ppm.

Example 19

(E)-5-(4-Hydroxy-3-methoxyphenyl)-1-p-tolyl-pent-4-ene-1,3-dione (Compound 65)

By a similar procedure as described in Example 10 using p-toluic acid in place of 3,3-dimethylbutyric acid, (E)-5-(4-hydroxy-3-methoxyphenyl)-1-p-tolyl-pent-4-ene-1,3-dione (2.1 g, 13%) was obtained as a yellow solid: LRMS (m/z) 311 (MH$^+$); $^1$H NMR (300 MHz, CDCl$_3$) δ 2.40 (3H, s, ArCH$_3$), 3.92 (3H, s, OCH$_3$), 6.29 (1H, s, H-2), 6.49 (1H, d, J=15.6 Hz, H-4), 6.92 (1H, d, J=8.7 Hz, H-5'), 7.03 (1H, d, J=1.8 Hz, H-2'), 7.10 (1H, dd, J=8.1, 1.8 Hz, H-6'), 7.25 (2H, d, J=7.8 Hz, ArH), 7.60 (1H, d, J=15.3 Hz, H-5), 7.84 (2H, d, J=8.1 Hz, ArH), 16.32 (1H, s, OH) ppm; $^{13}$C NMR (100 MHz, CDCl$_3$) δ 21.62, 55.90, 97.01, 109.47, 114.79, 121.09, 122.76, 127.30 (2×CH), 127.70, 129.32 (2×CH), 133.57, 139.97, 143.21, 146.76, 147.72, 179.81, 188.62 ppm.

Example 20

(E)-5-(4-Hydroxy-3-methoxylphenyl)-1-(4-methoxylphenyl)-pent-4-ene-1,3-dione (Compound 66)

By a similar procedure as described in Example 10 using 4-methoxybenzoic acid in place of 3,3-dimethylbutyric acid, (E)-5-(4-hydroxy-3-methoxyphenyl)-1-(4-methoxyphenyl)-pent-4-ene-1,3-dione (1.22 g, 7%) was obtained as a yellow solid: LRMS (m/z) 327 (MH$^+$); $^1$H NMR (300 MHz, CDCl$_3$) δ 3.87 (3H, s, OCH$_3$), 3.93 (3H, s, OCH$_3$), 5.92 (1H, brs, OH), 6.25 (1H, s, H-2), 6.47 (1H, d, J=15.9 Hz, H-4), 6.93-6.94 (3H, m, ArH), 7.04 (1H, d, J=1.8 Hz, H-2'), 7.11 (1H, dd, J=8.1, 1.5 Hz, H-6'), 7.58 (1H, d, J=15.6 Hz, H-5), 7.92 (2H, d, J=9 Hz, ArH), 16.32 (1H, s, OH), ppm.

Example 21

(E)-5-(4-Hydroxy-3-methoxyphenyl)-2-methyl-1-phenyl-pent-4-ene-1,3-dione (Compound 43)

Compound 68 (1.0 g, 3.38 mmol) was added to a stirred suspension of sodium hydride (81 mg, 135 mg of 60%, 3.38 mmol) in anhydrous THF (25 ml) under $N_2$. The mixture was stirred at room temperature for 15 min, then trimethylsilyl chloride (0.43 ml, 367 mg, 3.38 mmol) was added and the reaction heated at 55° C. for 1 h. The mixture was cooled to 25° C., then potassium carbonate (505 mg, 3.66 mmol) was added and the reaction stirred for 45 min. After cooling in an ice-bath to 0° C., a solution of methyl iodide (0.31 ml, 4.64 mmol) in anhydrous THF (3 ml) was added and the mixture heated at reflux for 5 h. Water (50 ml) was added to the cooled mixture followed by dichloromethane (50 ml). The organic layer was separated, washed with hydrochloric acid (50 ml, 2 M) and water (50 ml), and dried ($MgSO_{4\ (anh)}$). Filtration and removal of the solvent in vacuo gave a tan-coloured gum (1 g). This material was purified by column chromatography on silica eluting with dichloromethane to give (E)-5-(4-hydroxy-3-methoxyphenyl)-2-methyl-1-phenyl-pent-4-ene-1,3-dione (575 mg, 55%) as a light tan-coloured gum: $^1R$ NMR (500 MHz, $CDCl_3$) δ 1.55 (3H, d, J=7.0 Hz, C—$CH_3$), 3.91 (3H, s, $OCH_3$), 4.69 (1H, q, J=7.0 Hz, H-2), 5.98 (1H, s, OH), 6.68 (1H, d, J=15.8 Hz, H-4), 6.90 (1H, d, J=8.2 Hz, H-5'), 7.00 (1H, d, J=1.8 Hz, H-2'), 7.07 (1H, dd, J=8.2, 1.8 Hz, H-6'), 7.46 (2H, t, J=7.6 Hz, H-3", H-5"), 7.53 (1H, t, J=8.2 Hz, H-4"), 7.60 (1H, d, J=15.8 Hz, H-5), 8.00 (1H, brd, J=7.3 Hz, H-2", H-6") ppm; TLC $R_f$=0.35 (dichloromethane). HPLC analysis indicated a purity of 95.8%.

Example 22

(E)-1-(4-Hydroxy-3-methoxyphenyl)-4,6,6-trimethyl-hept-1-ene-3,5-dione (Compound 36)

By a similar procedure as described in Example 21, but starting from compound 34 and using potassium t-butoxide as the base, (E)-1-(4-hydroxy-3-methoxyphenyl)-4,6,6-trimethyl-hept-1-ene-3,5-dione (0.441 g, 18%) was obtained as a clear oil: LRMS (m/z) 291 $(MH^+)^+$; $^1H$ NMR (300 MHz, $CDCl_3$) δ 1.61 (9H, s, $C(CH_3)_3$), 1.38 (3H, d, J=6.9 Hz, H-4), 3.94 (3H, s, $OCH_3$), 4.27 (1H, q, J=6.9 Hz, H-4), 5.93 (1H, s, OH), 6.73 (1H, d, J=15.6 Hz, H-6), 6.91 (1H, d, J=8.4 Hz, H-5'), 7.04 (1H, d, J=2.1 Hz, H-2'), 7.12 (1H, dd, J=8.1, 2.1 Hz, H-6'), 7.58 (1H, d, J=15.9 Hz, H-7) ppm.

Example 23

5-(4-Hydroxy-3-methoxyphenyl)-2-methyl-1-p-tolyl-pent-4-ene-1,3-dione (Compound 46)

By a similar procedure as described in Example 21, but starting from compound 65 and using potassium t-butoxide as the base, 5-(4-hydroxy-3-methoxyphenyl)-2-methyl-1-p-tolyl-pent-4-ene-1,3-dione (0.88 g, 47%) was obtained as a yellow oil: $^1H$ NMR (300 MHz, $CDCl_3$) δ 1.53 (3H, d, J=6.9 Hz, $CCH_3$), 2.38 (3H, s, Ar—$CH_3$), 3.90, (3H, s, $OCH_3$), 4.65 (1H, q, J=6.9 Hz, H-2), 6.00 (1H, s, OH), 6.66 (1H, d, J=15.9 Hz, H-4), 6.88 (1H, d, J=8.1 Hz, H-5'), 6.99 (1H, d, J=1.8 Hz, H-2'), 7.06 (1H, dd, J=8.1, 2.1 Hz, ArH), 7.25 (2H, d, J=6.9 Hz, H-3", H-5"), 7.58 (1H, d, J=15.6 Hz, H-5), 7.90 (2H, d, J=8.1 Hz, H-2", H-6") ppm.

Example 24

5-(4-Hydroxy-3-methoxyphenyl)-1-(4-methoxyphenyl)-2-methyl-pent-4-ene-1,3-dione (Compound 49)

By a similar procedure as described in Example 21, but starting from compound 66 and using potassium t-butoxide as the base, 5-(4-hydroxy-3-methoxyphenyl)-1-(4-methoxyphenyl)-2-methyl-pent-4-ene-1,3-dione (0.298 g, 23%) was obtained as a yellow oil: LRMS (m/z) 341 $(MH^+)$; $^1H$ NMR (300 MHz, $CDCl_3$) δ 1.52 (3H, d, J=6.6 Hz, $C(CH_3)_3$), 3.84 (3H, s, $OCH_3$), 3.90 (3H, s, $OCH_3$), 4.60 (1H, q, J=6.9 Hz, $CHCH_3$), 5.91 (1H, s, OH), 6.65 (1H, d, J=15.9 Hz, H-4), 6.87-6.94 (3H, m, ArH), 6.98 (1H, d, J=1.8 Hz, H-2'), 7.05 (1H, dd, J=8.1, 2.1 Hz, H-6'), 7.57 (1H, d, J=15.9 Hz, H-5), 7.99 (2H, d, J=9.0 Hz, H-2", H-6") ppm.

Example 25

5-(4-Hydroxy-3-methoxylphenyl)-2,2-dimethyl-1-phenyl-pent-4-ene-1,3-dione (Compound 64)

By a similar procedure as described in Example 21, but starting from compound 43, 5-(4-hydroxy-3-methoxy-phenyl)-2,2-dimethyl-1-phenyl-pent-4-ene-1,3-dione (0.193 g, 35%) was obtained as a yellow oil: LRMS (m/z) 325 $(MH^+)$, 347 $(M+Na)^+$; $^1H$ NMR (300 MHz, $CDCl_3$) δ 1.54 (6H, s, $CH_3$), 3.95 (3H, s, $OCH_3$), 5.87 (1H, s, OH), 6.53 (1H, d, J=15.6 Hz, H-4), 6.86 (1H, d, J=8.4 Hz, H-5'), 6.91 (1H, d, J=1.8 Hz, H-2'), 7.03 (1H, dd, J=8.1, 1.8 Hz, H-6'), 7.37 (2H, t, J=7.5 Hz, H-3", H-5"), 7.48-7.50 (1H, m, H-4"), 7.69 (1H, d, J=15.6 Hz, H-5), 7.82 (2H, d, J=7.5 Hz, H-2", H-6") ppm.

Example 26

(E)-2-Ethyl-5-(4-hydroxy-3-methoxyphenyl)-1-phenyl-pent-4-ene-1,3-dione (Compound 44)

To sodium hydride (54 mg, 1.36 mmol) in anhydrous THF (12 ml) was added compound 68 (400 mg, 1.36 mmol) under a nitrogen atmosphere. The mixture was stirred at room temperature until a clear red solution occurred (approx. 40 min). Trimethylsilyl chloride (0.16 ml, 1.36 mmol) was added and the mixture heated at 55° C. for 1 h. The reaction was cooled to room temperature, potassium carbonate (200 mg, 1.44 mmol) was added and the reaction was stirred for a further 45 min. After cooling to 0° C., a solution of iodoethane (0.16 ml, 1.84 mmol) was added and the mixture heated at reflux for 18 h. Water (20 ml) was added to the cooled mixture, followed by dichloromethane (20 ml). The organic layer was separated, washed with hydrochloric acid (20 ml, 2 M) and water (20 ml) and dried over $MgSO_{4\ (anh)}$. Removal of the solvent in vacuo gave a yellow oil. $^1H$ NMR indicated a 15-20% conversion to product. Purification by flash column chromatography using dichloromethane as eluent gave starting compound 68 as the major product, plus (E)-2-ethyl-5-(4-hydroxy-3-methoxyphenyl)-1-phenyl-pent-4-ene-1,3-dione (40 mg, 9%) as a yellow oil: $^1$H NMR (400 MHz, CDCl$_3$) δ 0.93 (3H, t, CH$_3$), 2.01-2.20 (2H, m, CH$_2$), 3.85 (3H, s, OCH$_3$), 4.47 (1H, t, H-2), 5.89 (1H, s, OH), 6.67 (1H, d, H-4), 6.85 (1H, d, H-5'), 6.94 (1H, s, H-2'), 7.05 (1H, d, H-6'), 7.41 (2H, t, H-3", H-5"), 7.45-7.65 (2H, m, H-4', H-5), 7.97 (2H, d, H-2", H-6") ppm.

Example 27

5-(4-Hydroxy-3-methoxyphenyl)-2-methyl-1-(1-methylcyclopropyl)pent-4-ene-1,3-dione (Compound 39)

By a similar method to Example 21, but starting with compound 38 and using NaH in place of potassium carbonate, 5-(4-hydroxy-3-methoxyphenyl)-2-methyl-1-(1-methylcyclopropyl)pent-4-ene-1,3-dione (48 mg, 46%) was obtained as a yellow oil: $^1$H NMR (400 MHz, CDCl$_3$) δ 0.73-0.81 (2H, m, cyclopropyl CH$_2$), 1.26-1.30 (1H, m, cyclopropyl CH$_2$), 1.37-1.41 (7H, m, 1×cyclopropyl CH$_2$, 2×CH$_3$), 3.95 (3H, s, OCH$_3$), 4.06 (1H, q, J=6.8 Hz, H-2), 6.69 (1H, d, J=16.0 Hz, H-4), 6.94 (1H, d, J=8.0 Hz, H-5'), 7.05 (1H, d, J=2.0 Hz, H-2'), 7.13 (1H, dd, J=8.0, 2.0 Hz, H-6'), 7.60 (1H, d, J=16.0 Hz, H-5) ppm.

Example 28

(E)-1,5-Bis(4-tert-butyldimethylsilyloxy-3-methoxyphenyl)-2-methylpent-4-ene-1,3-dione (Compound 48)

To a solution of compound 47 (300 mg, 0.88 mmol) dissolved in anhydrous DMF (6 ml) was added imidazole (239 mg, 3.51 mmol) and tert-butyldimethylsilyl chloride (291 mg, 1.93 mmol). The mixture was stirred at room temperature under a nitrogen atmosphere for 18 h. The solvents were removed in vacuo and the residue taken up in dichloromethane (30 ml); washed with sat. aq NH$_4$Cl (30 ml); dried over MgSO$_{4\ (anh)}$, filtered and concentrated in vacuo to give a residue. Purification on a silica gel column using dichloromethane as the eluent gave (E)-1,5-bis(4-tert-butyldimethylsilyloxy-3-methoxyphenyl)pent-4-ene-1,3-dione (459 mg, 92%) as a yellow oil: $^1$H NMR (400 MHz, CDCl$_3$) δ 0.19 (6H, s, 2×CH$_3$), 0.20 (6H, s, 2×CH$_3$), 1.02 (18H, brs, 2×(CH$_3$)$_3$), 3.87 (3H, s, OCH$_3$), 3.90 (3H, s, OCH$_3$), 6.29 (1H, brs, CH), 6.52 (1H, d, J=15.6 Hz, H-4), 6.89 (2H, m, 2×ArH), 7.07 (2H, brs, 2×ArH), 7.47 (1H, d, J=7.2 Hz, ArH), 7.55 (1H, s, ArH), 7.61 (1H, d, J=15.6 Hz, H-5) ppm.

To a solution of (E)-1,5-bis(4-tert-butyldimethylsilyloxy-3-methoxyphenyl)-pent-4-ene-1,3-dione (459 mg, 0.80 mmol) in anhydrous diethyl ether (8 ml) was added sodium (20 mg, 0.88 mmol). The mixture was stirred for 18 h, when all the sodium had been consumed, forming a yellow solid. The diethyl ether was removed under vacuum, and the yellow oily solid was dissolved in acetone (8 ml). Methyl iodide (45 µl, 0.72 mmol) was added to this mixture and stirred overnight at room temperature. The acetone was removed under vacuum, and the residue was taken up in ethyl acetate, washed with water, dried (MgSO$_{4\ (anh)}$), filtered and concentrated in vacuo. The residue was purified on silica gel column using dichloromethane/petroleum ether (1:1 to 1:0) to give 1,5-bis(4-tert-butyldimethylsilyloxy-3-methoxyphenyl)-2-methyl-pent-4-ene-1,3-dione (281 mg, 60%) as a yellow oil: $^1$H NMR (400 MHz, CDCl$_3$) δ 0.16 (6H, s, 2×CH$_3$), 0.18 (6H, s, 2×CH$_3$), 0.99 (18H, br s, 2×(CH$_3$)$_3$)), 1.54 (3H, d, J=7.0 Hz, CH$_3$), 3.83 (3H, s, OCH$_3$), 3.85 (3H, s, OCH$_3$), 4.66 (1H, q, J=7.0 Hz, H-2), 6.69 (1H, d, J=16 Hz, H-4), 6.83 (1H, d, J=8.4 Hz, H-5'), 6.87 (1H, d, J=8.4 Hz, H-5'), 7.00 (1H, d, J=2.0 Hz, H-2'), 7.03 (1H, dd, J=8.4, 2.0 Hz, H-6'), 7.53-7.58 (2H, m, ArH), 7.60 (1H, d, J=16.0 Hz, H-5) ppm.

Example 29

(E)-2-Benzyl-5-(4-hydroxy-3-methoxyphenyl)-1-phenylpent-4-ene-1,3-dione (Compound 45)

By a similar procedure as described in Example 28 for the protection of the phenolic group, but starting from compound 68, (E)-5-(4-tert-butyldimethylsilyloxy-3-methoxyphenyl)-1-phenylpent-4-ene-1,3-dione (199 mg, 72%) was obtained as a yellow oil: $^1$H NMR (400 MHz, CDCl$_3$) δ 0.19 (6H, s, 2×CH$_3$), 1.01 (9H, s, 3×CH$_3$), 3.87 (3H, s, OCH$_3$), 6.34 (1H, brs, OH), 6.53 (1H, d, J=15.6 Hz, H-4), 6.87 (1H, d, J=8.0 Hz, H-5'), 7.07-7.10 (2H, m, 2×ArH), 7.47-7.56 (3H, m, 3×ArH), 7.65 (1H, d, J=15.6 Hz, H-5), 7.94-7.97 (2H, m, H-2", H-6") ppm.

By a similar procedure as described in Example 28 for the alkylation, but using benzyl bromide and potassium iodide as the alkylating agents, (E)-2-benzyl-5-(4-tert-butyldimethylsilyloxy-3-methoxyphenyl)-1-phenylpent-4-ene-1,3-dione (204 mg, 84%) was obtained as a yellow oil: $^1$H NMR (400 MHz, CDCl$_3$) δ 0.19 (6H, s, 2×CH$_3$), 1.02 (9H, s, 3×CH$_3$), 3.36 (1H, dd, J=14.0, 7.0 Hz, CH$_2$Ar), 3.53 (1H, dd, J=14.0, 7.0 Hz, CHAr), 3.85 (3H, s, OCH$_3$), 4.98 (1H, t, J=7.0 Hz, H-2), 6.71 (1H, d, J=16.0 Hz, H-4), 6.85 (1H, d, J=8.0 Hz, H-5'), 6.97 (1H, d, J=2.0 Hz, H-2'), 7.02 (1H, dd, J=8.0, 2.0 Hz, H-6'), 7.20-7.29 (5H, m, 5×ArH), 7.46 (2H, brt, J=8.0 Hz, 2×ArH), 7.56 (1H, d, J=16.0 Hz, H-5), 7.55-7.59 (1H, m, ArH), 7.98-8.01 (2H, m, 2×ArH) ppm.

(E)-2-Benzyl-5-(4-tert-butyldimethylsilyloxy-3-methoxyphenyl)-1-phenylpent-4-ene-1,3-dione (204 mg, 0.41 mmol) was dissolved in anhydrous THF (5 ml) and stirred at room temperature under a nitrogen atmosphere. TBAF (0.14 ml, 0.49 mmol) was added (yellow/green solution goes deep red colour) and the mixture was stirred overnight at room temperature. After this time the solvents were removed in vacuo to leave a residue which was purified on silica gel column using dichloromethane/diethyl ether (1:0 to 10:1) to give (E)-2-benzyl-5-(4-hydroxy-3-methoxyphenyl)-1-phenylpent-4-ene-1,3-dione (134 mg, 85%) as a light green foam: $^1$H NMR (400 MHz, CDCl$_3$) δ 3.34 (1H, dd, J=14.0, 7.2 Hz, CH$_2$), 3.50 (1H, dd, J=14.0, 7.2 Hz, CH$_2$), 3.92 (3H, s, OCH$_3$), 4.95 (1H, t, J=7.2 Hz, H-2), 5.96 (1H, brs, OH), 6.68 (1H, d, J=16.0 Hz, H-4), 6.90 (1H, d, J=8.0 Hz, H-5'), 6.95 (1H, d, J=2.0 Hz, H-2'), 7.04 (1H, dd, J=8.0, 2.0 Hz, H-6'), 7.16-7.28 (5H, m, 5×ArH), 7.44 (2H, brt, J=8.0 Hz, 2×H-5", H-3", H-6), 7.53 (1H, d, J=16.0 Hz, H-5), 7.52-7.57 (1H, m, H-4"), 7.96-7.98 (2H, m, H-2", H-6") ppm.

Example 30

6,6-Dimethyl-1-(4-hydroxy-3-methoxyphenyl)-heptane-3,5-dione (Compound 2)

Method 1

To a solution of compound 34 (0.92 g, 3.3 mmol) in acetone (100 ml) was added Raney nickel (10 ml of a 50% slurry in water). The mixture was stirred under 2 atm pressure of hydrogen for 3 h, refilling the reaction vessel with hydrogen to 2 atm at 1 h intervals. The reaction mixture was filtered through Celite to remove the catalyst and the Celite pad washed with acetone. The combined filtrate and washings were concentrated in vacuo. The residue was dissolved water (25 ml) and extracted with dichloromethane (50 ml, 2×25 ml). The extracts were combined, dried ($MgSO_{4\,(anh)}$), filtered and evaporated in vacuo to leave an orange oil. Polar impurities were removed by column chromatography using silica, eluting with dichloromethane to afford 6,6-dimethyl-1-(4-hydroxy-3-methoxyphenyl)-heptane-3,5-dione (0.38 g, 41%) as a yellow gum that could not be made to crystallise: $^1$H NMR (500 MHz, $CDCl_3$) δ 1.17 (9H, s, $C(CH_3)_3$), 2.62 (2H, t, J=1.4 Hz, H-1), 2.88 (2H, t, J=1.4 Hz, H-2), 3.88 (3H, s, $OCH_3$), 5.57 (2H, s, H-4), 6.70-6.85 (3H, multiplet, aromatics), 15.83 (1H, brs, OH) ppm.

Method 2

By a similar procedure as described in Example 31, but starting from compound 34, 6,6-dimethyl-1-(4-hydroxy-3-methoxyphenyl)-heptane-3,5-dione (7.2 g, 90%) was obtained as a light tan oil.

Example 31

1-(4-Hydroxy-3-methoxyphenyl)-6-methyl-heptane-3,5-dione)

(Compound 1)

To a solution of compound 33 (0.75 g, 2.86 mmol) in toluene (30 ml) containing pyridine (0.4 g) was added 5% palladium on carbon (75 mg). The mixture was stirred under 1 atm pressure of hydrogen overnight. The reaction mixture was filtered through a short silica pad to remove the catalyst. The catalyst was washed with toluene, and the combined filtrate and washings were evaporated in vacuo. The residue was subjected to high vacuum to remove remaining solvent to give 1-(4-hydroxy-3-methoxyphenyl)-6-methyl-heptane-3,5-dione) (0.73 g, 97%) as a light tan-coloured oil: $^1$H NMR (300 MHz, $CDCl_3$) δ 1.10 (6H, s, $C(CH_3)_2$), 2.42 (1H, m, H-6), 2.55 (2H, t, J=7.0 Hz, H-2), 2.83 (2H, m, H-1), 3.83 (3H, s, $OCH_3$), 5.44 (1H, s, H-4), 5.59 (1H, brs, OH), 6.66 (2H, m, aromatic H), 6.81 (1H, d, J=7.2 Hz, aromatic H), 15.5 (1H, brs, OH) ppm. HPLC analysis indicated a purity of 95.2%.

Example 32

5-(4-Hydroxy-3-methoxyphenyl)-1-phenyl-pentane-1,3-dione (Compound 69)

By a similar procedure as described in Example 31, but starting from compound 68, 5-(4-hydroxy-3-methoxy-phenyl)-1-phenyl-pentane-1,3-dione (500 mg, 1.68 mmol, 99%) was obtained as a yellow solid: mp 76-78° C. (lit. 78.5° C., Lampe, W and Smolinska, Bulletin de L'Academie Polonaise des Sciences, 49-53, 11 (1963)); $^1$H NMR (400 MHz; $CDCl_3$) δ 2.67-2.75 (2H, m, $CH_2$), 2.92-2.98 (2H, m, $CH_2$), 3.86 (3H, s, $OCH_3$), 5.49 (1H, s, H-2 or phenol OH), 6.14 (1H, s, H-2 or phenol OH), 6.70-6.75 (2H, m, ArH), 6.82-6.86 (1H, m, ArH), 7.42-7.49 (1H, m, H-4''), 7.54 (2H, m, PhH), 16.16 (1H, s, enol OH) ppm; $^{13}$C NMR (100 MHz; $CDCl_3$) δ 196.0, 183.3, 146.5, 144.1, 134.9, 132.7, 132.4, 128.7, 127.1, 120.9, 114.4, 111.1, 96.5, 56.0, 41.5, 31.5 ppm.

Example 33

7,7-Dimethyl-1-(4-hydroxy-3-methoxyphenyl)-octane-3,5-dione (Compound 3)

By a similar procedure as described in Example 31, but starting from compound 35, 7,7-dimethyl-1-(4-hydroxy-3-methoxy-phenyl)-octane-3,5-dione (54 mg, 0.18 mmol, 35%) was obtained as a yellow oil: $^1$H NMR (400 MHz; $CDCl_3$) δ 0.97 (9H, s, $(CH_3)_3$), 2.09 (2H, s, $t$-$BuCH_2$), 2.57 (2H, t, J=8.0 Hz, $CH_2$), 2.86 (2H, t, J=8.0 Hz, $CH_2$), 3.86 (3H, s, $OCH_3$), 5.38 (1H, s, H-4), 5.51 (1H, s, OH), 6.66-6.68 (2H, m, ArH), 6.80-6.83 (1H, s, ArH), 15.62 (1H, s, OH) ppm; $^{13}$C NMR (100 MHz; $CDCl_3$) δ 195.6, 191.0, 146.5, 144.0, 132.7, 120.9, 114.4, 111.0, 101.9, 55.9, 51.4, 41.2, 31.8, 31.4, 30.0 ppm.

Example 34

1-(4-Hydroxy-3-methoxyphenyl)-4,6,6-trimethyl-heptane-3,5-dione (Compound 4)

By a similar procedure as described in Example 31, but starting from compound 36, 1-(4-hydroxy-3-methoxyphenyl)-4,6,6-trimethyl-heptane-3,5-dione (0.273 g, 61%) was obtained as a colourless oil: LRMS (m/z) 291 $M^+$(–H); $^1$H NMR (300 MHz, $CDCl_3$) δ 1.07 (9H, s, $C(CH_3)$), 1.21 (3H, d, J=7.2 Hz, $CHCH_3$), 2.68-2.76 (4H, m, H-1, H-2), 3.79 (3H, s, $OCH_3$), 4.00 (1H, q, J=6.9 Hz, H-4), 5.72 (1H, s, OH), 6.56-6.65 (2H, m, ArH), 6.74 (1H, d, J=8.1 Hz, ArH) ppm; $^{13}$C NMR (75 MHz, $CDCl_3$) δ 14.72, 25.88, 29.07, 41.89, 45.19, 54.66, 55.68, 111.07, 114.18, 120.00, 132.57, 143.83, 146.32, 205.90, 212.20 ppm.

Example 35

1-cyclopropyl-5-(4-hydroxy-3-methoxyphenyl)-pentane-1,3-dione (Compound 5)

By a similar procedure as described in Example 31, but starting from compound 37, 1-cyclopropyl-5-(4-hydroxy-3-methoxy-phenyl)-pentane-1,3-dione (390 mg, 1.49 mmol, 78%) was obtained as a yellow oil: $^1$H NMR (400 MHz; $CDCl_3$) δ 0.85-0.95 (2H, m, cyclopropyl $CH_2$), 1.03-1.11 (2H, m, cyclopropyl $CH_2$), 1.55-1.65 (1H, m, cyclopropyl CH), 2.47-2.55 (2H, m, $CH_2$), 2.80-2.88 (2H, m, $CH_2$), 3.86 (3H, s, $OCH_3$), 5.51 (1H, s, H-2 or OH), 5.57 (1H, s, H-2 or OH), 6.65-6.71 (2H, m, ArH), 6.78-6.86 (1H, m, ArH), 15.69 (1H, s, OH) ppm; $^{13}$C NMR (100 MHz; $CDCl_3$) δ 199.1, 187.0, 146.5, 144.0, 132.7, 120.9, 114.4, 111.0, 99.3, 55.9, 39.2, 31.9, 18.7, 10.4 ppm.

Example 36

5-(4-Hydroxy-3-methoxyphenyl)-1-(1-methylcyclo-propyl)-pentane-1,3-dione (Compound 6)

By a similar procedure as described in Example 31, but starting from compound 6, 5-(4-hydroxy-3-methoxyphenyl)-1-(1-methylcyclo-propyl)-pentane-1,3-dione (235 mg, 0.85 mmol, 58%) was obtained as a pale yellow oil: $^1$H NMR (400

MHz; CDCl$_3$) δ 0.73-0.79 (2H, m, cyclopropyl CH$_2$), 1.23-1.28 (5H, m, cyclopropyl CH$_2$ and CH$_3$), 2.52-2.58 (2H, m, CH$_2$), 2.80-2.87 (2H, m, CH$_2$), 3.87 (3H, s, OCH$_3$), 5.47 (1H, s, H-2 or OH), 5.54 (1H, s, H-2 or OH), 6.65-6.69 (2H, m, ArH), 6.78-6.83 (1H, m, ArH), 16.08 (1H, s, OH) ppm; $^{13}$C NMR (100 MHz; CDCl$_3$) δ 198.7, 190.6, 146.5, 144.0, 132.8, 120.9, 114.4, 111.0, 96.0, 55.9, 40.2, 31.8, 21.0, 19.7, 18.5 ppm.

Example 37

5-(4-Hydroxy-3-methoxylphenyl)-2-methyl-1-(1-methylcyclopropyl)-pentane-1,3-dione (Compound 7)

By a similar procedure as described in Example 31, but starting from compound 39, 5-(4-hydroxy-3-methoxyphenyl)-2-methyl-1-(1-methylcyclopropyl)pentane-1,3-dione (43 mg, 90%) was obtained as a pale yellow oil: LRMS (m/z) 313 (M+Na)$^+$; $^1$H NMR (400 MHz, CDCl$_3$) δ 0.74-0.80 (2H, m, cyclopropyl CH$_2$), 1.19-1.23 (1H, m, cyclopropyl CH$_2$), 1.25 (3H, d, J=7.0 Hz, CH$_3$), 1.29-1.31 (1H, m, cyclopropyl CH$_2$), 1.32 (3H, s, CH$_3$), 2.70-2.83 (4H, m, 2×CH$_2$), 3.73 (1H, q, J=7.0 Hz, CH), 3.88 (3H, s, OCH$_3$), 5.49 (1H, s, OH), 6.64-6.81 (2H, m, 2×ArH), 6.82 (1H, d, J=8.0 Hz, ArH) ppm; $^{13}$C NMR (100 MHz, CDCl$_3$) δ 13.69, 18.36, 18.41, 19.61, 26.88, 29.25, 42.33, 55.05, 111.03, 114.23, 120.78, 132.75, 143.86, 146.32, 206.15, 208.70 ppm.

Example 38

1-Cyclopentyl-5-(4-hydroxy-3-methoxyphenyl)-pentane-1,3-dione (Compound 8)

By a similar procedure as described in Example 31, but starting from compound 40, 1-cyclopentyl-5-(4-hydroxy-3-methoxyphenyl)-pentane-1,3-dione (50 mg, 0.17 mmol, 30%) was obtained as a pale yellow oil: $^1$H NMR (400 MHz; CDCl$_3$) δ 1.52-1.88 (9H, m, cyclopentyl), 2.52-2.57 (2H, m, CH$_2$), 2.80-2.87 (2H, m, CH$_2$), 3.85 (3H, s, OCH$_3$), 5.46 (1H, s, H-2), 6.63-6.68 (2H, m, ArH), 6.78-6.82 (1H, m, ArH), 15.56 (1H, s, OH) ppm; $^{13}$C NMR (100 MHz; CDCl$_3$) δ 198-1, 192.8, 146.5, 144.0, 132.7, 120.9, 114.4, 111.1, 98.6, 55.9, 47.7, 40.5, 31.6, 30.4, 26.1 ppm.

Example 39

1-(4-Hydroxy-3-methoxyphenyl)-6-methyloctane-3,5-dione (Compound 9)

By a similar procedure as described in Example 31, but starting from compound 41, 1-(4-hydroxy-3-methoxyphenyl)-6-methyloctane-3,5-dione (200 mg, 79%) was obtained as a pale yellow oil: $^1$H NMR (400 MHz, CDCl$_3$) δ 0.86 (3H, t, J=7.2 Hz, CH$_3$), 1.09 (3H, d, J=7.2 Hz, CH$_3$), 1.37-1.46 (1H, m, CH$_2$), 1.56-1.66 (1H, m, CH$_2$), 2.15-2.23 (1H, m, CH), 2.56 (2H, t, J=7.8 Hz, CH$_2$), 2.82-2.88 (2H, m, CH$_2$), 3.85 (3H, s, OCH$_3$), 5.43 (1H, s, H-4), 6.64-6.68 (2H, m, ArH), 6.79-6.83 (1H, m, ArH), 15.60 (1H, s, H-4) ppm; $^{13}$C NMR (100 MHz, CDCl$_3$) δ 197.8, 194.1, 146.5, 144.0, 132.7, 120.9, 114.4, 111.1, 98.6, 56.0, 43.9, 40.8, 31.5, 27.1, 17.3, 11.8 ppm.

Example 40

5-(4-Hydroxy-3-methoxy-phenyl)-1-(1-methyl-cyclohexyl)-pentane-1,3-dione (Compound 10)

By a similar procedure as described in Example 31, but starting from compound 42, 5-(4-hydroxy-3-methoxyphenyl)-1-(1-methyl-cyclohexyl)-pentane-1,3-dione (54 mg, 0.18 mmol, 35%) was obtained as a pale yellow oil: $^1$H NMR (400 MHz; CDCl$_3$) δ 1.08 (3H, s, CH$_3$), 1.24-1.66 (10H, m, cyclohexyl CH$_2$), 2.56-2.61 (2H, m, CH$_2$), 2.90-2.95 (2H, m, CH$_2$), 3.77 (3H, s, OCH$_3$), 5.57 (1H, s, H-2), 7.71-7.76 (2H, m, ArH), 6.85-6.91 (1H, m, ArH), 15.96 (1H, s, OH) ppm; $^{13}$C NMR (100 MHz; CDCl$_3$) δ 201.2, 193.2, 176.0, 151.1, 139.5, 122.7, 120.3, 112.7, 96.5, 55.9, 51.8, 43.5, 40.5, 35.0, 31.8, 26.0, 22.8 ppm.

Example 41

5-(4-Hydroxy-3-methoxy-phenyl)-2-methyl-1-phenyl-pentane-1,3-dione (Compound 11)

By a similar procedure as described in Example 31, but starting from compound 43, 5-(4-hydroxy-3-methoxy-phenyl)-2-methyl-1-phenyl-pentane-1,3-dione (85 mg, 0.27 mmol, 28%) was obtained as a yellow oil: $^1$H NMR (400 MHz; CDCl$_3$) δ 1.40 (3H, d, J=7.2 Hz, CH$_3$), 2.65-2.83 (4H, m, CH$_2$CH$_2$), 3.80 (3H, s, OCH$_3$), 4.43 (1H, q, J=7.2 Hz, H-2), 5.44 (1H, s, OH), 6.56-6.61 (2H, m, ArH), 6.73-6.78 (1H, m, ArH), 7.40-7.48 (2H, m, ArH), 7.56-7.61 (1H, m, ArH), 7.85-7.91 (2H, m, ArH) ppm; $^{13}$C NMR (100 MHz; CDCl$_3$) δ 206.6, 197.5, 146.4, 144.0, 136.0, 133.7, 132.7, 128.9, 128.7, 120.9, 114.4, 111.1, 56.5, 55.9, 42.7, 29.5, 13.6 ppm.

Example 42

2-Ethyl-5-(4-hydroxy-3-methoxyphenyl)-1-phenyl-pentane-1,3-dione (Compound 12)

By a similar procedure as described in Example 31, but starting from compound 44, 2-ethyl-5-(4-hydroxy-3-methoxyphenyl)-1-phenyl-pentane-1,3-dione (32 mg, 80%) was obtained as a yellow oil: LCMS (m/z) 349 (M+Na)$^+$; $^1$H NMR (400 MHz, CDCl$_3$) δ 0.82 (3H, t, CH$_3$), 1.85-2.00 (2H, m, CH$_2$), 2.60-2.75 (4H, m, 2×CH$_2$), 3.72 (3H, s, OCH$_3$), 4.25 (1H, t, H-2), 6.49-6.51 (2H, m, 2×ArH), 6.67 (1H, d, ArH), 7.38 (2H, t, 2×ArH), 7.50 (1H, t, ArH), 7.83 (2H, d, 2×ArH) ppm; $^{13}$C NMR (100 MHz; CDCl$_3$) δ 12.31, 22.40, 29.37, 42.56, 55.89, 64.79, 111.10, 114.33, 120.94, 128.68, 128.89, 132.65, 133.68, 136.63, 143.95, 146.39, 196.57, 205.77 ppm.

Example 43

2-Benzyl-5-(4-hydroxy-3-methoxyphenyl)-1-phenyl-pentane-1,3-dione (Compound 13)

By a similar procedure as described in Example 31, but starting from compound 45, 2-benzyl-5-(4-hydroxy-3-methoxyphenyl)-1-phenylpentane-1,3-dione (132 mg, 98%) was obtained as a yellow/green oil: LCMS (m/z) 388 (M)⁺; ¹H NMR (400 MHz, CDCl₃) δ 2.61-2.81 (4H, m, 2×CH₂), 3.28 (2H, dd, J=7.0, 3.0 Hz, CH₂), 3.79 (3H, s, OCH₃), 4.76 (1H, t, J=7.0 Hz, H-2), 5.46 (1H, brs, OH), 6.52-6.54 (2H, m, 2×ArH), 6.74 (1H, d, J=8.0 Hz, ArH), 7.14-7.26 (5H, m, 5×ArH), 7.41 (2H, brt, J=8.0 Hz, 2×ArH), 7.54-7.58 (1H, m, ArH), 7.82-7.84 (2H, m, 2×ArH) ppm; ¹³C NMR (100 MHz, CDCl₃) δ 29.18, 34.66, 43.53, 55.74, 64.33, 110.94, 114.18, 120.78, 126.60, 128.59, 128.75, 128.78, 132.41, 133.62, 136.30, 138.39, 143.82, 146.23, 195.63, 204.58 ppm.

Example 44

5-(4-Hydroxy-3-methoxylphenyl)-2-methyl-1-p-tolyl-pentane-1,3-dione (Compound 14)

By a similar procedure as described in Example 31, but starting from compound 46, 5-(4-hydroxy-3-methoxyphenyl)-2-methyl-1-p-tolyl-pentane-1,3-dione (0.37 g, 42%) was obtained as a yellow oil: LRMS (m/z) 325 (M−H)⁺; ¹H NMR (300 MHz, CDCl₃) δ 1.39 (3H, d, J=7.2 Hz, CCH₃), 2.40 (3H, s, ArCH₃), 2.66-2.82 (4H, m, CH₂ CH₂), 3.79, (3H, s, OCH₃), 4.40 (1H, q, J=7.2 Hz, H-2), 5.52 (1H, s, OH), 6.56-6.61 (2H, m, ArH), 6.75 (1H, d, J=9.0 Hz, ArH), 7.24 (2H, d, J=8.4 Hz, ArH), 7.78 (2H, d, J=8.4 Hz, ArH) ppm; ¹³C NMR (75 MHz, CDCl₃) δ 13.32, 21.46, 29.23, 42.32, 55.65, 56.23, 110.91, 114.12, 120.70, 128.60, 129.33, 132.49, 133.37, 143.80, 144.44, 146.22, 196.75, 206.29 ppm.

Example 45

1,5-Bis(4-hydroxy-3-methoxyphenyl)-pentane-1,3-dione (Compound 15)

By a similar procedure as described in Example 31, but starting from compound 47, 1,5-bis(4-hydroxy-3-methoxyphenyl)-pentane-1,3-dione (170 mg, 68%) was obtained as a green solid: LCMS (m/z) 345 (M)⁺; ¹H NMR (400 MHz, CDCl₃) δ 2.69 (2H, t, J=7.6 Hz, CH₂), 2.87 (1H, m, H-2), 2.93-2.97 (2H, m, CH₂), 3.87 (3H, s, OCH₃), 3.97 (3H, s, OCH₃), 6.07 (1H, s, OH), 6.66-6.74 (2H, m, 2×ArH), 6.85 (1H, d, J=8.4 Hz, ArH), 6.95 (1H, d, J=8.4 Hz, ArH), 7.43 (1H, dd, J=8.4, 2.0 Hz, ArH), 7.46 (1H, d, J=2.0 Hz, ArH) ppm; ¹³C NMR (100 MHz, CDCl₃) δ 31.69, 40.59, 55.84, 56.06, 95.55, 109.21, 110.95, 114.17, 114.28, 120.83, 121.77, 124.56, 127.61, 132.66, 143.93, 146.57, 149.80, 184.99, 192.42 ppm.

Example 46

1,5-Bis(4-hydroxy-3-methoxyphenyl)-2-methyl-pentane-1,3-dione (Compound 16)

By a similar procedure as described in Example 31, but starting from compound 48, 1,5-bis(4-tert-butyldimethylsilyloxy-3-methoxyphenyl)-2-methyl-pentane-1,3-dione (250 mg, 94%) was obtained as a yellow oil which required no further purification: ¹H NMR (400 MHz, CDCl₃) δ 0.13 (6H, s, 2×CH₃), 0.19 (6H, s, 2×CH₃), 0.98 (9H, brs, (CH₃)₃)), 1.00 (9H, brs, (CH₃)₃)), 1.38 (3H, d, J=6.8 Hz, (CH₃)₃)), 2.66-2.83 (4H, m, 2×CH₂), 3.75 (3H, s, OCH₃), 3.86 (3H, s, OCH₃), 4.39 (1H, q, J=6.8 Hz, H-2), 6.55 (1H, d, J=8.0 Hz, ArH), 6.60 (1H, brs, ArH), 6.71 (1H, d, J=8.0 Hz, ArH), 6.87 (1H, d, J=8.0 Hz, ArH), 7.43 (1H, d, J=8.0 Hz, ArH), 7.50 (1H, brs, ArH) ppm.

1,5-Bis(4-tert-butyldimethylsilyloxy-3-methoxyphenyl)-2-methyl-pentane-1,3-dione (250 mg, 0.43 mmol) was dissolved in anhydrous THF (8 ml) and stirred at room temperature under a nitrogen atmosphere. Tetrabutylammonium fluoride (0.27 ml, 0.94 mmol) was added and the mixture was stirred for 2 h and monitored by TLC. After this time the solvents were removed under vacuum to leave a residue which was purified on silica gel column using dichloromethane/ethyl acetate (1:0 to 5:1) to give 1,5-bis(4-hydroxy-3-methoxyphenyl)-2-methylpentane-1,3-dione (102 mg, 67%) as a light green oil: LCMS (m/z) 359 (M+H)⁺, 381 (M+Na)⁺; ¹H NMR (400 MHz, CDCl₃) δ 1.40 (3H, d, J=7.2 Hz, CH₃), 2.63-2.82 (4H, m, 2×CH₂), 3.81 (3H, s, OCH₃), 3.94 (3H, s, OCH₃), 4.39 (1H, q, J=7.2 Hz, H-2), 5.45 (1H, brs, OH), 6.13 (1H, brs, OH), 6.58-6.60 (2H, m, 2×ArH), 6.76 (1H, d, J=8.4 Hz, ArH), 6.92 (1H, d, J=8.4 Hz, ArH), 7.44-7.48 (2H, m, 2×ArH) ppm; ¹³C NMR (100 MHz, CDCl₃) δ 13.57, 29.34, 42.17, 55.73, 55.97, 56.13, 110.31, 110.97, 113.98, 114.20, 120.77, 124.08, 128.80, 132.57, 143.81, 146.27, 146.80, 150.95, 195.57, 206.67 ppm.

Example 47

5-(4-Hydroxy-3-methoxyphenyl)-1-(4-methoxyphenyl)-2-methyl-pentane-1,3-dione (Compound 17)

By a similar procedure as described in Example 31, but starting from compound 49, 5-(4-hydroxy-3-methoxyphenyl)-1-(4-methoxyphenyl)-2-methyl-pentane-1,3-dione (0.132 g, 44%) was obtained as a yellow oil: LRMS (m/z) 341 (M−H)⁺; ¹H NMR (300 MHz, CDCl₃) δ 1.38 (3H, d, J=7.2 Hz, CHCH₃), 2.64-2.82 (4H, m, CH₂CH₂), 3.78 (3H, s, OCH₃), 3.85 (3H, s, OCH₃), 4.37 (1H, q, H-2), 5.57 (1H, s, OH), 6.56-6.57 (2H, m, ArH), 6.74 (1H, d, J=9.0 Hz, ArH), 6.89 (2H, d, J=9.0 Hz, ArH), 7.85 (2H, d, J=8.7 Hz, ArH) ppm; ¹³C NMR (75 MHz, CDCl₃) δ 13.43, 29.30, 42.20, 55.43, 55.73, 56.22, 111.01, 113.90, 114.20, 120.78, 128.92, 130.93, 132.58, 143.85, 146.30, 163.86, 195.60, 206.54 ppm.

Example 48

1-(Biphenyl-4-yl)-5-(4-hydroxy-3-methoxyphenyl)-pentane-1,3-dione (Compound 18)

By a similar procedure as described in Example 31, but starting from compound 50, 1-(biphenyl-4-yl)-5-(4-hydroxy-3-methoxyphenyl)-pentane-1,3-dione (262 mg, 93%) was obtained as a off-white solid: m.p. 118-119° C.; LCMS (m/z) 374 (M⁺), 375 (M+H)⁺; ¹H NMR (400 MHz, CDCl₃) δ 2.73-2.77 (2H, m, CH₂), 2.96-2.99 (2H, m, CH₂), 3.88 (3H, s, OCH₃), 5.53 (1H, brs, H-2 or OH), 6.19 (1H, s, H-2 or OH), 6.74-6.76 (2H, m, 2×ArH), 6.87 (1H, d, J=8.4 Hz, ArH), 7.39-7.50 (3H, m, 3×ArH), 7.63-7.70 (4H, m, 4×ArH), 7.95 (2H, brd, J=8.4 Hz, 2×ArH), 16.23 (1H, brs, OH) ppm; ¹³C NMR (100 MHz, CDCl₃) δ 31.42, 41.36, 55.85, 96.38, 110.98, 114.34, 120.83, 127.16, 127.23, 127.51, 128.12, 128.92, 132.63, 133.54, 139.88, 143.99, 145.06, 146.41, 182.77, 195.80 ppm.

Example 49

1-(Biphenyl-2-yl)-5-(4-hydroxy-3-methoxyphenyl)-pentane-1,3-dione (Compound 19)

By a similar procedure as described in Example 31, but starting from compound 51, 1-(biphenyl-2-yl)-5-(4-hydroxy-3-methoxyphenyl)-pentane-1,3-dione (283 mg, 96%) was obtained as a dark yellow oil: LCMS (m/z) 375 (M+H)$^+$, 749 (2M+Na)$^+$; $^1$H NMR (400 MHz, CDCl$_3$) δ 2.40-2.44 (2H, m, CH$_2$), 2.66-2.70 (2H, m, CH$_2$), 3.86 (3H, s, OCH$_3$), 5.34 (1H, s, H-2 or OH), 5.57 (1H, brs, H-2 or OH), 6.59-6.64 (2H, m, 2×ArH), 6.84 (1H, d, J=8.0 Hz, ArH), 7.33-7.46 (7H, m, 7×ArH), 7.53 (1H, td, J=8.0, 2.0 Hz, ArH), 7.68 (1H, dd, J=8.0, 2.0 Hz, ArH), 15.62 (1H, brs, OH) ppm; $^{13}$C NMR (100 MHz, CDCl$_3$) δ 31.35, 40.46, 55.77, 102.04, 110.77, 114.23, 120.68, 127.39, 128.27, 128.79, 128.94, 130.68, 132.43, 135.88, 140.76, 141.02, 143.90, 146.31, 188.28, 192.75 ppm.

Example 50

1-(4-Fluorophenyl)-5-(4-hydroxy-3-methoxyphenyl)-pentane-1,3-dione (Compound 20)

By a similar procedure as described in Example 31, but starting from compound 52, 1-(4-fluorophenyl)-5-(4-hydroxy-3-methoxyphenyl)-pentane-1,3-dione (256 mg, 82%) was obtained as a dark yellow solid: m. p. 56-57° C.; $^1$H NMR (400 MHz, CDCl$_3$) δ 2.70-2.74 (2H, m, CH$_2$), 2.93-2.97 (2H, m, CH$_2$), 3.87 (3H, s, OCH$_3$), 5.58 (1H, brs, H-2 or OH), 6.10 (1H, s, H-2 or OH), 6.72-6.74 (2H, m, 2×ArH), 6.86 (1H, d, J=8.4 Hz, ArH), 7.13 (2H, t, J=8.4 Hz, 2×ArH), 7.85-7.90 (2H, m, 2×ArH), 16.12 (1H, brs, OH) ppm; $^{13}$C NMR (100 MHz, CDCl$_3$) δ 31.40, 41.04, 55.79, 96.08, 110.92, 114.31, 115.61, 115.83, 120.78, 129.35, 129.44, 131.11, 131.14, 132.49, 143.96, 146.38, 163.99, 166.52, 182.76, 194.99 ppm.

Example 51

Methyl 4-(5-(4-hydroxy-3-methoxyphenyl)-3-oxopentanoyl)benzoate (Compound 25)

By a similar procedure as described in Example 31, but starting from compound 57, methyl 4-(5-(4-hydroxy-3-methoxyphenyl)-3-oxopentanoyl)benzoate (14 mg, 30%) was obtained as a yellow solid: LCMS (m/z) 355 (M−H)$^+$; $^1$H NMR (400 MHz, CDCl$_3$) δ 2.74-2.78 (2H, m, CH$_2$), 2.94-2.98 (2H, m, CH$_2$), 3.87 (3H, s, OCH$_3$), 3.95 (3H, s, OCH$_3$), 6.17 (1H, brs, OH), 6.67-6.74 (2H, m, 2×ArH), 6.85 (1H, d, J=8.8 Hz, ArH), 7.90 (2H, d, J=8.5 Hz, 2×ArH), 8.10 (2H, d, J=8.5 Hz, 2×ArH), 16.09 (1H, brs, OH) ppm; $^{13}$C NMR (100 MHz, CDCl$_3$) δ 31.23, 41.69, 52.36, 55.88, 97.26, 111.01, 114.40, 120.86, 126.84, 129.78, 132.46, 133.17, 138.63, 144.10, 146.46, 166.26, 180.81, 197.46 ppm.

Example 52

5-(4-Hydroxy-3-methoxyphenyl)-1-(naphthalene-2-yl)-pentane-1,3-dione (Compound 26)

By a similar procedure as described in Example 31, but starting from compound 58, 5-(4-hydroxy-3-methoxyphenyl)-1-(naphthalene-2-yl)-pentane-1,3-dione (298 mg, 94%) was obtained as an off-white solid: m.p. 101-102° C.; LCMS (m/z) 349 (M+H)$^+$, 697 (2M+H)$^+$, 719 (2M+Na)$^+$; $^1$H NMR (400 MHz, CDCl$_3$) δ 2.76-2.80 (2H, m, CH$_2$), 2.98-3.02 (2H, m, CH$_2$), 3.88 (3H, s, OCH$_3$), 5.55 (1H, brs, H-2 or OH), 6.30 (1H, s, H-2 or OH), 6.75-6.77 (2H, m, 2×ArH), 6.88 (1H, d, J=8.4 Hz, ArH), 7.53-7.61 (2H, m, ArH), 7.87-7.96 (4H, m, 4×ArH), 8.42 (1H, brs, ArH), 16.26 (1H, brs, OH) ppm; $^{13}$C NMR (100 MHz, CDCl$_3$) δ 31.45, 41.41, 55.84, 96.76, 111.01, 114.36, 120.85, 123.04, 126.75, 127.72, 128.06, 128.15, 128.39, 129.27, 132.04, 132.65, 132.65, 135.21, 144.01, 146.42, 183.02, 195.86 ppm.

Example 53

5-(4-Hydroxy-3-methoxylphenyl)-1-(naphthalene-1-yl)-pentane-1,3-dione (Compound 27)

By a similar procedure as described in Example 31, but starting from compound 59, 5-(4-hydroxy-3-methoxyphenyl)-1-(naphthalene-1-yl)-pentane-1,3-dione (283 mg, 96%) was obtained as a dark yellow oil: LCMS (m/z) 349 (M+H)$^+$, 719 (2M+Na)$^+$; $^1$H NMR (400 MHz, CDCl$_3$) δ 2.71-2.76 (2H, m, CH$_2$), 2.96-3.01 (2H, m, CH$_2$), 3.87 (3H, s, OCH$_3$), 5.57 (1H, brs, H-2 or OH), 5.99 (1H, s, H-2 or OH), 6.75-6.77 (2H, m, 2×ArH), 6.89 (1H, d, J=8.4 Hz, ArH), 7.48-7.50 (3H, m, 3×ArH), 7.69 (1H, dd, J=7.2, 1.2 Hz, ArH), 7.88 (1H, m, ArH), 7.96 (1H, brd, J=8.0 Hz, ArH), 8.35-8.38 (1H, m, ArH), 16.23 (1H, brs, OH) ppm; $^{13}$C NMR (100 MHz, CDCl$_3$) δ 31.52, 40.87, 55.84, 101.64, 110.96, 114.35, 120.86, 124.74, 125.42, 126.33, 126.97, 127.19, 128.48, 130.01, 131.66, 132.46, 133.73, 134.20, 144.00, 146.40, 188.15, 194.33 ppm.

Example 54

2,2-Dimethyl-5-(4-hydroxy-3-methoxy-phenyl)-1-phenyl-pentane-1,3-dione (Compound 32)

By a similar procedure as described in Example 31, but starting from compound 64, 2,2-dimethyl-5-(4-hydroxy-3-methoxy-phenyl)-1-phenyl-pentane-1,3-dione (126 mg, 65%) was obtained as a clear oil: LRMS (m/z) 325 (M−H)$^+$; $^1$H NMR (300 MHz, CDCl$_3$) δ 1.42 (6H, s, 2×CH$_3$), 2.64 (2H, t, J=6.6 Hz, CH$_2$), 2.76 (2H, t, J=6.6 Hz, CH$_2$), 3.75, (3H, s, OCH$_3$), 5.49 (1H, s, OH), 6.51 (2H, m, ArH), 6.72 (1H, d, J=8.1 Hz, ArH), 7.30 (2H, t, J=7.2 Hz, ArH) 7.48 (1H, t, J=7.5 Hz, ArH), 7.66 (2H, d, J=6.9 Hz, ArH) ppm; $^{13}$C NMR (75 MHz, CDCl$_3$) δ 23.10, 29.60, 41.11 55.76, 61.04, 110.99, 114.21, 121.04, 128.54, 128.84, 132.42, 132.80, 135.42, 143.94, 146.30, 199.43, 209.53 ppm.

Example 55

(E)-1-(4-Hydroxy-3-methoxyphenyl)-4,4,6,6-tetramethylhept-1-ene-3,5-dione (Compound 91)

To a solution of compound 34 (700 mg, 2.53 mmol) dissolved in anhydrous DMF (25 ml) was added imidazole (207 mg, 3.04 mmol) and tert-butyldimethylsilyl chloride (458 mg, 3.04 mmol). The mixture was stirred at room temperature under N$_2$ for 18 h. The solvents were removed in vacuo and the residue taken up in dichloromethane (50 ml); washed with sat. aq NH$_4$Cl (50 ml); dried over anhydrous MgSO$_4$ (MgSO$_{4(anh)}$), filtered and concentrated in vacuo to give a residue. Purification by column chromatography on silica using dichloromethane/petrol (3:2→1:0) as eluent gave (E)-1-(4- tert-butyldimethylsilyloxy-3-methoxyphenyl)-6,6-dimethylhept-1-ene-3,5-dione (711 mg, 71%) as a yellow oil: $^1$H NMR (400 MHz, CDCl$_3$) δ 0.17 (6H, s, Si(CH$_3$)$_2$), 0.99 (9H, s, SiC(CH$_3$)$_3$), 1.20 (9H, s, C(CH$_3$)$_3$), 3.83 (3H, s, OCH$_3$), 5.77 (1H, s, enol CH or phenol OH), 6.39 (1H, d, J=16.0 Hz, vinyl CH), 6.83 (1H, d, J=8.0 Hz, ArH), 7.01-7.03 (2H, m, 2×ArH), 7.51 (1H, d, J=16.0 Hz, vinyl CH), 15.80 (1H, br s, enol OH) ppm.

To a stirring solution of (E)-1-(4-tert-butyldimethylsilyloxy-3-methoxyphenyl)-6,6-dimethylhept-1-ene-3,5-dione (700 mg, 1.79 mmol) in THF (15 ml) under N$_2$ was added potassium tert-butoxide (442 mg, 3.94 mmol) and stirred for a further 45 min at room temperature. A solution of methyl iodide (0.235 ml, 3.76 mmol) in THF (2 ml) was added and the mixture heated at reflux for 5 h. Water (25 ml) was added to the cooled mixture followed by DCM (25 ml). The organic layer was separated, washed with water (25 ml), dried (MgSO$_{4(anh)}$), filtered and concentrated. The residue was purified by column chromatography on silica using dichloromethane as eluent to give the monomethyl alkylated product, (E)-1-(4-tert-butyldimethylsilyloxy-3-methoxyphenyl)-4,6,6-trimethylhept-1-ene-3,5-dione (540 mg, 74%):

$^1$H NMR (400 MHz, CDCl$_3$) δ 0.08 (6H, s, Si(CH$_3$)$_2$), 0.90 (9H, s, SiC(CH$_3$)$_3$), 1.08 (9H, s, C(CH$_3$)$_3$), 1.29 (3H, d, J=7.0 Hz, OCHC(CH$_3$)CO), 3.76 (3H, s, OCH$_3$), 4.21 (1H, q, J=7.0 Hz, OCCH(CH$_3$)CO), 6.67 (1H, d, J=15.6 Hz, vinyl CH), 6.76 (1H, d, J=8.0 Hz, ArH), 6.96 (1H, d, J=2.0 Hz, ArH), 6.99 (1H, dd, J=8.0, 2.0 Hz, ArH), 7.51 (1H, d, J=15.6 Hz, vinyl CH) ppm.

To a stirring solution of (E)-1-(4-tert-butyldimethylsilyloxy-3-methoxyphenyl)-4,6,6-trimethylhept-1-ene-3,5-dione (540 mg, 1.33 mmol) in THF (10 ml) under N$_2$ was added sodium hydride (64 mg (of 60%), 1.60 mmol) and stirred for a further 45 min at room temperature. A solution of methyl iodide (0.1 ml, 1.60 mmol) in THF (1 ml) was added and the mixture heated at reflux for 5 h. Water (25 ml) was added to the cooled mixture followed by DCM (25 ml). The organic layer was separated, washed with water (25 ml), dried (MgSO$_{4(anh)}$), filtered and concentrated. The residue was purified by column chromatography on silica using dichloromethane as eluent to give (E)-1-(4-tert-butyldimethylsilyloxy-3-methoxyphenyl)-4,4,6,6-tetramethylhept-1-ene-3,5-dione (266 mg, 48%) as a yellow oil: $^1$H NMR (400 MHz, CDCl$_3$) δ 0.17 (6H, s, Si(CH$_3$)$_2$), 0.99 (9H, s, SiC(CH$_3$)$_3$), 1.18 (9H, s, C(CH$_3$)$_3$), 1.41 (6H, s, 2×C(CH$_3$)), 3.83 (3H, s, OCH$_3$), 6.54 (1H, d, J=15.6 Hz, vinyl CH), 6.84 (1H, d, J=8.0 Hz, ArH), 6.98 (1H, d, J=2.0 Hz, ArH), 7.06 (1H, dd, J=8.0, 2.0 Hz, ArH), 7.66 (1H, d, J=15.6 Hz, vinyl CH) ppm.

(E)-1-(4-tert-butyldimethylsilyloxy-3-methoxyphenyl)-4,4,6,6-tetramethylhept-1-ene-3,5-dione (266 mg, 0.635 mmol) was dissolved in anhydrous THF (10 ml) and stirred at room temperature under a nitrogen atmosphere. TBAF (0.22 ml, 0.76 mmol) was added (yellow/green solution goes deep red colour) and the mixture was stirred overnight at room temperature. After this time the solvents were removed under vacuum to leave a residue which was purified by column chromatography on silica using dichloromethane/diethyl ether (1:0 to 10:1) to give (E)-1-(4-hydroxy-3-methoxyphenyl)-4,4,6,6-tetramethylhept-1-ene-3,5-dione (177 mg, 92%) as a dark yellow oil: $^1$H NMR (400 MHz, CDCl$_3$) δ 1.19 (9H, s, C(CH$_3$)$_3$), 1.42 (6H, s, 2×C(CH$_3$)), 3.93 (3H, s, OCH$_3$), 6.03 (1H, brs, phenol OH), 6.54 (1H, d, J=15.6 Hz, vinyl CH), 6.92 (1H, d, J=8.0 Hz, ArH), 6.99 (1H, d, J=2.0 Hz, ArH), 7.12 (1H, dd, J=8.0, 2.0 Hz, ArH), 7.66 (1H, d, J=15.6 Hz, vinyl CH) ppm.

Example 56

(E)-5-(4-hydroxy-3-methoxyphenyl)-2,2-dimethyl-1-(1-methyl-cyclopropyl)pent-4-ene-1,3-dione (Compound 90)

Imidazole (298 mg, 4.37 mmol) and tert-butyldimethylsilyl chloride (659 mg, 4.37 mmol) were added to a solution of compound 38 (1.0 g, 3.65 mmol) in anhydrous DMF (30 ml). The mixture was stirred at room temperature under a nitrogen atmosphere for 18 h. The solvents were removed in vacuo and the residue taken up in DCM (25 ml). The solution was washed with sat. aq. NH$_4$Cl (25 ml), dried over MgSO$_{4(anh)}$, filtered and concentrated in vacuo to give a residue. Purification by column chromatography on silica using DCM/petroleum ether (1:1→3:2) as eluent gave (E)-5-(4-tert-butyldimethylsilyloxy-3-methoxy-phenyl)-1-(1-methylcyclo-propyl)pentane-1,3-dione (1.4 g, 99%) as a yellow oil: $^1$H NMR (400 MHz, CDCl$_3$) δ 0.15 (6H, s, SiCH$_3$)$_2$), 0.77 (2H, q, J=3.5 Hz, cyclopropyl CH$_2$), 0.97 (9H, s, SiC(CH$_3$)$_3$), 1.31 (2H, q, J=3.5 Hz, cyclopropyl CH$_2$), 1.35 (3H, s, CH$_3$), 3.82 (3H, s, OCH$_3$), 5.70 (1H, s, enol CH), 6.34 (1H, d, J=16.0 Hz, vinyl CH), 6.82 (1H, d, J=8.0 Hz, ArH), 6.99-7.02 (2H, m, 2×ArH), 7.50 (1H, d, J=16.0 Hz, vinyl CH), 15.90 (1H, br s, enol OH) ppm.

To a stirring solution (E)-5-(4-tert-butyldimethylsilyloxy-3-methoxy-phenyl)-1-(1-methylcyclo-propyl)pentane-1,3-dione (1.4 g, 3.6 mmol) in anhydrous THF (35 ml) under N$_2$ was added NaH (317 mg (60%), 7.93 mmol). Stirring was continued for a further 45 min at room temperature. To this solution was added MeI (0.47 ml, 7.57 mmol) and the mixture heated at reflux for 5 h. DCM (35 ml) was added to the cooled mixture followed by water (35 ml). The organic layer was separated, washed with water (35 ml), dried (MgSO$_{4(anh)}$), filtered and concentrated in vacuo. The residue was purified by column chromatography on silica using petroleum ether/EtOAc (100:0→95:5) as eluent to give (E)-5-(4-tert-butyldimethylsilyloxy-3-methoxy-phenyl)-2,2-dimethyl-1-(1-methylcyclopropyl)pentane-1,3-dione (1.25 g, 84%) as a yellow oil:

$^1$H NMR (400 MHz, CDCl$_3$) δ 0.16 (6H, s, SiCH$_3$)$_2$), 0.62 (2H, q, J=3.5 Hz, cyclopropyl CH$_2$), 0.98 (9H, s, SiC(CH$_3$)$_3$), 1.26 (3H, s, CH$_3$), 1.29 (2H, q, J=3.5 Hz, cyclopropyl CH$_2$), 1.40 (6H, s, O=CC(CH$_3$)$_2$), 3.83 (3H, s, OCH$_3$), 6.60 (1H, d, J=16.0 Hz, vinyl CH), 6.84 (1H, d, J=8.0 Hz, ArH), 7.00 (1H, d, J=2.0 Hz, ArH), 7.07 (1H, dd, J=8.0, 2.0 Hz, ArH), 7.69 (1H, d, J=16.0 Hz, vinyl CH) ppm.

(E)-5-(4-tert-butyldimethylsilyloxy-3-methoxy-phenyl)-2,2-dimethyl-1-(1-methylcyclopropyl)-pentane-1,3-dione (1.25 g, 3.22 mmol) was dissolved in anhydrous THF (30 ml) and stirred at room temperature under a N$_2$ atmosphere. TBAF (3.86 ml, 3.86 mmol) was added (yellow/green solution goes deep red colour) and the mixture was stirred overnight at room temperature. After this time, the solvents were removed in vacuo to leave a residue which was purified by column chromatography on silica using DCM as eluent to give compound 90 (770 mg, 80%) as a yellow oil: LCMS 303 [M+H]$^+$, 301 [M−H]$^+$; $^1$H NMR (400 MHz, CDCl$_3$) δ 0.62 (2H, q, J=3.5 Hz, cyclopropyl CH$_2$), 1.26 (3H, s, CH$_3$), 1.29 (2H, q, J=3.5 Hz, cyclopropyl CH$_2$), 1.41 (6H, s, O=CC(CH$_3$)$_2$), 3.92 (3H, s, OCH$_3$), 6.21 (1H, brs, phenol OH), 6.60 (1H, d, J=15.5 Hz, vinyl CH), 6.93 (1H, d, J=8.0 Hz, ArH), 7.01 (1H, d, J=2.0 Hz, ArH), 7.12 (1H, dd, J=8.0, 2.0 Hz, ArH), 7.69 (1H, d, J=15.5 Hz, vinyl CH) ppm: $^{13}$C NMR (100 MHz, CDCl$_3$) δ 20.34, 20.44, 22.09, 25.58, 26.29, 55.96, 60.98, 109.81, 114.85, 119.27, 123.73, 126.68, 144.29, 146.81, 148.55, 197.83, 210.68 ppm.

Example 57

1-(4-Fluorophenyl)-5-(4-hydroxy-3-methoxyphenyl)-2,2-dimethylpentane-1,3-dione (Compound 73)

Toluene (12 ml) was added to compound 93 (249 mg, 0.56 mmol) and 10% palladium on carbon (16 mg) and subjected to a balloon pressure of hydrogen with stirring for 18 h. The suspension was filtered through a pad of silica gel and flushed through with ethyl acetate. Evaporation of the solvent in vacuo gave a residue which was purified by column chromatography on silica using DCM as eluent to give 1-(4-fluorophenyl)-5-(4-hydroxy-3-methoxyphenyl)-2,2-dimethylpentane-1,3-dione (203 mg, 82%) as a brown oil: LCMS 343 [M−H]$^+$; $^1$H NMR (400 MHz, CDCl$_3$) δ 1.43 (6H, s, 2×C (CH$_3$)), 2.63-2.67 (2H, m, CH$_2$), 2.76-2.80 (2H, m, CH$_2$), 3.76 (3H, s, OCH$_3$), 5.50 (1H, br s, phenol OH), 6.49 (1H, d, J=2.0 Hz, ArH), 6.55 (1H, dd, J=8.0, 2.0 Hz, ArH), 6.74 (1H, d, J=8.0 Hz, ArH), 6.99 (2H, brt, J=8.5 Hz, 2×ArH), 7.68 (2H, q, J=5.5 Hz, 2×ArH) ppm; $^{13}$C NMR (100 MHz, CDCl$_3$) δ 23.09, 29.47, 41.00, 55.70, 61.02, 110.87, 114.15, 115.55, 115.77, 121.07, 131.54, 131.63, 132.24, 143.94, 146.23, 164.07, 166.61, 197.65, 209.56 ppm.

Example 58

5-(4-(2-Aminoethoxy)-3-methoxyphenyl)-1-phenylpentane-1,3-dione hydrochloride (Compound 88)

To a solution of compound 68 (0.42 g, 1.42 mmol) in acetonitrile (15 ml) was added 2-(Boc-amino)ethyl bromide (0.35 g, 1.56 mmol) and potassium carbonate (0.294 g, 2.13 mmol). The reaction mixture was refluxed for 1 h. After this time the solution was allowed to cool then diluted with chloroform (20 ml) and washed with sat. aq. sodium bicarbonate (25 ml) and brine (25 ml). The organic layer was separated, dried (MgSO$_{4(anh)}$), filtered and concentrated. The remaining residue was purified by column chromatography on silica using dichloromethane, then petrol/ethyl acetate (9:1→7:3) to give (E)-5-(4-(2-boc-aminoethoxy)-3-methoxyphenyl)-1-phenylpent-4-ene-1,3-dione (275 mg, 44%) as a foamy solid: $^1$H NMR (400 MHz, CDCl$_3$) δ 1.46 (9H, s, O═CO(CH$_3$)$_3$), 3.55-3.59 (2H, m, NHCH$_2$), 3.93 (3H, s, OCH$_3$), 4.10-4.16 (2H, m, NHCH$_2$), 5.14 (1H, brs, NH), 6.35 (1H, s, enol CH), 6.54 (1H, d, J=16.0 Hz, vinyl CH), 6.91 (1H, d, J=8.4 Hz, ArH), 7.10 (1H, d, J=1.6 Hz, ArH), 7.14 (1H, dd, J=8.4, 1.6 Hz, ArH), 7.46-7.56 (3H, m, 3×ArH), 7.64 (1H, d, J=16.0 Hz, vinyl CH), 7.96 (2H, d, J=8.4 Hz, ArH), 16.23 (1H, brs, enol OH) ppm.

Toluene (10 ml) and pyridine (0.14 ml) were added to (E)-5-(4-(2-boc-aminoethoxy)-3-methoxyphenyl)-1-phenylpent-4-ene-1,3-dione (275 mg, 0.63 mmol) and 10% palladium on carbon (14 mg) and subjected to a balloon pressure of hydrogen with stirring for 18 h. The suspension was filtered through a pad of silica gel and flushed through with ethyl acetate. Evaporation of the solvent under reduced pressure gave a residue which was purified by column chromatography on silica using petrol/ethyl acetate (9:1→7:3) to give (211 mg, 77%) as a yellow oil: LCMS 442 [M+H]$^+$, 464 [M+Na]$^+$; $^1$H NMR (400 MHz, CDCl$_3$) δ 1.45 (9H, s, O═CO (CH$_3$)$_3$), 2.72-2.76 (2H, m, CH$_2$), 2.95-2.99 (2H, m, CH$_2$), 3.51 (2H, q, J=5.0 Hz, NHCH$_2$), 3.85 (3H, s, OCH$_3$), 4.05 (2H, t, J=5.0 Hz, NHCH$_2$CH$_2$), 5.23 (1H, brs, NH), 6.15 (1H, s, enol CH), 6.74-6.85 (3H, m, 3×ArH), 7.43-7.55 (3H, m, 3×ArH), 7.85-7.87 (2H, m, 2×ArH), 16.15 (1H, br s, enol OH) ppm.

To a solution of 5-(4-(2-boc-aminoethoxy)-3-methoxyphenyl)-1-phenylpentane-1,3-dione (211 mg, 0.48 mmol) dissolved in dioxane (5 ml) was added drop wise dry HCl in dioxane (4 M, 0.36 ml, 1.43 mmol) and stirred at RT for 1 h. After this time diethyl ether (20 ml) was added and an off-white emulsion was visible. The solvents were removed by evaporation in vacuo to give a brown gum residue. Residual dioxane was removed by azeotroping with methanol and then drying the product on high pressure line to give 5-(4-(2-aminoethoxy)-3-methoxyphenyl)-1-phenylpentane-1,3-dione hydrochloride (163 mg, 99%) as a brown powdery solid: mp 80° C.; LCMS 342 [M+H]$^+$, 364 [M+Na]$^+$, $^1$H NMR (400 MHz, MeOD) δ 2.79-2.82 (2H, m, CH$_2$), 2.99-3.02 (2H, m, CH$_2$), 3.33-3.34 (2H, m, NHCH$_2$+solvent signal), 3.90 (3H, s, OCH$_3$), 4.20 (2H, t, J=5.0 Hz, NHCH$_2$CH$_2$), 6.37 (1H, s, enol CH), 6.84-6.98 (3H, m, 3×ArH), 7.48-7.60 (3H, m, 3×ArH), 7.93 (2H, d, J=8.0 Hz, 2×ArH) ppm; $^{13}$C NMR (100 MHz, MeOD) δ 33.04, 41.40, 41.83, 57.31, 68.16, 98.35, 114.54, 117.51, 122.73, 128.84 (2×CH), 130.58 (2×CH), 134.34, 136.75, 137.93, 147.75, 151.73, 184.57, 198.44 ppm.

Example 59

5-(4-(2-aminoethoxy)-3-methoxyphenyl)-1-phenylpentane-1,3-dione hydrochloride (Compound 87)

To a solution of compound 32 (0.55 g, 1.69 mmol) in acetonitrile (20 ml) was added 2-(Boc-amino)ethyl bromide (0.415 g, 1.85 mmol) and potassium carbonate (0.35 g, 2.5 mmol). The reaction mixture was heated at reflux for 1 h. After this time, the solution was allowed to cool then diluted with chloroform (25 ml) and washed with sat. aq. sodium bicarbonate (25 ml) and brine (25 ml). The organic layer was separated, dried (MgSO$_{4(anh)}$), filtered and concentrated in vacuo. The residue was purified by column chromatography on silica using dichloromethane, then petroleum ether/ethyl acetate (9:1→7:3) to give (380 mg, 48%) as a brown oil: $^1$H NMR (400 MHz, CDCl$_3$) δ 1.44 (15H, br s, O═CO(CH$_3$)$_3$ and NHCOOC(CH$_3$)$_3$), 2.63-2.67 (2H, m, CH$_2$), 2.76-2.79 (2H, m, CH$_2$), 3.49 (2H, d, J=5.0 Hz, NHCH$_2$), 3.75 (3H, s, OCH$_3$), 4.00 (2H, t, J=5.0 Hz, NHCH$_2$), 4.41 (1H, t, J=8.0 Hz, NH), 5.22 (1H, brs, NH), 6.53-6.56 (2H, m, 2×ArH), 6.72 (1H, d, J=8.0 Hz, ArH), 7.34 (2H, brt, J=8.0 Hz, 2×ArH), 7.50 (1H, t, J=8.0 Hz, ArH), 7.68 (2H, d, J=8.0 Hz, ArH) ppm.

To a solution of 5-(4-(2-N-boc-aminoethoxy)-3-methoxyphenyl)-2,2-dimethyl-1-phenylpent-4-ene-1,3-dione (200 mg, 0.42 mmol) in dioxane (2 ml) was added drop wise dry HCl in dioxane (4 M, 0.425 ml, 1.68 mmol). The reaction was stirred at RT for 1 h, after which diethyl ether (20 ml) was added and an off-white emulsion became visible. The solvents were removed by evaporation in vacuo to give a clear gum residue. Residual dioxane was removed by azeotroping with methanol and then drying the product under high vacuum to give 5-(4-(2-aminoethoxy)-3-methoxyphenyl)-1-phenylpentane-1,3-dione hydrochloride (170 mg, 99%) as an off-white foamy solid: LCMS 370 [M+H]$^+$, 392 [M+Na]$^+$; actual MW 369 (free base), 404.5 (HCl salt); $^1$H NMR (400

MHz, d$_4$-MeOD) δ 1.38 (6H, s, O=CC(CH$_3$)$_2$), 2.78 (4H, s, 2×CH$_2$), 3.29-3.33 (2H, m, NHCH$_2$+solvent signal), 3.76 (3H, s, OCH$_3$), 4.16 (2H, t, J=5.0 Hz, NHCH$_2$CH$_2$), 6.63 (1H, dd, J=8.0, 2.0 Hz, ArH), 6.72 (1H, d, J=2.0 Hz, ArH), 6.85 (1H, d, J=8.0 Hz, ArH), 7.33-7.36 (2H, m, 2×ArH), 7.49-7.58 (1H, m, ArH), 7.58 (2H, dd, J=8.0, 2.0 Hz, 2×ArH) ppm; $^{13}$C NMR (100 MHz, MeOD) δ 19.32, 24.54, 31.17, 41.49, 42.52, 57.28, 62.79, 68.22, 114.67, 117.48, 123.01, 130.54, 130.75, 134.84, 137.72, 138.08, 147.74, 151.73, 202.17, 212.15 ppm. No melting point was recorded due to the hygroscopic nature of this compound.

Example 60

Using procedures detailed in the above Examples, the characterisation data for further compounds are listed in Table 5.

TABLE 5

Other examples of synthesised compounds with their characterisation data

| Compound | Starting material: | Procedure: | Yield: | m.p.: |
|---|---|---|---|---|
| 94 | (E)-1-(2-Chlorophenyl)-5(4-hydroxy-3-methoxyphenyl)pent-4-ene-1,3-dione | | | |
| | 2-chlorobenzoic acid | as Example 10 | 32% | |
| | Spectral data: LCMS 331 [M + H]$^+$; $^1$H NMR (400 MHz, CDCl$_3$) δ 3.96 (3H, s, OCH$_3$), 5.88 (1H, br s, enol CH or phenol OH), 6.18 (1H, s, enol CH or phenol OH), 6.47 (1H, d, J = 15.5 Hz, vinyl CH), 6.95 (1H, d, J = 8.0 Hz, ArH), 7.07 (1H, d, J = 2.0 Hz, ArH), 7.14 (1H, dd, J = 8.0 and 2.0 Hz, ArH), 7.34-7.50 (3H, m, 3 × ArH), 7.64 (1H, d, J = 15.5 Hz, vinyl CH), 7.63-7.66 (1H, m, ArH), 15.70 (1H, br s, enol OH) ppm; $^{13}$C NMR (100 MHz, CDCl$_3$) δ 55.97, 101.99, 109.51, 114.83, 120.44, 123.05, 126.92, 127.56, 129.95, 130.62, 131.56 (2 × CH), 137.07, 140.90, 146.79, 147.95, 179.29, 189.99 ppm. | | | |
| 95 | (E)-1-(4-Chloro-3-methylphenyl)-5-(4-hydroxy-3-methoxyphenyl)pent-4-ene-1,3-dione | | | |
| | 4-chloro-3-methyl benzoic acid | as Example 10 | 17% | |
| | Spectral data: LCMS [M − H]$^+$ 343; $^1$H NMR (400 MHz CDCl$_3$) δ 2.43 (3H, s, CH$_3$), 3.92 (3H, s, OCH$_3$), 5.89 (1H, s, enol CH or phenol OH) 6.26 (1H, s, enol CH or phenol OH), 6.48 (1H, d, CH=CH), 6.92 (1H, d, ArH), 7.04 (1H, s, ArH), 7.10 (1H, d, ArH), 7.42 (1H, d, ArH), 7.59 (1H, d, CH=CH), 7.68 (1H, d, ArH), 7.80 (1H, s, ArH) ppm. | | | |
| 96 | (E)-1-(4-Chloro-2-methylphenyl)-5-(4-hydroxy-3-methoxyphenyl)pent-4-ene-1,3-dione | | | |
| | 4-chloro-2-methyl-benzoic acid | as Example 10 | 15% | |
| | Spectral data: LCMS 345, 343 [M]$^+$; $^1$H NMR (400 MHz, CDCl$_3$) δ 2.45 (3H, s, PhCH$_3$), 3.88 (3H, s, OCH$_3$), 5.81 (1H, br s, enol CH or phenol OH), 5.89 (1H, s, enol CH or phenol OH), 6.37 (1H, d, J = 15.6 Hz, vinyl CH), 6.87 (1H, d, J = 8.0 Hz, ArH), 6.98 (1H, d, J = 2.0 Hz, ArH), 7.06 (1H, dd, J = 8.0, 2.0 Hz, ArH), 7.13-7.19 (2H, m, 2 × ArH), 7.40 (1H, d, J = 8.0 Hz, ArH), 7.55 (1H, d, J = 15.6 Hz, vinyl CH), 15.89 (1H, br s, enol OH) ppm; $^{13}$C NMR (100 MHz, CDCl$_3$) δ 20.61, 55.95, 100.91, 109.51, 114.84, 120.53, 122.93, 125.90, 127.55, 129.56, 131.38, 135.82, 136.48, 139.22, 140.61, 146.79, 147.91, 179.65, 192.23 ppm. | | | |
| 97 | (E)-1-(3-Chloro-2-methylphenyl)-5-(4-hydroxy-3-methoxyphenyl)pent-4-ene-1,3-dione | | | |
| | 3-chloro-2-methyl-benzoic acid | as Example 10 | 26% | |
| | Spectral data: LCMS 345, 343 [M]$^+$; $^1$H NMR (400 MHz, CDCl$_3$) δ 2.53 (3H, s, PhCH$_3$), 3.97 (3H, s, OCH$_3$), 5.92 (1H, br s, enol CH or phenol OH), 6.44 (1H, d, J = 15.6 Hz, vinyl CH), 6.95 (1H, d, J = 8.0 Hz, ArH), 7.06 (1H, d, J = 2.0 Hz, ArH), 7.14 (1H, dd, J = 8.0, 2.0 Hz, ArH), 7.20 (1H, t, J = 8.0 Hz, ArH), 7.37 (1H, d, J = 8.0 Hz, ArH), 7.46 (1H, d, J = 8.0 Hz, ArH), 7.64 (1H, d, J = 15.6 Hz, vinyl CH), 15.81 (1H, br s, enol OH) ppm; $^{13}$C NMR (100 MHz, CDCl$_3$) δ 17.34, 55.96, 101.50, 109.55, 114.86, 120.35, 122.99, 126.28, 126.60, 127.50, 131.11, 134.43, 136.00, 140.13, 140.93, 146.80, 147.99, 179.67, 192.98 ppm. | | | |
| 98 | (E)-1-(3-Chloro-4-methylphenyl)-5-(4-hydroxy-3-methoxyphenyl)pent-4-ene-1,3-dione | | | |
| | 3-chloro-4-methyl benzoic acid | as Example 10 | 20% | |
| | Spectral data: LCMS [M$^+$] 345; $^1$H NMR (400 MHz CDCl$_3$) δ 2.42 (3H, s, CH$_3$), 3.94 (3H, s, OCH$_3$), 5.84 (1H, s, enol CH or phenol OH) 6.25 (1H, s, enol CH or phenol OH), 6.48 (1H, d, CH=CH), 6.93 (1H, d, ArH), 7.04 (1H, s, ArH), 7.10 (1H, d, ArH), 7.42 (1H, d, ArH), 7.59 (1H, d, CH=CH), 7.68 (1H, d, ArH), 7.91 (1H, s, ArH) ppm. | | | |

TABLE 5-continued

Other examples of synthesised compounds with their characterisation data

| Compound | Starting material: | Procedure: | Yield: | m.p.: |
|---|---|---|---|---|
| 101 | (E)-1-(4-Cyanophenyl)-5-(4-hydroxy-3-methoxyphenyl)pent-4-ene-1,3-dione | | | |
| | 4-cyanobenzoic acid | as Example 10 | 31% | |
| | Spectral data: | LCMS 320 [M − H]$^+$; $^1$H NMR (400 MHz, DMSO-d$_6$) δ 3.89 (3H, s, OCH$_3$), 6.85-6.90 (3H, m, 1 × vinyl CH and 2 × ArH), 7.22 (1H, dd, J = 8.4, 2.0 Hz, ArH), 7.37 (1H, d, J = 2.0 Hz, ArH), 7.77 (1H, d, J = 16.0 Hz, vinyl CH), 8.07 (2H, d, J = 8.4 Hz, 2 × ArH), 8.19 (2H, d, J = 8.4 Hz, 2 × ArH), 9.77 (1H, br s, enol OH) ppm; $^{13}$C NMR (100 MHz, DMSO-d$_6$) δ 56.25, 98.10, 111.93, 115.11, 116.37, 118.83, 120.86, 124.07, 126.73, 128.21 (2 × CH), 133.43 (2 × CH), 139.79, 142.86, 148.64, 150.39, 184.00, 184.14 ppm. | | | |
| 102 | (E)-1-(4-tert-Butylphenyl)-5-(4-hydroxy-3-methoxyphenyl)pent-4-ene-1,3-dione | | | |
| | 4-tert-butyl benzoic acid | as Example 10 | 6% | |
| | Spectral data: | LCMS 353 [M + H]$^+$, 375 [M + Na]$^+$; $^1$H NMR (400 MHz, CDCl$_3$) δ 1.36 (9H, s, C(CH$_3$)$_3$), 3.97 (3H, s, OCH$_3$), 5.88 (1H, brs, enol CH or phenol OH), 6.32 (1H, s, enol CH or phenol OH), 6.53 (1H, d, J = 15.5 Hz, vinyl CH), 6.95 (1H, d, J = 8.4 Hz, ArH), 7.08 (1H, d, J = 1.6 Hz, ArH), 7.14 (1H, dd, J = 8.4, 1.6 Hz, ArH), 7.50 (2H, d, J = 8.4 Hz, 2 × ArH), 7.63 (1H, d, J = 15.5 Hz, vinyl CH), 7.90 (2H, d, J = 8.4 Hz, 2 × ArH), 16.33 (1H, brs, enol OH) ppm; $^{13}$C NMR (100 MHz, CDCl$_3$) δ 31.11, 35.08, 55.94, 97.10, 109.48, 114.80, 121.08, 122.79, 125.60 (2 × CH), 127.17 (2 × CH), 127.73, 133.50, 139.99, 146.76, 147.71, 156.22, 179.91, 188.53 ppm. | | | |
| 103 | (E)-5-(4-Hydroxy-3-methoxyphenyl)-1-o-tolylpent-4-ene-1,3-dione | | | |
| | o-toluic acid | as Example 10 | 22% | |
| | Spectral data: | LCMS 311 [M + H]$^+$, $^1$H NMR (400 MHz, CDCl$_3$) δ 2.55 (3H, s, PhCH$_3$), 3.94 (3H, s, OCH$_3$), 6.02 (2H, brs, enol CH and phenol OH), 6.47 (1H, d, J = 16.0 Hz, vinyl CH), 6.94 (1H, d, J = 8.0 Hz, ArH), 7.06 (1H, d, J = 1.6 Hz, ArH), 7.13 (1H, dd, J = 8.0, 1.6 Hz, ArH), 7.24-7.27 (2H, m, 2 × ArH), 7.37 (1H, td, J 8.0, 1.6 Hz, ArH), 7.55 (1H, d, J = 8.0 Hz, ArH), 7.64 (1H, d, J = 16.0 Hz, vinyl CH), 16.08 (1H, brs, enol OH) ppm; $^{13}$C NMR (100 MHz, CDCl$_3$) δ 20.64, 55.87, 101.07, 109.50, 114.81, 120.70, 122.79, 125.66, 127.57, 128.16, 130.62, 131.41, 137.03, 137.30, 140.29, 146.78, 147.81, 179.61, 193.30 ppm | | | |
| 104 | (E)-5-(4-Hydroxy-3-methoxyphenyl)-1-m-tolylpent-4-ene-1,3-dione | | | |
| | m-toluic acid | as Example 10 | 43% | |
| | Spectral data: | LCMS 311 [M + H]$^+$, $^1$H NMR (400 MHz, CDCl$_3$) δ 2.44 (3H, s, PhCH$_3$), 3.96 (3H, s, OCH$_3$), 5.91 (1H, br s, enol CH or phenol OH), 6.33 (1H, s, enol CH or phenol OH), 6.52 (1H, d, J = 16.0 Hz, vinyl CH), 6.95 (1H, d, J = 8.0 Hz, ArH), 7.07 (1H, d, J = 2.0 Hz, ArH), 7.14 (1H, dd, J = 8.0, 2.0 Hz, ArH), 7.35-7.37 (2H, m, 2 × ArH), 7.63 (1H, d, J = 16.0 Hz, vinyl CH), 7.74-7.78 (2H, m, 2 × ArH), 16.30 (1H, brs, enol OH) ppm: $^{13}$C NMR (100 MHz, CDCl$_3$) δ 21.40, 55.93, 97.32, 109.48, 114.81, 121.02, 122.84, 124.42, 127.68, 127.83, 128.48, 133.21, 136.23, 138.38, 140.22, 146.78, 147.80, 180.27, 188.70 ppm. | | | |
| 105 | (E)-5-(2-Chloro-4-hydroxy-5-methoxyphenyl)-1-(naphthalene-3-yl)pent-4-ene-1,3-dione | | | |
| | 2-naphthoyl chloride and (E)-4-(2-chloro-4-hydroxy-5-methoxy-phenyl)but-3-en-2-one (prepared from 2-chloro-4-hydroxy-5-methoxy-benzaldehyde following the method of Denniff, P., Macleod, I., and Whiting, D. A. JCS Perkin I. 82-87 (1979) | as Example 10 | 48% | |
| | Spectral data: | LCMS 381, 379 [M]$^+$, $^1$H NMR (400 MHz, CDCl$_3$) δ 3.98 (3H, s, OCH$_3$), 5.91 (1H, s, phenol OH or enol CH), 6.53 (1H, s, phenol OH or enol CH), 6.57 (1H, d, J = 16.0 Hz, vinyl CH), 7.01 (1H, s, ArH), 7.14 (1H, s, ArH), 7.55-7.63 (2H, m, 2 × ArH), 7.89-7.94 (2H, m, 2 × ArH), 7.98 (1H, d, J = 8.0 Hz, ArH), 8.02 (1H, dd, J = 8.0, 2.0 Hz, ArH), 8.07 (1H, d, J = 16.0 Hz, vinyl CH), 8.51 (1H, s, ArH), 16.26 (1H, brs, enol OH) ppm; $^{13}$C NMR (100 MHz, CDCl$_3$) δ 56.18, 97.67, 108.26, 116.04, 123.27, 123.37, 124.89, 126.77, 127.78, 128.19, 128.38, 128.46, 128.55, 129.40, 132.68, 133.50, 135.36, 135.97, 145.76, 148.02, 179.63, 188.75 ppm. | | | |

TABLE 5-continued

Other examples of synthesised compounds with their characterisation data

| Compound | Starting material: | Procedure: | Yield: | m.p.: |
|---|---|---|---|---|
| 106 | (E)-5-(3-Ethoxy-4-hydroxyphenyl)-1-phenylpent-4-ene-1,3-dione benzoic acid and 1-(4-hydroxy-3-ethoxyphenyl)-but-1-ene-3-one (prepared from ethyl vanillin following the method of Denniff, P., Macleod, I., and Whiting, D. A. JCS Perkin I. 82-87 (1979)) | as Example 10 | 46% | |
| | Spectral data: | LCMS 311 [M + H]$^+$, $^1$H NMR (400 MHz, CDCl$_3$) δ 1.50 (3H, t, J = 7.0 Hz, OCH$_2$CH$_3$), 4.19 (2H, q, J = 7.0 Hz, OCH$_2$CH$_3$), 5.93 (1H, br s, enol CH or phenol OH), 6.33 (1H, s, enol CH or phenol OH), 6.51 (1H, d, J = 16.0 Hz, vinyl CH), 6.96 (1H, d, J = 8.0 Hz, ArH), 7.06 (1H, d, J = 1.6 Hz, ArH), 7.14 (1H, dd, J = 8.0, 1.6 Hz, ArH), 7.46-7.57 (3H, m, 3 × ArH), 7.63 (1H, d, J = 16.0 Hz, vinyl CH), 7.96 (2H, d, J = 8.0 Hz, ArH), 16.28 (1H, brs, enol OH) ppm; $^{13}$C NMR (100 MHz, CDCl$_3$) δ 14.76, 64.55, 97.15, 110.46, 114.76, 120.86, 122.66, 127.20 (2 × CH), 127.55, 128.56 (2 × CH), 132.34, 136.20, 140.43, 146.07, 147.96, 180.52, 188.28 ppm. | | |
| 53 | 1-(4-Chlorophenyl)-5-(4-hydroxy-3-methoxyphenyl)pent-4-ene-1,3-dione 4-chlorobenzoic acid | as Example 10, except using citric acid and dichloromethane in the work-up | 31% | |
| | Spectral data: | MS (+ve): (m/z) 331 MH$^+$; $^1$H NMR (300 MHz, CDCl$_3$) δ 3.94 (3H, s, OCH$_3$), 5.90 (1H, brs, OH), 6.26 (1H, s, enol CH), 6.48 (1H, d, J = 15.9 Hz, CH═CH), 6.93 (1H, d, J = 7.8 Hz, ArH), 7.04 (1H, d, J = 1.8 Hz, ArH), 7.12 (1H, dd, J = 8.4, 1.8 Hz, ArH), 7.42 (2H, d, J = 8.4 Hz, ArH), 7.62 (1H, d, J = 15.9 Hz, CH═CH), 7.86 (2H, d, J = 8.4 Hz, ArH), 16.19 (1H, s, OH) ppm. | | |
| 54 | 1-(3-Chlorophenyl)-5-(4-hydroxy-3-methoxyphenyl)pent-4-ene-1,3-dione 3-chlorobenzoic acid | as Example 10, except using citric acid and dichloromethane in the work-up | 24% | |
| | Spectral data: | MS (+ve): (m/z) 331 MH$^+$; $^1$H NMR (300 MHz, CDCl$_3$) δ 3.94 (3H, s, OCH$_3$), 5.91 (1H, brs, OH), 6.28 (1H, s, enol CH), 6.49 (1H, d, J = 15.3 Hz, CH═CH), 6.92 (1H, d, J = 7.8 Hz, ArH), 7.05 (1H, d, J = 1.8 Hz, ArH), 7.12 (1H, dd, J = 8.1,, 2.1 Hz, ArH), 7.40 (1H, t, J = 8.1 Hz, ArH), 7.48-7.51 (1H, m, ArH), 7.63 (1H, d, J = 15.9 Hz, CH═CH), 16.11 (1H, s, OH) ppm | | |
| 55 | 1-(3,4-Dichlorophenyl)-5-(4-hydroxy-3-methoxyphenyl)pent-4-ene-1,3-dione 3,4-dichlorobenzoic acid | as Example 10, except using citric acid and dichloromethane in the work-up | 27% | |
| | Spectral data: | MS (−ve): (m/z) 363 M$^+$ (−H); $^1$H NMR (300 MHz, CDCl$_3$) δ 3.96 (3H, s, OCH$_3$), 5.88 (1H, brs, OH), 6.25 (1H, s, enol CH), 6.50 (1H, d, J = 15.6 Hz, CH═CH), 6.95 (1H, d, J = 8.4 Hz, ArH), 7.07 (1H, s, ArH), 7.14 (1H, d, J = 7.8 Hz, ArH), 7.55 (1H, d, J = 8.1 Hz, ArH), 7.65 (1H, d, J = 15.9 Hz, CH═CH), 7.76 (1H, d, J = 8.7 Hz, ArH), 8.03 (1H, s, ArH), 16.08 (1H, s, OH) ppm. | | |
| 56 | 1-(2,4-Dichlorophenyl)-5-(4-hydroxy-3-methoxyphenyl)pent-4-ene-1,3-dione 2,4-dichlorobenzoic acid | as Example 10, except using citric acid and dichloromethane in the work-up | 8% | |
| | Spectral data: | MS (+ve): (m/z) 364 MH$^+$; $^1$H NMR (300 MHz, CDCl$_3$) δ 3.95 (3H, s, OCH$_3$), 5.89 (1H, brs, OH), 6.15 (1H, s, enol CH), 6.45 (1H, d, J = 15.9 Hz, CH═CH), 6.93 (1H, d, J = 8.1 Hz, ArH), 7.05 (1H, s, ArH), 7.13 (1H, d, J = 8.4 Hz, ArH), 7.33 (1H, d, J = 8.1 Hz, ArH), 7.47 (1H, s, ArH), 7.57-7.67 (2H, m, CH═CH, ArH), 15.66 (1H, s, OH) ppm. | | |
| 61 | 6-(4-Hydroxy-3-methoxyphenyl)-1-naphthalen-1-yl-hex-5-ene-2,4-dione 1-naphthaleneacetic acid | as Example 10, except using citric acid and dichloromethane in the work-up | 4% | |
| | Spectral data: | MS (−ve): (m/z) 359 M$^+$ (−H); $^1$H NMR (300 MHz, CDCl$_3$) δ 2.05-2.07 (2.5H, m), 2.49 (1.8H, s), 3.34 (1.4H, unresolved m), 3.56-3.57 (1.1H, m), 3.78 (3H, s), 4.19 (2.3H, unresolved m), 4.38 (0.2H, m), 4.83 (0.3H, brs), 5.22 (0.3H, unresolved m), 5.70-5.72 (1.6H, m), 6.40-6.75 (2H, m), 6.76 (0.9H, unresolved m), 7.02 (0.9H, unresolved m), 7.23 (1H, brs), 7.23-7.68 (6.5H, m), 7.70-8.10 (4.4H, m), 8.71 (0.4H, unresolved m), 9.55 (0.9H, unresolved m) ppm. | | |

TABLE 5-continued

Other examples of synthesised compounds with their characterisation data

| Compound | Starting material: | Procedure: | Yield: | m.p.: |
|---|---|---|---|---|
| 62 | 6-(4-Hydroxy-3-methoxyphenyl)-1,1-diphenylhex-5-ene-2,4-dione | | | |
| | diphenyl acetic acid | as Example 10, except using citric acid and dichloromethane in the work-up | 6% | |
| | Spectral data: | MS: (m/z) 387 MH$^+$; $^1$H NMR (300 MHz, CDCl$_3$) δ 2.05 (0.1H, s), 2.19 (1H, s), 2.40 (0.3H, s), 3.70-3.85 (1H, m), 3.93 (3H, s, OCH$_3$), 5.10 (0.9H, brs), 5.31-5.35 (0.6H, m), 5.59 (0.5H, brs), 5.66 (1H, s), 5.88 (0.9H, s), 6.30 (0.9H, d, J = 15.9 Hz, CH=CH), 6.91 (1H, d, J = 8.1 Hz, ArH), 7.01-7.18 (4H, m), 7.25-7.50 (16H, m), 7.53 (1H, d, J = 15.9 Hz, CH=CH), 15.28 (1H, s, OH) ppm | | |
| 63 | 6-(4-Hydroxy-3-methoxyphenyl)-1,1-dimethyl-1-phenyl-hex-5-ene-2,4-dione | | | |
| | 2-methyl-2-phenyl-propionic acid (synthesied from phenylacetic acid) | as Example 10, except using citric acid and dichloromethane in the work-up | 3% | |
| | Spectral data: | MS: (m/z) 339 MH$^+$; $^1$H NMR (300 MHz, CDCl$_3$) δ 1.57 (6.4H, s, 2 × CH$_3$), 1.63 (0.8H, s), 1.73-1.75 (1.6H, m), 3.74 (0.5H, s), 3.81 (0.3H, s), 3.88 (2.64H, s, OCH$_3$), 5.40 (1H, s), 6.20 (1H, d, J = 15.9 Hz, CH=CH), 6.88 (1H, d, J = 8.1 Hz, ArH), 6.93-7.05 (2.3H, m, ArH), 7.15-7.20 (3H, m, ArH), 7.22-7.50 (13H, m, ArH, CH=CH), 15.13 (0.8H, brs, OH) ppm | | |
| 92 | (E)-1,5-bis(4-Hydroxy-3-methoxyphenyl)-2,2-dimethylpent-4-ene-1,3-dione | | | |
| | Compound 47 | as Example 56 | 56% | |
| | Spectral data: | LCMS 371 [M + H]$^+$, 369 [M − H]$^−$, $^1$H NMR (400 MHz, CDCl$_3$) δ 1.55 (6H, s, O=CC(CH$_3$)$_2$), 3.88 (3H, s, OCH$_3$), 3.99 (3H, s, OCH$_3$), 6.51 (1H, d, J = 15.5 Hz, vinyl CH), 6.84-6.88 (2H, m, 2 × ArH), 6.92 (1H, d, J = 2.0 Hz, ArH), 7.04 (1H, dd, J = 8.0, 2.0 Hz, ArH), 7.41 (1H, dd, J = 8.0, 2.0 Hz, ArH), 7.51 (1H, d, J = 2.0 Hz, ArH), 7.68 (1H, d, J = 15.5 Hz, vinyl CH) ppm; $^{13}$C NMR (100 MHz, CDCl$_3$) δ 23.49, 55.95, 56.02, 59.86, 109.80, 111.36, 113.93, 114.70, 119.35, 123.99, 124.63, 126.64, 128.23, 144.54, 146.46, 146.68, 148.50, 150.25, 198.26, 199.13 ppm. | | |
| 93 | (E)-1-(4-Fluorophenyl)-5-(4-hydroxy-3-methoxy-phenyl)-2,2-dimethyl-pent-4-ene-1,3-dione | | | |
| | Compound 52 | as Example 56 | 87% | |
| | Spectral data: | LCMS 343 [M + H]$^+$, 341 [M − H]$^+$; $^1$H NMR (400 MHz, CDCl$_3$) δ 1.54 (6H, s, O=CC(CH$_3$)$_2$), 3.89 (3H, s, OCH$_3$), 6.00 (1H, br s, phenol OH), 6.52 (1H, d, J = 16.0 Hz, vinyl CH), 6.87 (1H, d, J = 8.0 Hz, ArH), 6.92 (1H, d, J 2.0 Hz, ArH), 7.03-7.07 (3H, m, 3 × ArH), 7.70 (1H, d, J = 16.0 Hz, vinyl CH), 7.87 (2H, br t, J = 5.5 Hz, 2 × ArH) ppm; $^{13}$C NMR (100 MHz, CDCl$_3$) δ 23.19, 25.60, 56.02, 60.12, 109.75, 114.74, 115.59, 115.81, 118.82, 124.15, 126.49, 131.84, 131.94, 145.14, 146.70, 148.66, 164.15, 166.69, 198.49, 198.51 ppm. | | |
| 99 | (E)-5-(4-Hydroxy-3-methoxyphenyl)-2,2-dimethyl-1-(naphthalene-3-yl)pent-4-ene-1,3-dione | | | |
| | Compound 58 | as Example 56 | 78% | |
| | Spectral data: | LCMS 375 [M + H]$^+$, 373 [M − H]$^+$; $^1$H NMR (400 MHz, CDCl$_3$) δ 1.63 (6H, s, O=CC(CH$_3$)$_2$), 3.86 (3H, s, OCH$_3$), 5.92 (1H, br s, phenol OH), 6.58 (1H, d, J = 15.5 Hz, vinyl CH), 6.84 (1H, d, J = 8.0 Hz, ArH), 6.90 (1H, d, J = 2.0 Hz, ArH), 7.03 (1H, dd, J = 8.0, 2.0 Hz, ArH), 7.49-7.59 (2H, m, 2 × ArH), 7.74 (1H, d, J = 15.5 Hz, vinyl CH), 7.81-7.85 (2H, m, 2 × ArH), 7.90-7.95 (2H, m, 2 × ArH), 8.36 (1H, br s, ArH) ppm; $^{13}$C NMR (100 MHz, CDCl$_3$) δ 23.42, 56.01, 60.36, 109.66, 114.66, 119.17, 124.19, 124.79, 126.61, 126.73, 127.58, 128.37, 128.63, 129.84, 130.99, 132.36, 133.01, 135.29, 144.87, 146.66, 148.54, 198.69, 200.08 ppm. | | |
| 100 | (E)-5-(4-Hydroxy-3-methoxyphenyl)-2,2-dimethyl-1-p-tolylpent-4-ene-1,3-dione | | | |
| | Compound 65 | as Example 56 | 87% | |
| | Spectral data: | $^1$H NMR (400 MHz, CDCl$_3$) δ 1.54 (6H, s, OCC(CH$_3$)$_2$CO), 2.36 (3H, s, PhCH$_3$), 3.89 (3H, s, OCH$_3$), 5.92 (1H, br s, phenol OH), 6.52 (1H, d, J = 15.5 Hz, vinyl CH), 6.87 (1H, d, J = 8.0 Hz, ArH), 6.92 (1H, d, J = 2.0 Hz, ArH), 7.04 (1H, dd, J = 8.0, 2.0 Hz, ArH), 7.18 (2H, d, J 8.0 = Hz, 2 × ArH), 7.70 (1H, d, J = 15.5 Hz, vinyl CH), 7.76 (2H, d, J = 8.0 Hz, 2 × ArH) ppm. | | |

TABLE 5-continued

Other examples of synthesised compounds with their characterisation data

| Compound | Starting material: | Procedure: | Yield: | m.p.: |
|---|---|---|---|---|
| 70 | 5-(4-Hydroxy-3-methoxyphenyl)-2,2-dimethyl-1-(1-methylcyclopropyl)pentane-1,3-dione | | | |
| | Compound 90 | as Example 31 except using 10% palladium on carbon and with purification using column chromatography | 75% | |
| | Spectral data: | LCMS 375 [M + H]$^+$, 373 [M − H]$^+$; $^1$H NMR (400 MHz, CDCl$_3$) δ 1.63 (6H, s, O=CC(CH$_3$)$_2$), 3.86 (3H, s, OCH$_3$), 5.92 (1H, br s, phenol OH), 6.58 (1H, d, J = 15.5 Hz, vinyl CH), 6.84 (1H, d, J = 8.0 Hz, ArH), 6.90 (1H, d, J = 2.0 Hz, ArH), 7.03 (1H, dd, J = 8.0, 2.0 Hz, ArH), 7.49-7.59 (2H, m, 2 × ArH), 7.74 (1H, d, J = 15.5 Hz, vinyl CH), 7.81-7.85 (2H, m, 2 × ArH), 7.90-7.95 (2H, m, 2 × ArH), 8.36 (1H, br s, ArH) ppm; $^{13}$C NMR (100 MHz, CDCl$_3$) δ 23.42, 56.01, 60.36, 109.66, 114.66, 119.17, 124.19, 124.79, 126.61, 126.73, 127.58, 128.37, 128.63, 129.84, 130.99, 132.36, 133.01, 135.29, 144.87, 146.66, 148.54, 198.69, 200.08 ppm. | | |
| 71 | 1-(4-Hydroxy-3-methoxyphenyl)-4,4,6,6-tetramethylheptane-3,5-dione | | | |
| | Compound 91 | as Example 31 except using 10% palladium on carbon and with purification using column chromatography | 76% | 98-99° C. |
| | Spectral data: | $^1$H NMR (400 MHz, CDCl$_3$) δ 1.15 (9H, s, C(CH$_3$)$_3$), 1.34 (6H, s, 2 × C(CH$_3$)), 2.70 (2H, t, J = 8.0 Hz, CH$_2$), 2.85 (2H, t, J = 8.0 Hz, CH$_2$), 3.88 (3H, s, OCH$_3$), 5.48 (1H, br s, phenol OH), 6.67-6.69 (2H, m, 2 × ArH), 6.83 (1H, d, J = 8.0 Hz, ArH) ppm; $^{13}$C NMR (100 MHz, CDCl$_3$) δ 23.04, 28.40, 29.53, 40.88, 45.68, 55.89, 62.36, 111.14, 114.32, 120.92, 132.72, 143.98, 146.38, 208.94, 214.27 ppm. | | |
| 72 | 1,5-bis(4-Hydroxy-3-methoxyphenyl)-2,2-dimethylpentane-1,-dione | | | |
| | Compound 92 | as Example 31 except using 10% palladium on carbon and with purification using column chromatography | 69% | |
| | Spectral data: | LCMS 371 [M]$^−$; $^1$H NMR (400 MHz, CDCl$_3$) δ 1.43 (6H, s, O=CC(CH$_3$)$_2$), 2.61-2.65 (2H, m, CH$_2$), 2.74-2.78 (2H, m, CH$_2$), 3.76 (3H, s, OCH$_3$), 3.86 (3H, s, OCH$_3$), 6.47 (1H, s, ArH), 6.51 (1H, dd, J = 8.0, 2.0 Hz, ArH), 6.74 (1H, d, J = 8.0 Hz, ArH), 6.80 (1H, d, J = 8.0 Hz, ArH), 7.20 (1H, dd, J = 8.0, 2.0 Hz, ArH), 7.38 (1H, d, J = 2.0 Hz, ArH) ppm; $^{13}$C NMR (100 MHz, CDCl$_3$) δ 23.34, 29.60, 41.01, 55.66, 55.86, 60.73, 110.77, 111.13, 113.89, 114.12, 120.91, 124.10, 127.85, 132.39, 143.81, 146.22, 146.52, 150.26, 197.43, 210.15 ppm. | | |
| 21 | 1-(4-Chlorophenyl)-5-(4-hydroxy-3-methoxyphenyl)pentane-1,3-dione | | | |
| | Compound 53 | as Example 57 | 92% | 57-63° C. |
| | Spectral data: | LRMS 331/333 [M − H]$^+$ $^1$H NMR (300 MHz, CDCl$_3$) δ 2.70 (2H, t, J = 7.8 Hz, CH$_2$CH$_2$), 2.93 (2H, t, J = 7.5 Hz, CH$_2$CH$_2$), 3.83 (3H, s, OCH$_3$), 5.69 (1H, brs, OH), 6.08 (1H, s, enol CH), 6.87-6.71 (2H, m, ArH), 6.83 (1H, d, J = 8.4 Hz, ArH), 7.38 (2H, d, J = 8.7 Hz, ArH), 7.76 (2H, d, J = 8.4 Hz, ArH), 16.12 (1H, brs, OH) ppm; $^{13}$C NMR (75 MHz, CDCl$_3$) δ 31.22, 41.11, 55.73, 96.24, 110.97, 114.35, 120.72, 128.23, 128.78, 132.39, 133.18, 138.41, 143.99, 146.41, 181.95, 195.84 ppm. | | |
| 22 | 1-(3-Chlorophenyl)-5-(4-hydroxy-3-methoxyphenyl)pentane-1,3-dione | | | |
| | Compound 54 | as Example 57 | 27% | 54-55° C. |
| | Spectral data: | LRMS 331/333 [M − H]$^+$; $^1$H NMR (300 MHz, CDCl$_3$) δ 2.72 (2H, t, J = 8.4 Hz, CH$_2$CH$_2$), 2.94 (2H, t, J = 8.1 Hz, CH$_2$CH$_2$), 3.86 (3H, s, OCH$_3$), 5.49 (1H, brs, OH), 6.09 (1H, s, CH), 6.70-6.72 (2H, m, ArH), 6.83 (1H, d, J = 8.7 Hz, ArH), 7.37 (1H, t, J = 7.8 Hz, ArH), 7.48 (1H, d, J = 6.9 Hz, ArH), 7.82 (1H, s, ArH), 16.01 (1H, s, OH) ppm; $^{13}$C NMR (75 MHz, CDCl$_3$) δ 31.35, 41.35, 55.90, 96.69, 111.01, 114.41, 120.88, 125.04, 127.12, 129.89, 132.15, 132.47, 134.89, 136.74, 144.11, 146.47, 181.64, 196.23 ppm. | | |

TABLE 5-continued

Other examples of synthesised compounds with their characterisation data

| Compound | Starting material: | Procedure: | Yield: | m.p.: |
|---|---|---|---|---|
| 23 | 1-(3,4-Dihlorophenyl)-5-(4-hydroxy-3-methoxyphenyl)pentane-1,3-dione | | | |
| | Compound 55 | as Example 57 | 50% | 78-80° C. |
| | Spectral data: LRMS 365 [M − H]$^+$, 362, 367; $^1$H NMR (300 MHz, CDCl$_3$) δ 2.69 (2H, t, J = 8.1 Hz, CH$_2$CH$_2$), 2.91 (2H, t, J = 7.5 Hz, CH$_2$CH$_2$), 3.82 (3H, s, OCH$_3$), 5.26 (0.5H, s, OH), 5.99 (1H, s, CH), 6.67-6.69 (2H, m, ArH), 6.82 (1H, d, J = 7.5 Hz, ArH), 7.25-7.31 (1H, m, ArH), 7.40 (1H, m, ArH), 7.45-7.55 (1H, m, ArH) ppm; $^{13}$C NMR (75 MHz, CDCl$_3$) δ 31.30, 40.95, 55.89, 101.56, 110.98, 114.39, 120.87, 127.32, 130.52, 130.96, 132.28, 132.65, 133.90, 137.12, 144.11, 146.45, 183.08, 195.05 ppm. | | | |
| 24 | 1-(2,4-Dihlorophenyl)-5-(4-hydroxy-3-methoxyphenyl)pentane-1,3-dione | | | |
| | Compound 56 | as Example 57 | 38% | 86-87° C. |
| | Spectral data: LRMS 365 [M − H]$^+$, 367; $^1$H NMR (300 MHz, CDCl$_3$) δ 2.72 (2H, t, J = 8.1 Hz, CH$_2$CH$_2$), 2.94 (2H, t, J = 7.5 Hz, CH$_2$CH$_2$), 3.87 (3H, s, OCH$_3$), 5.49 (1H, brs, OH), 6.07 (1H, s, CH), 6.70-6.75 (2H, m, ArH), 6.81-6.89 (1H, m, ArH), 7.52 (1H, d, J = 8.4 Hz, ArH), 7.66 (1H, dd, J = 8.7, 2.4 Hz, ArH), 7.93 (1H, d, J = 2.1 Hz, ArH), 15.91 (1H, brs, OH) ppm; $^{13}$C NMR (75 MHz, CDCl$_3$) δ 31.33, 41.28, 55.89, 96.58, 110.99, 114.41, 120.87, 126.00, 128.94, 130.70, 132.37, 133.25, 134.84, 136.59, 144.13, 146.47, 180.80, 196.16 ppm | | | |
| 28 | 6-(4-Hydroxy-3-methoxyphenyl)-1-phenyl-hexane-2,4-dione | | | |
| | Compound 60 | as Example 57 | 55% | |
| | Spectral data: LRMS 311 [M − H]$^+$; $^1$H NMR (300 MHz, DMSO) δ 2.10-2.38 (0.9H, m), 2.57 (2H, t, J = 7.8 Hz, CH$_2$CH$_2$), 2.61-2.77 (4.8H, m), 3.61 (1.9H, s), 3.71 (3H, s), 3.73 (3.3H, s), 3.79 (1.5H, s), 5.71 (1H, s), 6.53-6.60 (1.6H, m, ArH), 6.62-6.69 (1.8H, m, ArH), 6.72-6.77 (1.7H, m, ArH), 7.14 (1.6H, m, ArH), 7.20-7.86 (6.8H, m, ArH), 8.64 (0.8H, s), 8.66 (1H, s), 15.40, (1H, brs) ppm; $^{13}$C NMR (75 MHz, DMSO) δ 28.86, 30.86, 44.51, 45.16, 50.00, 56.00, 56.04, 56.36, 100.19, 112.96, 115.76, 120.72, 120.79, 127.15, 127.33, 128.77, 128.94, 129.72, 130.24, 131.73, 132.04, 134.62, 135.92, 145.13, 145.22, 147.88, 192.32, 194.34, 203.23, 204.97 ppm. Analysis by $^1$H NMR shows a mixture of the enol and keto tautomers in an unknown ratio. Due to the complexity of the $^1$NMR only partial assignment has been made. | | | |
| 29 | 6-(4-Hydroxy-3-methoxyphenyl)-1-naphthalen-1-yl-hexane-2,4-dione | | | |
| | Compound 61 | as Example 57 | 19% | |
| | Spectral data: LRMS 361 [M − H]$^+$; $^1$H NMR (300 MHz, DMSO) δ 2.1-2.29 (3.8H, m), 2.45-2.58 (m, DMSO + CH$_2$CH$_2$), 2.60-2.70 (5.7H, m), 3.68 (3.3H, s), 3.72, (2.8H, s), 3.85 (1.9H, s), 4.14 (2H, s), 4.30 (1.8H, s), 5.74 (1H, s), 6.50-6.59 (1H, m, ArH), 6.64 (1H, t, J = 8.1 Hz, ArH), 6.74 (1H, s, ArH), 6.80-7.15 (1H, m), 7.34 (0.8H, d, J = 4.5 Hz, ArH), 7.43-7.55 (6.3H, m, ArH), 7.81-7.97 (5.9H, m, ArH), 8.71 (1H, s), 8.72 (1H, s), 15.50 (0.9H, s) ppm; $^{13}$C NMR (75 MHz, DMSO) δ 28.88, 30.92, 42.48, 45.21, 47.94, 55.99, 56.04, 56.24, 100.09, 112.92, 112.97, 115.73, 115.79, 120.71, 120.77, 124.48, 124.76, 125.98, 126.07, 126.16, 126.26, 126.58, 126.74, 127.98, 128.65, 128.87, 128.97, 131.58, 131.67, 132.03, 132.21, 132.52, 133.81, 133.87, 145.14, 145.21, 147.86, 147.89, 192.64, 194.12, 203.20, 205.18 ppm. Analysis by $^1$H NMR shows a mixture of the enol and keto tautomers in an unknown ratio. Due to the complexity of the $^1$NMR only partial assignment has been made. | | | |
| 30 | 6-(4-Hydroxy-3-methoxyphenyl)-1,1-diphenyl-hexane-2,4-dione | | | |
| | Compound 62 | as example 57 | 30% | |
| | Spectral data: LRMS 387 [M − H]$^+$; $^1$H NMR (300 MHz, DMSO) δ 2.10-2.28 (1H, m), 2.53-2.78 (5H, m), 3.69 (2.6H, s), 3.72 (1.3H, s), 3.74 (0.8H, s), 5.17 (0.9H, s), 5.39 (0.6H, s), 5.70 (0.9H, s), 6.50-6.59 (1.2H, m, ArH), 6.64 (1.2H, d, J = 7.8 Hz, ArH), 6.73 (1.2H, dd, J = 12.0, 1.8 Hz, ArH), 7.20-7.39 (12.8H, ArH), 8.64 (0.5H, s), 8.67 (1H, s), 15.45 (1H, brs) ppm; $^{13}$C NMR (75 MHz, DMSO) δ 28.85, 31.05, 45.15, 55.98, 56.02, 56.37, 59.33, 63.87, 101.21, 112.93, 115.73, 120.70, 120.83, 127.41, 127.55, 128.95, 129.03, 129.27, 129.52, 131.58, 131.97, 138.55, 139.88, 145.13, 145.25, 147.87, 192.79, 194.80, 203.20, 204.58 ppm. Analysis by $^1$H NMR shows a mixture of the enol and keto tautomers in an unknown ratio. Due to the complexity of the $^1$H NMR spectrum only partial assignment has been made. | | | |

TABLE 5-continued

Other examples of synthesised compounds with their characterisation data

| Compound | Starting material: | Procedure: | Yield: | m.p.: |
|---|---|---|---|---|

31  6-(4-Hydroxy-3-methoxyphenyl)-1,1-dimethyl-1-phenyl-hexane-2,4-dione
Compound 63　　　　　　　　as Example 57　　　6%
Spectral data: LRMS 339 [M − H]$^+$; $^1$H NMR (300 MHz, CDCl$_3$) δ 1.49 (6H, s, 2 × CCH$_3$), 2.45 (2H, t, J = 8.1 Hz, CH$_2$CH$_2$), 2.79 (2H, t, J = 8.1 Hz, CH$_2$CH$_2$), 3.82 (3H, s, OCH$_3$), 5.25 (1H, s, CH), 5.51 (1H, brs, OH), 6.54-6.64 (2H, m, ArH), 6.78 (1H, d, J = 8.1 Hz, ArH), 7.14-7.35 (5H, m, ArH), 15.40 (1H, s, OH) ppm; $^{13}$C NMR (75 MHz, CDCl$_3$) δ 24.57, 26.26, 26.12, 31.61, 39.61, 44.97, 52.46, 53.09, 55.85, 55.89, 97.75, 110.90, 114.28, 120.78, 120.87, 126.23, 126.62, 127.33, 128.40, 128.99, 132.46, 132.66, 142.64, 143.93, 145.30, 146.37, 189.56, 201.96, 203.36, 205.91 ppm. Analysis by $^1$H NMR shows a mixture of tautomers in an approximate 3.5:1 ratio. The major tautomer is quoted in $^1$H NMR data.

74  1-(2-Chlorophenyl)-5-(4-hydroxy-3-methoxyphenyl)pentane-1,3-dione
Compound 94　　　　　　　　as Example 57　　　71%　　　89° C.
Spectral data: LCMS 333 [M + H]$^+$, 331 [M]$^-$; $^1$H NMR (400 MHz, CDCl$_3$) δ 2.70-2.73 (2H, m, CH$_2$), 2.93-2.97 (2H, m, CH$_2$), 3.87 (3H, s, OCH$_3$), 5.61 (1H, br s, enol CH or phenol OH), 6.02 (1H, s, enol CH or phenol OH), 6.72-6.73 (2H, m, 2 × ArH), 6.86 (1H, d, J = 8.4 Hz, ArH), 7.31-7.40 (2H, m, 2 × ArH), 7.43 (1H, dd, J = 8.4, 1.6 Hz, ArH), 7.56 (1H, dd, J = 8.0 and 1.6 Hz, ArH), 15.73 (1H, brs, enol OH) ppm; $^{13}$C NMR (100 MHz, CDCl$_3$) δ 31.28, 40.92, 55.81, 101.60, 110.91, 114.31, 120.78, 126.85, 129.93, 130.60, 131.54, 131.63, 132.32, 135.38, 143.98, 146.38, 184.30, 194.86 ppm.

75  1-(4-chloro-3-methylphenyl)-5-(4-hydroxy-3-methoxyphenyl)pentane-1,3-dione
Compound 95　　　　　　　　as Example 57　　　61%　　　68-70° C.
Spectral data: LCMS [M$^+$] 347; $^1$H NMR (400 MHz CDCl$_3$) δ 2.40 (3H, s, CH$_3$), 2.70 (2H, t, CH$_2$), 2.91 (2H, t, CH$_2$), 3.84 (3H, s, OCH$_3$), 5.49 (1H, s, enol CH or phenol OH) 6.06 (1H, s, enol CH or phenol OH), 6.69 (1H, s, ArH), 6.70 (1H, d, ArH), 6.81 (1H, d, ArH), 7.37 (1H, d, ArH), 7.60 (1H, d, ArH), 7.70 (1H, s, ArH) ppm; $^{13}$C NMR (400 MHz CDCl$_3$) δ 20.3, 31.5, 41.4, 56.0, 96.5, 111.1, 114.4, 120.9, 125.8, 129.4, 129.5, 132.6, 133.4, 136.7, 138.9, 144.1, 146.5, 182.6, 195.8 ppm.

76  1-(4-Chloro-2-methylphenyl)-5-(4-hydroxy-3-methoxyphenyl)pentane-1,3-dione
Compound 96　　　　　　　　as Example 57　　　85%　　　78° C.
Spectral data: LCMS 345 [M − H]$^+$; $^1$H NMR (400 MHz, CDCl$_3$) δ 2.46 (3H, s, PhCH$_3$), 2.68-2.72 (2H, m, CH$_2$), 2.93-2.96 (2H, m, CH$_2$), 3.87 (3H, s, OCH$_3$), 5.60 (1H, br s, enol CH or phenol OH), 5.78 (1H, s, enol CH or phenol OH), 6.71-6.73 (2H, m, 2 × ArH), 6.86 (1H, d, J = 8.0 Hz, ArH), 7.19-7.27 (2H, m, 2 × ArH), 7.36 (1H, d, J = 8.0 Hz, ArH), 15.94 (1H, brs, enol OH) ppm; $^{13}$C NMR (100 MHz, CDCl$_3$) δ 20.50, 31.33, 40.97, 55.80, 100.45, 110.90, 114.32, 120.78, 125.90, 129.59, 131.26, 132.38, 134.25, 136.46, 139.08, 143.98, 146.38, 186.85, 194.98 ppm.

77  1-(3-chloro-2-methylphenyl)-5-(4-hydroxy-3-methoxyphenyl)pentane-1,3-dione
Compound 97　　　　　　　　as Example 57　　　90%
Spectral data: LCMS 347 [M + H]$^+$, 345 [M − H]$^+$; $^1$H NMR (400 MHz, CDCl$_3$) δ 2.45 (3H, s, PhCH$_3$), 2.67-2.71 (2H, m, CH$_2$), 2.92-2.96 (2H, m, CH$_2$), 3.87 (3H, s, OCH$_3$), 5.57 (1H, br s, enol CH or phenol OH), 5.73 (1H, s, enol CH or phenol OH), 6.71-6.72 (2H, m, 2 × ArH), 6.85 (1H, d, J = 8.0 Hz, ArH), 7.16 (1H, t, J = 8.0 Hz, ArH), 7.26 (1H, d, J = 8.0 Hz, ArH), 7.44 (1H, d, J = 8.0 Hz, ArH), 15.78 (1H, br s, enol OH) ppm; $^{13}$C NMR (100 MHz, CDCl$_3$) δ 17.28, 31.33, 40.95, 55.83, 101.21, 110.92, 114.35, 120.81, 126.46, 126.63, 131.16, 132.34, 134.44, 135.91, 138.49, 144.03, 146.42, 187.49, 195.08 ppm.

78  1-(3-chloro-4-methylphenyl)-5-(4-hydroxy-3-methoxyphenyl)pentane-1,3-dione
Compound 98　　　　　　　　as Example 57　　　83%　　　70-72° C.
Spectral data: LCMS [M$^+$] 347; $^1$H NMR (400 MHz CDCl$_3$) δ 2.41 (3H, s, CH$_3$), 2.70 (2H, t, CH$_2$), 2.91 (2H, t, CH$_2$), 3.84 (3H, s, OCH$_3$), 5.48 (1H, s, enol CH or phenol OH) 6.06 (1H, s, enol CH or phenol OH), 6.70 (1H, d, ArH), 6.71 (1H, s, ArH), 6.83 (1H, d, ArH), 7.28 (1H, d, ArH), 7.60 (1H, d, ArH), 7.81 (1H, s, ArH) ppm; $^{13}$C NMR (400 MHz CDCl$_3$) δ 20.4, 31.5, 41.3, 56.0, 96.4, 111.1, 114.5, 120.9, 125.2, 127.7, 131.2, 132.6, 134.2, 135.0, 140.9, 144.1, 146.6, 182.2, 195.7 ppm.

TABLE 5-continued

Other examples of synthesised compounds with their characterisation data

| Compound | Starting material: | Procedure: | Yield: | m.p.: |
|---|---|---|---|---|
| 86 | 5-(2-Chloro-4-hydroxy-5-methoxyphenyl)-1-(naphthalene-3-yl)pentane-1,3-dione | | | |
| | Compound 105 | as Example 57 | 26% | 134° C. |
| | Spectral data: | LCMS 383 [M + H]$^+$; $^1$H NMR (400 MHz, CDCl$_3$) δ 2.76-2.80 (2H, m, CH$_2$), 3.06-3.10 (2H, m, CH$_2$), 3.85 (3H, s, OCH$_3$), 5.57 (1H, br s, phenol OH or enol CH), 6.29 (1H, s, phenol OH or enol CH), 6.77 (1H, s, ArH), 6.96 (1H, s, ArH), 7.53-7.61 (2H, m, 2 × ArH), 7.87-7.89 (3H, m, 3 × ArH), 7.95 (1H, d, J = 8.0 Hz, ArH), 8.42 (1H, s, ArH), 16.24 (1H, brs, enol OH) ppm. $^{13}$C NMR (100 MHz, CDCl$_3$) δ 29.48, 39.47, 56.13, 96.82, 112.51, 115.50, 123.04, 125.19, 126.77, 127.73, 128.09, 128.18, 128.41, 129.29, 129.41, 131.93, 132.68, 135.22, 144.72, 145.36, 182.88, 195.77 ppm. | | |
| 79 | 5-(4-Hydroxy-3-methoxyphenyl)-2,2-dimethyl-1-(naphthalene-2-yl)pentane-1,3-dione | | | |
| | Compound 99 | as Example 31 except using 10% palladium on carbon and with purification using column chromatography | 90% | |
| | Spectral data: | LCMS 377 [M + H]$^+$; $^1$H NMR (400 MHz, CDCl$_3$) δ 1.52 (6H, s, 2 × C (CH$_3$)), 2.68-2.72 (2H, m, CH$_2$), 2.76-2.80 (2H, m, CH$_2$), 3.62 (3H, s, OCH$_3$), 6.39 (1H, d, J = 2.0 Hz, ArH), 6.52 (1H, dd, J 8.0, 2.0 Hz, ArH), 6.67 (1H, d, J = 8.0 Hz, ArH), 7.52-7.61 (2H, m, 2 × ArH), 7.80-7.86 (4H, m, 4 × ArH), 8.17 (1H, s, ArH) ppm; $^{13}$C NMR (100 MHz, CDCl$_3$) δ 23.30, 29.57, 41.16, 55.53, 61.14, 110.68, 114.08, 120.97, 124.45, 126.82, 127.54, 128.43, 128.73, 129.73, 130.66, 132.22, 132.27, 132.54, 135.19, 143.75, 146.13, 199.23, 209.79 ppm. | | |
| 80 | 5-(4-Hydroxy-3-methoxyphenyl)-1-p-tolylpentane-1,3-dione | | | |
| | Compound 65 | as Example 31 except using 10% palladium on carbon and with purification using column chromatography | 94% | |
| | Spectral data: | LCMS 313 [M + H]$^+$; $^1$H NMR (400 MHz, CDCl$_3$) δ 2.42 (3H, s, PhCH$_3$), 2.70-2.74 (2H, m, CH$_2$), 2.94-2.98 (2H, m, CH$_2$), 3.86 (3H, s, OCH$_3$), 5.62 (1H, brs, enol CH or phenol OH), 6.14 (1H, s, enol CH or phenol OH), 6.73-6.75 (2H, m, 2 × ArH), 6.86 (1H, d, J = 8.0 Hz, ArH), 7.26 (2H, d, J = 8.0 Hz, 2 × ArH), 7.78 (2H, d, J = 8.0 Hz, 2 × ArH), 16.26 (1H, brs, enol OH) ppm; $^{13}$C NMR (100 MHz, CDCl$_3$) δ 21.53, 31.41, 41.14, 55.77, 95.98, 110.94, 114.29, 120.76, 126.99 (2 × CH), 129.28 (2 × CH), 132.03, 132.60, 143.06, 143.92, 146.37, 183.60, 195.12 ppm. | | |
| 81 | 5-(4-Hydroxy-3-methoxyphenyl)-2,2-dimethyl-1-p-tolylpentane-1,3-dione | | | |
| | Compound 100 | as Example 31 except using 10% palladium on carbon and with purification using column chromatography | 82% | |
| | Spectral data: | LCMS 341 [M + H]$^+$; $^1$H NMR (400 MHz, CDCl$_3$) δ 1.43 (6H, s, OCC (CH$_3$)$_2$CO), 2.38 (3H, s, PhCH$_3$), 2.64 (2H, t, J = 7.2 Hz, CH$_2$), 2.77 (2H, t, J = 7.2 Hz, CH$_2$), 3.77 (3H, s, OCH$_3$), 5.43 (1H, brs, phenol OH), 6.48 (1H, d, J = 2.0 Hz, ArH), 6.54 (1H, dd, J 8.0, 2.0 Hz, ArH), 6.74 (1H, d, J = 8.0 Hz, ArH), 7.13 (2H, d, J = 8.0 Hz, 2 × ArH), 7.59 (2H, d, J = 8.0 Hz, 2 × ArH) ppm; $^{13}$C NMR (100 MHz, CDCl$_3$) δ 21.54, 23.16, 29.58, 41.11, 55.71, 60.90, 110.83, 114.07, 129.04, 129.25, 132.42, 132.65, 143.85, 143.88, 146.20, 198.83, 209.84 ppm. | | |

TABLE 5-continued

Other examples of synthesised compounds with their characterisation data

| Compound | Starting material: | Procedure: | Yield: | m.p.: |
|---|---|---|---|---|
| 82 | 1-(4-Cyanophenyl)-5-(4-hydroxy-3-methoxyphenyl)pentane-1,3-dione | | | |
| | Compound 101 | as Example 31 except using 10% palladium on carbon and with purification using column chromatography | 29% | 128-130° C. |
| | Spectral data: | LCMS 322 [M]$^-$; $^1$H NMR (400 MHz, CDCl$_3$) δ 2.77 (2H, m, CH$_2$), 2.96 (2H, m, CH$_2$), 3.88 (3H, s, OCH$_3$), 5.50 (1H, br s, enol CH or phenol OH), 6.14 (1H, s, enol CH or phenol OH), 6.71-6.73 (2H, m, 2 × ArH), 6.85 (1H, d, J = 8.4 Hz, ArH), 7.75 (2H, d, J = 8.4 Hz, 2 × ArH), 7.94 (2H, d, J = 8.4 Hz, 2 × ArH), 15.91 (1H, brs, enol OH) ppm; $^{13}$C NMR (100 MHz, CDCl$_3$) δ 31.12, 41.79, 55.86, 97.43, 110.92, 114.37, 115.37, 118.09, 120.82, 1257.36 (2 × CH), 132.29 (2 × CH), 132.40, 138.64, 144.07, 146.42, 179.43, 197.98 ppm. | | |
| 83 | 1-(4-tert-Butylphenyl)-5-(4-hydroxy-3-methoxyphenyl)pentane-1,3-dione | | | |
| | Compound 102 | as Example 31 except using 10% palladium on carbon and with purification using column chromatography | 91% | 87-88° C. |
| | Spectral data: | LCMS 355 [M + H]$^+$; $^1$H NMR (400 MHz, CDCl$_3$) δ 1.35 (9H, s, C (CH$_3$)$_3$), 2.72 (2H, t, J = 8.4 Hz, CH$_2$), 2.96 (2H, t, J = 8.4 Hz, CH$_2$), 3.87 (3H, s, OCH$_3$), 5.54 (1H, br s, enol CH or phenol OH), 6.13 (1H, s, enol CH or phenol OH), 6.72-6.74 (2H, m, 2 × ArH), 6.86 (1H, d, J = 8.0 Hz, ArH), 7.47 (2H, d, J = 8.0 Hz, 2 × ArH), 7.81 (2H, d, J = 8.0 Hz, 2 × ArH), 16.24 (1H, brs, enol OH) ppm; $^{13}$C NMR (100 MHz, CDCl$_3$) δ 31.07, 31.45, 35.03, 41.24, 55.83, 96.12, 110.95, 114.29, 120.80, 125.58 (2 × CH), 126.87 (2 × CH), 132.01, 132.66, 143.93, 146.37, 156.10, 183.44, 195.34 ppm. | | |
| 84 | 5-(4-Hydroxy-3-methoxyphenyl)-1-o-tolylpentane-1,3-dione | | | |
| | Compound 103 | as Example 31 except using 10% palladium on carbon and with purification using column chromatography | 88% | 96° C. |
| | Spectral data: | LCMS 313 [M + H]$^+$, 625 [2M + H]$^+$; $^1$H NMR (400 MHz, CDCl$_3$) δ 2.48 (3H, s, PhCH$_3$), 2.68-2.72 (2H, m, CH$_2$), 2.93-2.97 (2H, m, CH$_2$), 3.87 (3H, s, OCH$_3$), 5.56 (1H, br s, enol CH or phenol OH), 5.81 (1H, s, enol CH or phenol OH), 6.72-6.74 (2H, m, 2 × ArH), 6.86 (1H, d, J = 8.0 Hz, ArH), 7.21-7.27 (2H, m, 2 × ArH), 7.33-7.37 (2H, m, 2 × ArH), 7.43 (1H, d, J = 8.0 Hz, ArH), 15.97 (1H, brs, enol OH) ppm; $^{13}$C NMR (100 MHz, CDCl$_3$) δ 20.58, 31.39, 41.08, 55.82, 100.57, 110.93, 114.32, 120.81, 125.71, 128.23, 130.64, 131.36, 132.52, 135.84, 136.96, 143.97, 146.39, 187.91, 195.05 ppm. | | |
| 85 | 5-(4-Hydroxy-3-methoxyphenyl)-1-m-tolylpentane-1,3-dione | | | |
| | Compound 104 | as Example 31 except using 10% palladium on carbon and with purification using column chromatography | 88% | 52° C. |
| | Spectral data: | LCMS 313 [M + H]$^+$, 625 [2M + H]$^+$; $^1$H NMR (400 MHz, CDCl$_3$) δ 2.42 (3H, s, PhCH$_3$), 2.71-2.75 (2H, m, CH$_2$), 2.94-2.98 (2H, m, CH$_2$), 3.87 (3H, s, OCH$_3$), 5.54 (1H, brs, enol CH or phenol OH), 6.14 (1H, s, enol CH or phenol OH), 6.72-6.75 (2H, m, 2 × ArH), 6.86 (1H, d, J = 8.0 Hz, ArH), 7.34-7.35 (2H, m, 2 × ArH), 7.65-7.68 (2H, m, 2 × ArH), 16.19 (1H, brs, enol OH) ppm; $^{13}$C NMR (100 MHz, CDCl$_3$) δ 21.36, 31.42, 41.31, 55.83, 96.45, 110.96, 114.32, 120.81, 124.14, 128.48 132.62, 133.11, 134.76, 138.37, 143.96, 146.39, 183.51, 195.71 ppm. | | |

TABLE 5-continued

Other examples of synthesised compounds with their characterisation data

| Compound | Starting material: | Procedure: | Yield: | m.p.: |
|---|---|---|---|---|
| 89 | 5-(3-Ethoxy-4-hydroxyphenyl)-1-phenylpentane-1,3-dione Compound 106 | as Example 31 except using 10% palladium on carbon and with purification using column chromatography | 77% | 110-112° C. |
| | Spectral data: | LCMS 313 $[M + H]^+$, 335 $[M + Na]^+$; $^1H$ NMR (400 MHz, $CDCl_3$) δ 1.43 (3H, t, J = 7.0 Hz, $OCH_2CH_3$), 2.72 (2H, m, $CH_2$), 2.94 (2H, m, $CH_2$), 4.09 (2H, q, J = 7.0 Hz, $OCH_2CH_3$), 5.57 (1H, brs, enol CH or phenol OH), 6.15 (1H, s, enol CH or phenol OH), 6.71-6.73 (2H, m, 2 × ArH), 6.86 (1H, d, J = 8.0 Hz, ArH), 7.43-7.56 (3H, m, 3 × ArH), 7.85-7.88 (2H, m, 2 × ArH), 16.18 (1H, brs, enol OH) ppm; $^{13}C$ NMR (100 MHz, $CDCl_3$) δ 14.87, 31.40, 41.37, 64.39, 96.43, 111.88, 114.25, 120.73, 126.97 (2 × CH), 128.60 (2 × CH), 132.30, 132.51, 134.81, 144.10, 145.65, 183.23, 195.87 ppm. | | |

Example 61

TRPV1 Receptor Modulation in the Rat Vas Deferens (Assay 1)

Wistar derived male rats (275±25 g) were suppressed by $CO_2$ overexposure. The vas deferens was removed, placed in Krebs solution, pH 7.4 (composition in g/l: NaCl 6.89, KCl 0.35, $CaCl_2$ 0.277, $KH_2PO_4$ 0.163, $MgSO_4.7H_2O$ 0.296, $NaHCO_3$ 2.1 glucose 1.8) and excess fat and connective tissue removed. The portion of the vas deferens closest to the prostate was cut in half and each half was placed under 1 g tension in a 10 ml bath containing Krebs solution at 32° C. The tissue was contracted by electrical field stimulation (EFS; 60% of maximum stimulation, 0.015 Hz, 0.5 ms in duration) and contractile responses were measured.

TABLE 6

TRPV1 receptor modulation in the rat vas deferens

| Compound | Saturated (S) or unsaturated (U) | Inhibition of EFS response relative to capsaicin [%] |
|---|---|---|
| 33 | U | −12 |
| 1 | S | 27 |
| 34 | U | −15 |
| 2 | S | 96 |
| 35 | U | 25 |
| 3 | S | 63 |
| 68 | U | 14 |
| 69 | S | 38 |
| 38 | U | −36 |
| 6 | S | 24 |
| 40 | U | −82 |
| 8 | S | 36 |
| 42 | U | 6 |
| 10 | S | 16 |
| 43 | U | −13 |
| 11 | S | 68 |

It is seen that saturation of the bond between the 4-hydroxy-3-methoxyphenyl group and the carbonyl generally results in an increase in TRPV1 activity in the assay.

Example 62

TRPV1 Modulation in DRG Neurones (Assay 2)

It is well known that a subset of neurones from dorsal root ganglia (DRG) are characterized by their unique sensitivity to the neurotoxin capsaicin (Szallasi, A. et al., Pharmacol Rev, 159-212, 51(2), (1999)), which excites them by activating TRPV1 receptor (Caterina, M. J. et al., Nature, 816-824, 389(6653), (1997)). Capsaicin releases the peptide neurotransmitters calcitonin gene-related peptide (CGRP) and substance P (SP) from central and peripheral endings of these neurones.

Rat DRG sensory neurones were cultured by modification of a previously described method (Hall, A. K. et al., J. Neurosci., 2775-2784, 17(8), (1997)). The culture used for this experiment contained sensory neurones, Schwann cells and fibroblasts. The effects of test compounds on CGRP release in the absence and presence of capsaicin were examined. The compounds 1, 2, 4, 6, 7, 11, 12, 13, 14, 15, 16, 17, 18, 19, 20, 21, 22, 23, 24, 25, 26, 27, 28, 29, 30, 31, 32, 69, 71, 74, 76, 80, 81, 82, 83, 84 and 3-gingerdione were tested.

The mature neurones were exposed to: (a) Vehicle (DMSO, 0.1%), (b) Test compounds (3 and 30 μM), (c) Capsaicin (1 μM), (d) Test compounds (3 and 30 μM) and capsaicin (1 μM).

Following a 20 min incubation, the amount of CGRP in the supernatant was measured by an enzyme-linked immunosorbant assay (ELISA, SpiBio kit A05482) specific for rat CGRP.

The results are shown in Table 7 below.

TABLE 7

Effect of test compounds on CGRP release in rat DRG sensory neurones

| Compound | CGRP release (% of capsaicin (1 μM) response) | | Effect of test compounds on capsaicin (1 μM)-induced CGRP release (%) −ve: inhibition of capsaicin response +ve: potentiation of capsaicin response | |
|---|---|---|---|---|
| | 3 μM | 30 μM | 3 μM | 30 μM |
| 2 | 20 | 117 | 46 | 8 |
| 4 | 36 | 63 | 58 | 24 |
| 15 | 34 | 34 | −18 | −27 |
| 16 | 53 | 52 | 49 | 49 |
| 69 | 49 | 36 | 49 | −23 |
| 11 | 24 | 111 | −8 | −12 |
| 6 | 52 | 49 | −15 | −28 |
| 7 | 35 | 76 | −19 | −41 |
| 12 | 19 | 73 | −13 | −14 |
| 32 | 22 | 21 | −47 | −40 |
| 3-Gingerdione | 17 | 18 | −37 | −43 |
| 1 | 26 | 41 | −36 | −24 |
| 14 | 120 | 94 | 12 | −35 |
| 17 | 55 | 183 | 98 | 22 |
| 13 | 75 | 245 | −48 | 67 |
| 18 | 146 | 146 | −10 | 12 |
| 19 | 139 | 286 | 29 | 159 |
| 20 | 46 | 96 | −29 | −4 |
| 21 | 50 | 150 | −6 | 56 |
| 22 | 60 | 163 | −2 | 58 |
| 23 | 84 | 242 | −2 | 47 |
| 24 | 92 | 193 | −13 | 2 |
| 25 | 48 | 59 | −18 | −21 |
| 26 | 66 | 248 | −47 | 31 |
| 27 | 85 | 162 | −46 | 66 |
| 28 | 29 | 107 | −51 | 29 |
| 29 | 65 | 164 | −46 | 41 |
| 30 | 70 | 122 | −49 | 150 |
| 31 | 56 | 109 | −17 | 77 |
| 71 | 48 | 38 | −26 | −29 |
| 74 | 54 | 75 | −15 | −6 |
| 76 | 55 | 107 | −9 | −4 |
| 80 | 68 | 118 | −44 | 24 |
| 81 | 45 | 104 | −25 | 22 |
| 82 | 53 | 58 | −4 | −27 |
| 83 | 66 | 144 | −11 | 0 |
| 84 | 54 | 74 | −32 | −26 |

All the compounds modulated CGRP release, either by increasing CGRP release or inhibiting capsaicin-induced CGRP release.

Example 63

Modulation of Smooth Muscle Tone in the Guinea Pig Ileum (Assay 3)

Duncan Hartley derived male guinea pigs (325±25 g) were suppressed by $CO_2$ overexposure, the abdominal cavity was exposed and ileal segments were removed. Small strips of ileum were suspended in organ baths containing Krebs solution (composition in g/l: NaCl 6.89, KCl 0.35, $CaCl_2$ 0.277, $KH_2PO_4$ 0.163, $MgSO_4.7H_2O$ 0.296, $NaHCO_3$ 2.1 glucose 1.8). The solution was kept at 32° C. and gassed with $O_2$ (95%)-$CO_2$ (5%) to maintain pH at 7.4. Mechanical activity was recorded by means of isotonic transducers. A resting tension of 1 g was applied to muscle strips before being equilibrated for 1 h, prior to test compound addition. Each preparation was washed twice at 15 min intervals during the equilibration.

Histamine (1.7 μM; approximately $EC_{60-70}$) or 5-hydroxytryptamine (5-HT, 2.6 μM; approximately $EC_{60-70}$) was applied for 5 min and the amplitude of the contraction recorded. The histamine or 5-HT was then washed out until the ileal tissue returned to baseline. Five min after returning to baseline test compound (3 and 30 μM) was applied and the amplitude of the contraction (if any) was recorded. In the continuous presence of test compound, histamine or 5-HT was re-applied and the inhibition of the response was recorded.

The results are shown in Table 8 below.

TABLE 8

Effect of test compounds on guinea pig ileum and on histamine and 5-HT-induced contractions in guinea pig ileum

| Compound | Inhibition of histamine-induced contraction (%) | | Contraction of guinea pig ileum relative to histamine-induced contraction | | Inhibition of 5-HT-induced contraction (%) | | Contraction of guinea pig ileum relative to 5-HT-induced contraction | |
|---|---|---|---|---|---|---|---|---|
| | 3 μM | 30 μM | 3 μM | 30 μM | 3 μM | 30 μM | 3 μM | 30 μM |
| 2 | 0 | 28 | 0 | 0 | 8 | 79 | 0 | 0 |
| 4 | 7 | 14 | 0 | 0 | 0 | 10 | 0 | 0 |
| 15 | 0 | 13 | 0 | 0 | 0 | 54 | 0 | 7 |
| 16 | 4 | 22 | 0 | 0 | 0 | 28 | 0 | 9 |

TABLE 8-continued

Effect of test compounds on guinea pig ileum and on histamine and 5-HT-induced contractions in guinea pig ileum

| Compound | Inhibition of histamine-induced contraction (%) | | Contraction of guinea pig ileum relative to histamine-induced contraction | | Inhibition of 5-HT-induced contraction (%) | | Contraction of guinea pig ileum relative to 5-HT-induced contraction | |
|---|---|---|---|---|---|---|---|---|
| | 3 µM | 30 µM | 3 µM | 30 µM | 3 µM | 30 µM | 3 µM | 30 µM |
| 69 | 9 | 41 | 0 | 0 | 9 | 63 | 0 | 0 |
| 11 | 0 | 32 | 0 | 7 | 0 | 53 | 0 | 24 |
| 6 | 0 | 12 | 0 | 0 | 0 | 34 | 0 | 0 |
| 7 | 4 | 12 | 0 | 0 | 0 | 26 | 0 | 0 |
| 12 | 3 | 41 | 0 | 3 | 3 | 47 | 0 | 0 |
| 32 | 15 | 89 | 0 | 0 | 9 | 93 | 0 | 0 |
| 3-Gingerdione | 5 | 14 | 0 | 0 | 0 | 5 | 0 | 0 |
| 1 | 0 | 11 | 0 | 0 | 0 | 20 | 0 | 0 |
| 14 | 10 | 54 | 0 | 13 | 10 | 74 | 3 | 9 |
| 17 | 3 | 29 | 0 | 2 | 6 | 42 | 0 | 6 |
| 34 | 11 | 22 | 0 | 0 | 2 | 43 | 0 | 0 |
| 47 | 5 | 23 | 0 | 0 | 6 | 33 | 0 | 0 |
| 13 | 6 | 78 | 2 | 28 | 15 | 66 | 0 | 28 |
| 30 | 8 | 89 | 0 | 4 | 6 | N/D | 7 | 62 |
| 29 | 17 | 89 | 2 | 34 | 5 | N/D | 0 | 51 |
| 18 | 0 | 7 | 0 | 0 | 0 | 3 | 0 | 0 |
| 19 | 8 | 81 | 0 | 0 | 13 | 39 | 0 | 0 |
| 20 | 0 | 22 | 0 | 0 | 2 | 74 | 0 | 0 |
| 21 | 9 | 68 | 0 | 0 | 9 | 49 | 0 | 0 |
| 22 | 11 | 65 | 0 | 0 | 18 | 94 | 0 | 0 |
| 23 | 8 | 37 | 0 | 0 | 11 | 25 | 0 | 0 |
| 24 | 12 | 59 | 0 | 0 | 5 | 98 | 0 | 0 |
| 25 | 1 | 43 | 0 | 0 | 12 | 35 | 0 | 0 |
| 26 | 3 | 34 | 0 | 0 | 7 | 40 | 0 | 0 |
| 27 | 2 | 68 | 0 | 0 | 1 | 63 | 0 | 0 |
| 28 | 7 | 18 | 0 | 0 | 6 | 85 | 0 | 0 |
| 31 | 12 | 68 | 0 | 16 | 10 | 96 | 0 | 0 |
| 70 | 4 | 29 | 0 | 0 | 2 | 46 | 0 | 0 |
| 71 | 0 | 35 | 0 | 0 | 3 | 53 | 0 | 0 |
| 74 | 1 | 41 | 0 | 0 | 10 | 89 | 0 | 0 |
| 76 | 9 | 81 | 0 | 0 | 26 | 72 | 0 | 0 |
| 80 | 2 | 62 | 0 | 13 | 14 | 68 | 0 | 19 |
| 81 | 22 | 94 | 0 | 0 | 21 | 95 | 0 | 0 |
| 82 | 12 | 20 | 0 | 0 | 13 | 83 | 0 | 0 |
| 83 | 16 | 17 | 16 | 36 | 4 | 11 | 24 | 31 |
| 84 | 19 | 66 | 0 | 0 | 22 | 100 | 0 | 0 |
| 86 | 0 | 9 | 0 | 0 | 4 | 19 | 0 | 0 |
| 87 | 0 | 58 | 0 | 0 | 15 | 93 | 0 | 0 |

N/D: Not determined due to spasmodic activity of the compound

Example 64

Anti-remodelling Activity in Human Lung Fibroblasts (Assay 4)

A human foetal lung fibroblast cell line (HFL1 cells; ATCC accession number CCl-153) was used in this assay. The cells were cultured in medium containing a low level of foetal bovine serum (FBS; 0.1%) for 24 h. After 24 h of culturing the medium was changed to: (a) Control medium (medium containing 10% FBS, 1% phosphate saline and 0.5 mM L-glutamine), (b) Control medium and transforming growth factor beta (TGFβ; 10 ng/ml), (c) Control medium and TGFβ and test compounds (3 and 30 µM). The medium was collected after 24 h and the total mRNA extracted in Tri-reagent. The level of mRNA coding for α-smooth muscle actin (α-SMA) was assessed by real-time reverse transcription-polymerase chain reaction (rtRT-PCR) using primer couples that allow the amplification of α-SMA mRNA. Liver glyceraldehydes 3-phosphate dehydrogenase (GADPH) was used as a reference marker in this experiment. The inhibition of the TGTβ-induced overexpression of α-SMA mRNA by the test compounds was quantified.

The results are shown in Table 9 below.

TABLE 9

Effect of test compounds on anti-remodelling activity in human lung fibroblasts

| Compound | Inhibition of α-SMA mRNA synthesis (%) | |
|---|---|---|
| | 3 µM | 30 µM |
| 2 | 5 | 27 |
| 4 | −3 | 17 |
| 15 | 13 | 29 |

TABLE 9-continued

Effect of test compounds on anti-remodelling activity in human lung fibroblasts

| Compound | Inhibition of α-SMA mRNA synthesis (%) | |
|---|---|---|
| | 3 μM | 30 μM |
| 16 | −8 | 10 |
| 69 | 10 | 34 |
| 11 | 8 | 39 |
| 6 | −12 | 22 |
| 7 | −8 | 9 |
| 12 | 9 | 34 |
| 32 | 13 | 58 |
| 3-Gingerdione | 13 | 24 |
| 1 | 12 | 34 |
| 14 | 11 | 17 |
| 17 | −1 | 31 |
| 13 | 14 | 77 |
| 18 | 13 | 79 |
| 19 | 57 | 97 |
| 20 | −8 | 11 |
| 21 | 6 | 54 |
| 22 | −5 | 25 |
| 23 | 13 | 79 |
| 24 | 8 | 80 |
| 25 | −3 | 20 |
| 26 | 2 | 64 |
| 27 | 6 | 79 |
| 28 | 12 | 47 |
| 29 | 33 | 86 |
| 30 | 84 | 100 |
| 31 | 34 | 80 |
| 71 | −1 | 20 |
| 74 | −4 | 53 |
| 76 | −1 | 94 |
| 80 | 4 | 29 |
| 81 | −2 | 55 |
| 82 | −3 | 39 |
| 83 | −2 | 86 |
| 84 | 6 | 65 |

The test compounds displayed a range of anti-remodelling activity at 3 and 30 μM.

Example 65

Anti-inflammatory Action in Human Diploid Lung Fibroblasts (Assay 5)

Human diploid lung fibroblasts (WI-38 cells) were incubated overnight in the presence of IL-1α (1 nM) and test compound (3 and 30 μM) in modified Eagle medium at pH 7.3 containing foetal bovine serum (10%) at 37° C. The supernatant was assayed by radioimmunoassay for released $PGE_2$ and the inhibition of $PGE_2$ by test compound calculated (Table 10). The viability of the cells was then assessed by washing with Roswell Park Memorial Institute medium and adding Alamar Blue reagent before being incubated at 37° C. for 4 h. Living cells take up Alamar Blue and emit fluorescence when excited. Fluorescence intensity was measured using a SpectroFluor Plus plate reader with excitation at 530 nm and emission at 590 nm (Table 10).

TABLE 10

Anti-inflammatory effect of test compounds on IL-1α-induced $PGE_2$ release in human lung fibroblasts

| Compound | Inhibition of IL-1α-induced $PGE_2$ release (%) | | Decrease in cell viability (%) | |
|---|---|---|---|---|
| | 3 μM | 30 μM | 3 μM | 30 μM |
| 2 | 88 | 102 | −2 | 4 |
| 4 | 49 | 96 | −3 | 10 |
| 15 | 49 | 95 | −2 | −1 |
| 16 | 32 | 83 | 10 | −9 |
| 69 | 89 | 102 | 3 | 4 |
| 11 | 79 | 100 | 1 | −7 |
| 6 | 88 | 102 | 6 | 4 |
| 7 | 47 | 94 | −4 | 4 |
| 12 | 69 | 101 | 6 | −5 |
| 32 | 67 | 101 | −4 | −3 |
| 3-Gingerdione | 61 | 99 | 4 | 5 |
| 1 | 68 | 101 | 3 | −10 |
| 14 | 77 | 101 | 5 | −4 |
| 17 | 58 | 98 | −1 | 4 |
| 34 | 72 | 109 | 3 | 5 |
| 47 | 10 | 109 | 1 | 11 |
| 13 | 73 | 99 | −4 | −3 |
| 18 | 86 | 99 | 3 | 15 |
| 19 | 73 | 100 | −1 | 57 |
| 20 | 87 | 99 | 3 | 10 |
| 21 | 88 | 99 | 3 | 11 |
| 22 | 93 | 100 | 3 | 9 |
| 23 | 84 | 100 | 6 | 16 |
| 24 | 93 | 100 | 7 | 26 |
| 25 | 58 | 102 | −6 | 0 |
| 26 | 81 | 100 | 3 | 10 |
| 27 | 92 | 99 | 4 | 40 |
| 28 | 87 | 99 | 1 | 6 |
| 29 | 86 | 99 | −1 | 12 |
| 30 | 46 | 99 | −10 | 29 |
| 31 | 83 | 101 | 5 | −7 |
| 70 | 42 | 86 | 0 | 5 |
| 71 | 41 | 95 | −1 | 11 |
| 74 | 99 | 101 | 1 | 16 |
| 76 | 99 | 101 | 4 | 26 |
| 80 | 72 | 102 | 2 | 1 |
| 81 | 62 | 101 | 3 | −7 |
| 82 | 78 | 102 | −4 | 6 |
| 83 | 86 | 102 | 4 | 31 |
| 84 | 101 | 102 | 3 | 12 |
| 86 | 42 | 100 | 7 | 37 |
| 87 | −28 | −62 | N/D | N/D |

N/D: Not determined
The test compounds displayed a range of anti-inflammatory activity, without altering cell viability, in WI-38 cells at 3 and 30 μM.

Example 66

Anti-inflammatory Action in Human Peripheral Blood Mononuclear Leukocytes (Assay 6)

Human peripheral blood mononuclear leukocytes (PBMLs) were isolated using a Ficoll-Paque density gradient. Human peripheral blood mononuclear leukocytes ($5×10^6$ cells) were incubated with A23187 (30 μM), a divalent cation ionophore used to initiate the biosynthesis of arachidonic acid, and with vehicle (0.1% DMSO) or test compound (3 and 30 μM) in Hank's balanced salt solution (HBBS) buffer, pH 7.4 at 37° C. for 15 min. The PBML solution was neutralized with NaOH (1 N) and centrifuged at 1000 g for 10 min and the supernatant collected. The concentration of leukotriene $B_4$ ($LTB_4$) in the supernatant was measured using an enzyme immunoassay kit (Assay Design Inc.). A reduction in the concentration of $LTB_4$ indicated an inhibition of the enzyme 5-lipoxygenase (Table 11).

TABLE 11

Anti-inflammatory effect of test compounds on 5-lipoxygenase (5-LO) activity in human PBMLs

| Compound | Inhibition of 5-LO (%) | |
| --- | --- | --- |
|  | 3 µM | 30 µM |
| 2 | 30 | 76 |
| 4 | 15 | 73 |
| 15 | 16 | 63 |
| 16 | 20 | 73 |
| 69 | 89 | 96 |
| 11 | 47 | 92 |
| 6 | 47 | 78 |
| 7 | 24 | 63 |
| 12 | 41 | 94 |
| 32 | 45 | 96 |
| 3-Gingerdione | −5 | 73 |
| 1 | 26 | 63 |
| 14 | 57 | 96 |
| 17 | 51 | 95 |
| 13 | 51 | 98 |
| 18 | 58 | 94 |
| 19 | 48 | 99 |
| 20 | 58 | 98 |
| 21 | 68 | 98 |
| 22 | 62 | 98 |
| 23 | 63 | 98 |
| 24 | 45 | 97 |
| 25 | 54 | 94 |
| 26 | 60 | 98 |
| 27 | 92 | 98 |
| 28 | 35 | 98 |
| 29 | 47 | 98 |
| 30 | 50 | 99 |
| 31 | 32 | 95 |
| 70 | −1 | 63 |
| 71 | 6 | 48 |
| 74 | 60 | 98 |
| 76 | 74 | 99 |
| 80 | 61 | 97 |
| 81 | 64 | 97 |
| 82 | 48 | 97 |
| 83 | 52 | 99 |
| 84 | 77 | 98 |
| 86 | 52 | 98 |
| 87 | −6 | 19 |

Test compounds displayed a range of anti-inflammatory activity in human PBMLs at 3 and 30 µM.

Example 67

Effect of Compound 2 on Ovalbumin-sensitised Guinea Pigs, a Model of Asthma in Vivo (Assay 7)

Dunkin-Hartley guinea pigs were sensitised to ovalbumin using two interperitoneal injections of ovalbumin (20 µg) in $Al(OH)_3$ gel (1.65 mg) on days 1 and 11. On day 25 compound 2 was administered by oral gavage (30 mg/kg/day) for 7 days. On day 31, approximately 2 h after the last administration of compound 2, each guinea pig was anaesthetised with urethane (1750 mg/kg, i.p.) and artificially ventilated via a tracheal cannula connected to a Fleisch pneumotachograph (size 00) and a differential pressure transducer (±2 cm $H_2O$; PT5, Grass Astro-Med Inc., USA). Total pulmonary resistance ($R_L$) was calculated online by integration of flow, tidal volume and transpulmonary pressure. Pulmonary resistance was recorded for approximately 5 min before ovalbumin (300 µg/ml, i.v) challenge and for approximately 15 min following ovalbumin challenge and was recorded in real time using a computer data acquisition system (Po-ne-Mah, USA).

In the vehicle control group there was a 228±57% increase in pulmonary resistance after exposure to ovalbumin (300 µg/kg, i.v.). In the group orally administered compound 2 the increase in pulmonary resistance following ovalbumin exposure was 132±15%, which was significantly lower than vehicle control.

Example 68

Effect of Compounds 2 and 32 on Ovalbumin-sensitised Mice, a Chronic Model of Asthma in Vivo (Assay 8)

Mice (BALB/c from Harlan-Olac) were sensitised to ovalbumin using two interperitoneal injections of ovalbumin (10 µg) and alum (200 µl) on day 1 and 14 followed by a 20 min, daily exposure to a ovalbumin aerosol (5%) on days 19-23 and then a thrice weekly 20 min, exposure to a ovalbumin aerosol (5%) on days 24-55. On day 35 compound 2 (3 mg/kg/day), compound 32 (30 mg/kg/day), budesonide (1 mg/kg/day) and montelukast (10 mg/kg/day) were administered by oral gavage for 20 days. On day 54, mice were placed in BUXCO four chamber whole body plethysmographs and breathing-associated pressure changes were recorded which were then used to calculate enhanced pause (penH), a measurement of airways resistance, in response to a methacholine challenge.

Following a methacholine challenge (50 mg/kg) there was an increase in penH in ovalbumin-sensitised mice compared to control mice (Table 12, and the accompanying drawing (FIG. 1)). Compound 2 (3 mg/kg/day) and compound 32 (30 mg/kg/day), decreased the methacholine-induced increase in penH (Table 12, FIG. 1). By contrast, budesonide (1 mg/kg/day) and montelukast (10 mg/kg/day) did not decrease the methacholine-induced increase in penH (Table 12, FIG. 1).

On day 55 the mice were killed and brochoalveolar lavage (BAL) fluid was collected and cytospins prepared to measure eosinophil infiltration. In addition, concentrations of interleukin-4 (IL-4) and interleukin-13 (IL-13) were measured in the BAL fluid. Furthermore, lung samples were taken, examined by a histopathologist and scored using a grading system to describe the degree of lung remodelling. Compound 2, compound 32, budesonide and montelukast reduced eosinophil infiltration into the lung and IL-13 concentrations in the BAL. Furthermore, compound 32, budenoside and montelukast reduced IL-4 concentration in the BAL. In addition, compound 2, compound 32, budesonide and montelukast reduced the amount of lung remodelling (Table 12).

TABLE 12

Summary of the effect of compounds 2, 32, budesonide and montelukast on penH, eosinophil infiltration, IL-4 concentration, IL-13 concentration and lung remodelling in ovalbumin-sensitised mice

| Condition | Percent of control (mean ± s.e.mean) | | | | |
|---|---|---|---|---|---|
| | Increase in penH | Eosinophil infiltration | IL-4 concentration | IL-13 concentration | Histo-pathology score |
| Control | 100 ± 16.4 | 100 ± 15.9 | 100 ± 22.3 | 100 ± 26.3 | 100 ± 66.6 |
| Sensitised | 193.0 ± 61.7 | 192.1 ± 33.2 | 231.2 ± 62.4 | 241.9 ± 89.3 | 541.6 ± 36.1 |
| 2 (3 mg/kg/day) | 107.4 ± 21.5 | 83.0 ± 10.8 | 238.2 ± 57.1 | 183.0 ± 60.9 | 450.0 ± 33.4 |
| 32 (30 mg/kg/day) | 153.5 ± 29.0 | 106.6 ± 19.9 | 168.0 ± 50.8 | 148.7 ± 88.4 | 339.3 ± 45.0 |
| budesonide (1 mg/kg/day) | 184.6 ± 27.7 | 38.4 ± 5.4 | 144.2 ± 59.7 | 199.3 ± 110.1 | 200.0 ± 27.6 |
| montelukast (10 mg/kg/day) | 187.6 ± 31.9 | 124.3 ± 24.8 | 58.2 ± 37.2 | 73.2 ± 55.3 | 450.0 ± 38.25 |

The foregoing broadly describes the present invention, without limitation. Variations and modifications as will be readily apparent to those of ordinary skill in this art are intended to be included within the scope of this application and subsequent patents.

The invention claimed is:

1. A method of treatment comprising administering to a human or nonhuman animal a compound for the treatment of one or more conditions selected from the group consisting of hypersensitivity, smooth muscle disorders, spasmodic conditions, allergic conditions, inflammatory conditions and pain, the compound having general formula I:

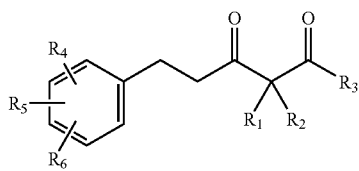

wherein:

$R_1$ and $R_2$ are, independently of each other, selected from hydrogen, optionally substituted $C_{1-10}$alkyl, optionally substituted —CO—($C_{1-10}$alkyl), optionally substituted $C_{3-10}$cycloalkyl, optionally substituted —CO—($C_{3-10}$cycloalkyl), optionally substituted $C_{2-10}$alkenyl, optionally substituted —CO—($C_{2-10}$alkenyl), optionally substituted aryl, and optionally substituted —CO-aryl, or $R_1$ and $R_2$ together represent an optionally substituted saturated or unsaturated $C_{1-10}$alkylidene group, or an optionally substituted saturated or unsaturated $C_{3-10}$cycloalkylidene group, or $R_1$ and $R_2$ together with the carbon atom to which they are attached represent an optionally substituted saturated or unsaturated organic ring containing 3, 4, 5, 6, 7 or 8 ring carbon atoms and optionally 1, 2 or 3 ring heteroatoms selected from O, N and S;

$R_3$ is selected from the group consisting of $C_{1-10}$alkyl, optionally substituted $C_{3-10}$cycloalkyl, optionally substituted $C_{2-10}$alkenyl, optionally substituted aryl, and $C_{1-10}$alkyl substituted with one or more substituents, which may be the same or different, selected from: halo, $C_{1-6}$ alkyl, $C_{3-6}$ cycloalkyl, hydroxy, $C_{1-6}$ alkoxy, $C_{2-6}$ alkenyloxy, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{6-12}$ aryl, $C_{6-12}$ arylamino, di-$C_{6-12}$ arylamino, $C_{6-12}$ aroylamino, di-$C_{6-12}$ aroylamino, $C_{6-12}$ arylamido, carboxy, $C_{1-6}$ alkoxycarbonyl, ($C_{6-12}$ ar)($C_{1-10}$ alkoxy) carbonyl, carbamoyl, and any of the above in which a hydrocarbyl moiety is itself substituted by halo, hydroxy, amino, nitro, carbamoyl or carboxy, but $R_3$ not being phenylethyl;

$R_4$, $R_5$ and $R_6$ are, independently of each other, selected from the group consisting of hydrogen, optionally substituted $C_{1-10}$alkyl, OH, optionally substituted $C_{1-10}$ alkoxy, halo, optionally substituted aryloxy, optionally substituted ($C_{1-10}$alkyl)-S(O)$_n$— where n=0, 1 or 2, optionally substituted aryl-S(O)$_n$—where n=0, 1 or 2, or $R_4$ and $R_5$ together represent an optionally substituted saturated or unsaturated organic chain containing 1, 2, 3, 4, 5, 6 or 7 chain carbon atoms and optionally 1, 2 or 3 chain heteroatoms selected from O, N and S, provided that the chain is at least 3 atoms long;

with the proviso that, when $R_1$=$R_2$=hydrogen, then any optionally substituted $C_{1-10}$alkyl or optionally substituted $C_{2-10}$ alkenyl for $R_3$ must have a branch point at one or more of the α and β positions counted from the carbonyl group (or tautomeric form thereof) to which $R_3$ is attached;

or a physiologically acceptable salt or complex thereof;

excluding 2-[4-[3-oxo-5-phenyl-2-(3,4,5-trimethoxybenzoyl)-pentyl]-phenoxy]-benzoic acid and its benzyl ester.

2. A method of treatment comprising administering to a human or nonhuman animal a compound for the treatment of one or more conditions selected from the group consisting of asthma, cough, pruritus, food intolerance, psoriasis, croup, irritable bowel syndrome, tinnitus, Meniere's disease, stress-induced ulceration, acetylsalicylic acid-induced ulceration, primary dysmenorrhea, diarrhoea, gastrointestinal cramps, diverticular disease, achalasia, Hirschsprung's disease, gastro-oesophageal reflux disease, myotonic dystrophy, gallstone disease, constipation, post-surgical gastroparesis syndrome, paralytic ileus, post-operative ileus, diabetic gastroparesis, bowel paresis, intestinal pseudo-obstruction, peripheral arterial diseases, Raynaud's syndrome, coronary artery spasm, angina, peripheral arterial disease, hypertension, hypotension, vascular paresis, bladder disorders, nausea, allergic rhinitis, allergic dermatitis, inflammation, inflammatory bowel disease, ileitis, pancreatitis, cholecystitis, non-allergic rhinitis, oesophagitis, osteoarthritis, rheumatoid arthritis, Huntington's disease, cerebral ischemia, acute inflammatory pain, neuropathic pain, visceral pain, dental pain, headaches, abnormal gut function, as a calmative for the gut, abnormal breathing, motion sickness, vertigo, sore throat, nausea, vomiting, abnormal digestion, upset stomach, cold hands and feet, abnormal menstruation, abnormal blood pressure, abnormal bowel movement, colds and flu, congestion, headache, muscle soreness, mild aches and pains, toothache, mouth ulcers, cellulite occurrence, and overweight, the compound having general formula I:

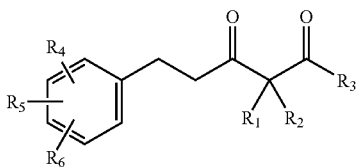

wherein:
  $R_1$ and $R_2$ are, independently of each other, selected from the group consisting of hydrogen, optionally substituted $C_{1-10}$alkyl, optionally substituted —CO—($C_{1-10}$alkyl), optionally substituted $C_{3-10}$cycloalkyl, optionally substituted —CO—($C_{3-10}$cycloalkyl), optionally substituted $C_{2-10}$alkenyl, optionally substituted —CO—($C_{2-10}$alkenyl), optionally substituted aryl, and optionally substituted —CO-aryl, or $R_1$ and $R_2$ together represent an optionally substituted saturated or unsaturated $C_{1-10}$alkylidene group, or an optionally substituted saturated or unsaturated $C_{3-10}$cycloalkylidene group, or $R_1$ and $R_2$ together with the carbon atom to which they are attached represent an optionally substituted saturated or unsaturated organic ring containing 3, 4, 5, 6, 7 or 8 ring carbon atoms and optionally 1, 2 or 3 ring heteroatoms selected from O, N and S;
  $R_3$ is selected from the group consisting of $C_{1-10}$alkyl, optionally substituted $C_{3-10}$cycloalkyl, optionally substituted $C_{2-10}$alkenyl, optionally substituted aryl, and $C_{1-10}$alkyl substituted with one or more substituents, which may be the same or different, selected from: halo, $C_{1-6}$ alkyl, $C_{3-6}$ cycloalkyl, hydroxy, $C_{1-6}$ alkoxy, $C_{2-6}$ alkenyloxy, amino, nitro, $C_{1-6}$ alkylamino, $C_{2-6}$ alkenylamino, di-$C_{1-6}$alkylamino, $C_{1-6}$ acylamino, di-$C_{1-6}$ acylamino, $C_{6-12}$ aryl $C_{6-12}$ arylamino, di-$C_{6-12}$ arylamino, $C_{6-12}$ aroylamino, di-$C_{6-12}$ aroylamino, $C_{6-12}$ arylamido, carboxy, $C_{1-6}$ alkoxycarbonyl, ($C_{6-12}$ ar)($C_{1-10}$ alkoxy) carbonyl, carbamoyl, and any of the above in which a hydrocarbyl moiety is itself substituted by halo, hydroxy, amino, nitro, carbamoyl or carboxy, but $R_3$ not being phenylethyl;
  $R_4$, $R_5$ and $R_6$ are, independently of each other, selected from the group consisting of hydrogen, optionally substituted $C_{1-10}$alkyl, OH, optionally substituted $C_{1-10}$ alkoxy, halo, optionally substituted aryloxy, optionally substituted ($C_{1-10}$alkyl)-S(O)$_n$— where n=0, 1 or 2, optionally substituted aryl-S(O)$_n$— where n=0, 1 or 2, or $R_4$ and $R_5$ together represent an optionally substituted saturated or unsaturated organic chain containing 1, 2, 3, 4, 5, 6 or 7 chain carbon atoms and optionally 1, 2 or 3 chain heteroatoms selected from O, N and S, provided that the chain is at least 3 atoms long;
  with the proviso that, when $R_1$=$R_2$=hydrogen, then any optionally substituted $C_{1-10}$ alkyl or optionally substituted $C_{2-10}$ alkenyl for $R_3$ must have a branch point at one or more of the α and β positions counted from the carbonyl group (or tautomeric form thereof) to which $R_3$ is attached;
  or a physiologically acceptable salt or complex thereof;
  excluding 2-[4-[3-oxo-5-phenyl-2-(3,4,5-trimethoxybenzoyl)-pentyl]-phenoxy]-benzoic acid and its benzyl ester.

3. The method according to claim 1, wherein, independently of each other,
  $R_1$ is selected from the group consisting of hydrogen and optionally substituted $C_{1-10}$ alkyl;
  $R_2$ is selected from the group consisting of hydrogen and optionally substituted $C_{1-10}$ alkyl;
  $R_3$ is selected from the group consisting of $C_{1-10}$ alkyl, optionally substituted $C_{3-10}$ cycloalkyl, optionally substituted aryl, and $C_{1-10}$alkyl substituted with one or more substituents, which may be the same or different, selected from: halo, $C_{1-6}$ alkyl, $C_{3-6}$ cycloalkyl, hydroxy, $C_{1-6}$ alkoxy, $C_{2-6}$ alkenyloxy, amino, nitro, $C_{2-6}$ alkylamino, $C_{2-6}$ alkenylamino, di-$C_{1-6}$ alkylamino, $C_{1-6}$ acylamino, di-$C_{1-6}$ acylamino, $C_{6-12}$ aryl, $C_{6-12}$ arylamino, di-$C_{6-12}$ arylamino, $C_{6-12}$ aroylamino, di-$C_{6-12}$ aroylamino, $C_{6-12}$ arylamido, carboxy, $C_{1-6}$ alkoxycarbonyl, ($C_{6-12}$ ar)($C_{1-10}$ alkoxy)carbonyl, carbamoyl, and any of the above in which a hydrocarbyl moiety is itself substituted by halo, hydroxy, amino, nitro, carbamoyl or carboxy, but $R_3$ not being phenylethyl;
  $R_4$ is hydroxyl or optionally substituted $C_{1-4}$ alkoxy;
  $R_5$ is hydroxyl or optionally substituted $C_{1-4}$ alkoxy; and
  $R_6$ is hydrogen.

4. The method according to claim 1, wherein, independently of each other:
  $R_1$ is selected from the group consisting of hydrogen, unsubstituted $C_{1-6}$ alkyl and phenyl-sub stituted $C_{1-6}$ alkyl;
  $R_2$ is selected from the group consisting of hydrogen, unsubstituted $C_{1-6}$ alkyl and phenyl-substituted $C_{1-6}$ alkyl;
  $R_3$ is selected from the group consisting of unsubstituted $C_{1-6}$ alkyl, ($C_{3-6}$ cycloalkyl)-substituted $C_{1-6}$ alkyl, unsubstituted $C_{3-6}$ cycloalkyl, unsubstituted phenyl, mono or poly phenyl-substituted phenyl, ($C_{1-6}$ alkyl)-substituted phenyl, ($C_{1-6}$ alkoxy)-substituted phenyl, mono or poly halo-substituted phenyl where polyhalo substituents may be the same or different, hydroxyl-substituted phenyl, ($C_{1-6}$ alkoxy)(hydroxyl)-disubstituted phenyl, ($C_{1-6}$ alkoxy) carbonyl-substituted phenyl and unsubstituted naphthyl;
  $R_4$ is unsubstituted methoxy;
  $R_5$ is hydroxyl; and $R_6$ is hydrogen.

5. The method according to claim 1, wherein the compound is selected from the group consisting of:
  1-(4-Hydroxy-3-methoxyphenyl)-6-methyl-heptane-3,5-dione) (Compound 1);
  6,6-Dimethyl-1-(4-hydroxy-3-methoxyphenyl)-heptane-3,5-dione (Compound 2);
  7,7-Dimethyl-1-(4-hydroxy-3-methoxyphenyl)-octane-3,5-dione (Compound 3);
  1-(4-Hydroxy-3-methoxyphenyl)-4,6,6-trimethyl-heptane-3,5-dione (Compound 4);
  1-cyclopropyl-5-(4-hydroxy-3-methoxyphenyl)-pentane-1,3-dione (Compound 5);
  5-(4-Hydroxy-3-methoxyphenyl)-1-(1-methylcyclopropyl)-pentane-1,3-dione (Compound 6);
  5-(4-Hydroxy-3-methoxyphenyl)-2-methyl-1-(1-methylcyclopropyl)-pentane-1,3-dione (Compound 7);

1-Cyclopentyl-5-(4-hydroxy-3-methoxyphenyl)-pentane-1,3-dione (Compound 8);
1-(4-Hydroxy-3-methoxyphenyl)-6-methyloctane-3,5-dione (Compound 9);
5-(4-Hydroxy-3-methoxy-phenyl)-1-(1-methyl-cyclohexyl)-pentane-1,3-dione (Compound 10);
5-(4-Hydroxy-3-methoxy-phenyl)-2-methyl-1-phenyl-pentane-1,3-dione (Compound 11);
2-Ethyl-5-(4-hydroxy-3-methoxyphenyl)-1-phenyl-pentane-1,3-dione (Compound 12);
2-Benzyl-5-(4-hydroxy-3-methoxyphenyl)-1-phenylpentane-1,3-dione (Compound 13);
5-(4-Hydroxy-3-methoxyphenyl)-2-methyl-1-p-tolyl-pentane-1,3-dione (Compound 14);
1,5-Bis(4-hydroxy-3-methoxyphenyl)-pentane-1,3-dione (Compound 15);
1,5-Bis(4-hydroxy-3-methoxyphenyl)-2-methyl-pentane-1,3-dione (Compound 16);
5-(4-Hydroxy-3-methoxyphenyl)-1-(4-methoxyphenyl)-2-methyl-pentane-1,3-dione (Compound 17);
1-(Biphenyl-4-yl)-5-(4-hydroxy-3-methoxyphenyl)-pentane-1,3-dione (Compound 18);
1-(Biphenyl-2-yl)-5-(4-hydroxy-3-methoxyphenyl)-pentane-1,3-dione (Compound 19);
1-(4-Fluorophenyl)-5-(4-hydroxy-3-methoxyphenyl)-pentane-1,3-dione (Compound 20);
1-(4-Chlorophenyl)-5-(4-hydroxy-3-methoxyphenyl)pentane-1,3-dione (Compound 21);
1-(3-Chlorophenyl)-5-(4-hydroxy-3-methoxyphenyl)pentane-1,3-dione (Compound 22);
1-(3,4-Dihlorophenyl)-5-(4-hydroxy-3-methoxyphenyl)pentane-1,3-dione (Compound 23);
1-(2,4-Dihlorophenyl)-5-(4-hydroxy-3-methoxyphenyl)pentane-1,3-dione (Compound 24);
Methyl 4-(5-(4-hydroxy-3-methoxyphenyl)-3-oxopentanoyl)benzoate (Compound 25);
5-(4-Hydroxy-3-methoxyphenyl)-1-(naphthalene-2-yl)-pentane-1,3-dione (Compound 26);
5-(4-Hydroxy-3-methoxyphenyl)-1-(naphthalene-1-yl)-pentane-1,3-dione (Compound 27);
6-(4-Hydroxy-3-methoxyphenyl)-1-phenyl-hexane-2,4-dione (Compound 28);
6-(4-Hydroxy-3-methoxyphenyl)-1-naphthalen-1-yl-hexane-2,4-dione (Compound 29);
6-(4-Hydroxy-3-methoxyphenyl)-1,1-diphenyl-hexane-2,4-dione (Compound 30);
6-(4-Hydroxy-3-methoxyphenyl)-1,1-dimethyl-1-phenyl-hexane-2,4-dione (Compound 31);
2,2-Dimethyl-5-(4-hydroxy-3-methoxy-phenyl)-1-phenyl-pentane-1,3-dione (Compound 32);
5-(4-Hydroxy-3-methoxyphenyl)-1-phenyl-pentane-1,3-dione (Compound 69);
5-(4-Hydroxy-3-methoxyphenyl)-2,2-dimethyl-1-(1-methylcyclopropyl)pentane-1,3-dione (Compound 70);
1-(4-Hydroxy-3-methoxyphenyl)-4,4,6,6-tetramethylheptane-3,5-dione (Compound 71);
1,5-bis(4-Hydroxy-3-methoxyphenyl)-2,2-dimethylpentane-1,3-dione (Compound 72);
1-(4-Fluorophenyl)-5-(4-hydroxy-3-methoxyphenyl)-2,2-dimethylpentane-1,3-dione (Compound 73);
1-(2-Chlorophenyl)-5-(4-hydroxy-3-methoxyphenyl)pentane-1,3-dione (Compound 74);
1-(4-chloro-3-methylphenyl)-5-(4-hydroxy-3-methoxyphenyl)pentane-1,3-dione (Compound 75);
1-(4-Chloro-2-methylphenyl)-5-(4-hydroxy-3-methoxyphenyl)pentane-1,3-dione (Compound 76);
1-(3-chloro-2-methylphenyl)-5-(4-hydroxy-3-methoxyphenyl)pentane-1,3-dione (Compound 77);
1-(3-chloro-4-methylphenyl)-5-(4-hydroxy-3-methoxyphenyl)pentane-1,3-dione (Compound 78);
5-(4-Hydroxy-3-methoxyphenyl)-2,2-dimethyl-1-(naphthalen-2-yl)pentane-1,3-dione (Compound 79);
5-(4-Hydroxy-3-methoxyphenyl)-1-p-tolylpentane-1,3-dione (Compound 80);
5-(4-Hydroxy-3-methoxyphenyl)-2,2-dimethyl-1-p-tolyl-pentane-1,3-dione (Compound 81);
1-(4-Cyanophenyl)-5-(4-hydroxy-3-methoxyphenyl)pentane-1,3-dione (Compound 82);
1-(4-tert-Butylphenyl)-5-(4-hydroxy-3-methoxyphenyl)pentane-1,3-dione (Compound 83);
5-(4-Hydroxy-3-methoxyphenyl)-1-o-tolylpentane-1,3-dione (Compound 84);
5-(4-Hydroxy-3-methoxyphenyl)-1-m-tolylpentane-1,3-dione (Compound 85);
5-(2-Chloro-4-hydroxy-5-methoxyphenyl)-1-(naphthalene-3-yl)pentane-1,3-dione (Compound 86);
5-(4-(2-aminoethoxy)-3-methoxyphenyl)-1-phenylpentane-1,3-dione hydrochloride (Compound 87);
5-(4-(2-Aminoethoxy)-3-methoxyphenyl)-1-phenylpentane-1,3-dione hydrochloride (Compound 88); and
5-(3-Ethoxy-4-hydroxyphenyl)-1-phenylpentane-1,3-dione (Compound 89).

6. A method of treatment of one or more conditions selected from the group consisting of: hypersensitivity, smooth muscle disorders, spasmodic conditions, allergic conditions, inflammatory conditions, pain, asthma, cough, pruritus, food intolerance, psoriasis, croup, irritable bowel syndrome, tinnitus, Meniere's disease, stress-induced ulceration, acetylsalicylic acid-induced ulceration, primary dysmenorrhea, diarrhoea, gastrointestinal cramps, diverticular disease, achalasia, Hirschsprung's disease, gastro-oesophageal reflux disease, myotonic dystrophy, gallstone disease, constipation, post-surgical gastroparesis syndrome, paralytic ileus, post-operative ileus, diabetic gastroparesis, bowel paresis, intestinal pseudo-obstruction, peripheral arterial diseases, Raynaud's syndrome, coronary artery spasm, angina, peripheral arterial disease, hypertension, hypotension, vascular paresis, bladder disorders, nausea, allergic rhinitis, allergic dermatitis, inflammation, inflammatory bowel disease, ileitis, pancreatitis, cholecystitis, non-allergic rhinitis, oesophagitis, osteoarthritis, rheumatoid arthritis, Huntington's disease, cerebral ischemia, acute inflammatory pain, neuropathic pain, visceral pain, dental pain, headaches, abnormal gut function, as a calmative for the gut, abnormal breathing, motion sickness, vertigo, sore throat, vomiting, abnormal digestion, upset stomach, cold hands and feet, abnormal menstruation, abnormal blood pressure, abnormal bowel movement, colds and flu, congestion, headache, muscle soreness, mild aches and pains, toothache, mouth ulcers, cellulite occurrence, and overweight, comprising administering to a human or non-human patient in need thereof a compound of formula I:

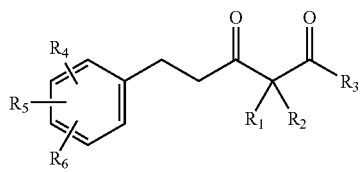

wherein:
- $R_1$ and $R_2$ are, independently of each other, selected from the group consisting of hydrogen, optionally substituted $C_{1-10}$ alkyl, optionally substituted —CO—($C_{1-10}$alkyl), optionally substituted $C_{3-10}$cycloalkyl, optionally substituted —CO—($C_{3-10}$cycloalkyl), optionally substituted $C_{2-10}$alkenyl, optionally substituted —CO—($C_{2-10}$alkenyl), optionally substituted aryl, and optionally substituted —CO-aryl, or $R_1$ and $R_2$ together represent an optionally substituted saturated or unsaturated $C_{1-10}$alkylidene group, or an optionally substituted saturated or unsaturated $C_{1-3}$cycloalkylidene group, or $R_1$ and $R_2$ together with the carbon atom to which they are attached represent an optionally substituted saturated or unsaturated organic ring containing 3, 4, 5, 6, 7 or 8 ring carbon atoms and optionally 1, 2 or 3 ring heteroatoms selected from O, N and S;
- $R_3$ is selected from the group consisting of $C_{1-10}$alkyl, optionally substituted $C_{3-10}$cycloalkyl, optionally substituted $C_{2-10}$alkenyl, optionally substituted aryl, and $C_{1-10}$alkyl substituted with one or more substituents, which may be the same or different, selected from: halo, $C_{1-6}$alkyl, $C_{3-6}$ cycloalkyl, hydroxy, $C_{1-6}$ alkoxy, $C_{2-6}$ alkenyloxy, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{6-12}$ aryl, $C_{6-12}$ arylamino, di-$C_{6-12}$ arylamino, $C_{6-12}$ aroylamino, di-$C_{6-12}$ aroylamino, $C_{6-12}$ arylamido, carboxy, $C_{1-6}$ alkoxycarbonyl, ($C_{6-12}$ ar)($C_{1-10}$ alkoxy)carbonyl, carbamoyl, and any of the above in which a hydrocarbyl moiety is itself substituted by halo, hydroxy, amino, nitro, carbamoyl or carboxy, but $R_3$ not being phenylethyl;
- $R_4$, $R_5$ and $R_6$ are, independently of each other, selected from the group consisting of hydrogen, optionally substituted $C_{1-10}$alkyl, OH, optionally substituted $C_{1-10}$alkoxy, halo, optionally substituted aryloxy, optionally substituted ($C_{1-10}$alkyl)—S(O)$_n$— where n=0, 1 or 2, optionally substituted aryl-S(O)$_n$— where n=0, 1 or 2, or $R_4$ and $R_5$ together represent an optionally substituted saturated or unsaturated organic chain containing 1, 2, 3, 4, 5, 6 or 7 chain carbon atoms and optionally 1, 2 or 3 chain heteroatoms selected from O, N and S, provided that the chain is at least 3 atoms long;
- with the proviso that, when $R_1=R_2$=hydrogen, then any optionally substituted $C_{1-10}$alkyl or optionally substituted $C_{2-10}$alkenyl for $R_3$ must have a branch point at one or more of the α and β positions counted from the carbonyl group (or tautomeric form thereof) to which $R_3$ is attached;

or a physiologically acceptable salt or complex thereof;
excluding 2-[4-[3-oxo-5-phenyl-2-(3,4,5-trimethoxybenzoyl)-pentyl]-phenoxy]-benzoic acid and its benzyl ester.

7. A pharmaceutical composition comprising a compound of formula I or a physiologically acceptable salt or complex thereof and a physiologically acceptable carrier thereof:

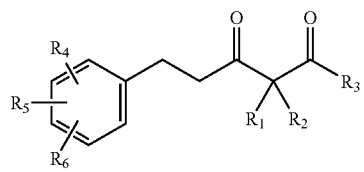

I wherein:
- $R_1$ and $R_2$ are, independently of each other, selected from the group consisting of hydrogen, optionally substituted $C_{1-10}$alkyl, optionally substituted —CO—($C_{1-10}$alkyl), optionally substituted $C_{3-10}$cycloalkyl, optionally substituted —CO—($C_{3-10}$cycloalkyl), optionally substituted $C_{2-10}$alkenyl, optionally substituted —CO—($C_{2-10}$alkenyl), optionally substituted aryl, and optionally substituted —CO-aryl, or $R_1$ and $R_2$ together represent an optionally substituted saturated or unsaturated $C_{1-10}$alkylidene group, or an optionally substituted saturated or unsaturated $C_{3-10}$cycloalkylidene group, or $R_1$ and $R_2$ together with the carbon atom to which they are attached represent an optionally substituted saturated or unsaturated organic ring containing 3, 4, 5, 6, 7 or 8 ring carbon atoms and optionally 1, 2 or 3 ring heteroatoms selected from O, N and S;
- $R_3$ is selected from the group consisting of $C_{1-10}$alkyl, optionally substituted $C_{3-10}$cycloalkyl, optionally substituted $C_{2-10}$alkenyl, optionally substituted aryl, and $C_{1-10}$alkyl substituted with one or more substituents, which may be the same or different, selected from: halo, $C_{1-6}$ alkyl, $C_{3-6}$ cycloalkyl, hydroxy, $C_{1-6}$ alkoxy, $C_{2-6}$ alkenyloxy, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{6-12}$ aryl $C_{6-12}$ arylamino, di-$C_{6-12}$ arylamino, $C_{6-12}$ aroylamino, di-$C_{6-12}$ aroylamino, $C_{6-12}$ arylamido, carboxy, $C_{1-6}$ alkoxycarbonyl, ($C_{6-12}$ ar)($C_{1-10}$ alkoxy)carbonyl, carbamoyl, and any of the above in which a hydrocarbyl moiety is itself substituted by halo, hydroxy, amino, nitro, carbamoyl or carboxy, but $R_3$ not being phenylethyl;
- $R_4$, $R_5$ and $R_6$ are, independently of each other, selected from the group consisting of hydrogen, optionally substituted $C_{1-10}$alkyl, OH, optionally substituted $C_{1-10}$ alkoxy, halo, optionally substituted aryloxy, optionally substituted ($C_{1-10}$alkyl)-S(O)$_n$— where n=0, 1 or 2, optionally substituted aryl-S(O)$_n$— where n=0, 1 or 2, or $R_4$ and $R_5$ together represent an optionally substituted saturated or unsaturated organic chain containing 1, 2, 3, 4, 5, 6 or 7 chain carbon atoms and optionally 1, 2 or 3 chain heteroatoms selected from O, N and S, provided that the chain is at least 3 atoms long;
- with the proviso that, when $R_1=R_2$=hydrogen, then any optionally substituted $C_{1-10}$alkyl or optionally substituted $C_{2-10}$alkenyl for $R_3$ must have a branch point at one or more of the α and β positions counted from the carbonyl group (or tautomeric form thereof) to which $R_3$ is attached;
- excluding 2-[4-[3-oxo-5-phenyl-2-(3,4,5-trimethoxybenzoyl)-pentyl]-phenoxy]-benzoic acid and its benzyl ester.

8. The composition according to claim 7, which is suitable and intended for use in the treatment of one or more conditions selected from the group consisting of hypersensitivity, smooth muscle disorders, spasmodic conditions, allergic conditions, inflammatory conditions and pain in a human or non-human patient, and the compound of formula I or a physiologically acceptable salt or complex thereof is present in an amount which is effective for that purpose when administered in an appropriate dosage to the patient.

9. The composition according to claim 7, wherein the compound of general formula I or a physiologically acceptable salt or complex thereof is present in association with one or more additional compound of general formula I or physiologically acceptable salt or complex thereof, or with one or more additional agents having activity against one or more conditions selected from the group consisting of hypersensitivity, smooth muscle disorders, spasmodic conditions, allergic conditions, inflammatory conditions, pain, and side effects of the compound of general formula I.

10. A method of manufacturing a composition as defined in claim 7, the method comprising bringing into admixture the said compound of formula I or physiologically acceptable salt or complex thereof and the physiologically acceptable carrier thereof.

11. The method according to claim 10, further comprising packaging the composition with instructions for use in the treatment of one or more conditions selected from the group consisting of hypersensitivity, smooth muscle disorders, spasmodic conditions, allergic conditions, inflammatory conditions and pain in a human or non-human patient, the said instructions including dosage information, information concerning the appropriate administration route and protocol, and safety information relevant to the said intended use.

12. A compound of general formula Ia:

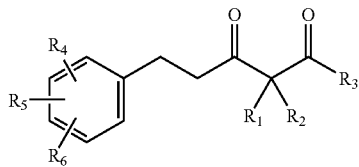

wherein:
$R_1$ and $R_2$ are, independently of each other, selected from the group consisting of hydrogen, optionally substituted $C_{1-10}$ alkyl, optionally substituted —CO—($C_{1-10}$ alkyl), optionally substituted $C_{3-10}$ cycloalkyl, optionally substituted —CO—($C_{3-10}$ cycloalkyl), optionally substituted $C_{2-10}$ alkenyl, optionally substituted —CO—($C_{2-10}$ alkenyl), optionally substituted aryl, and optionally substituted —CO-aryl, or $R_1$ and $R_2$ together represent an optionally substituted saturated or unsaturated $C_{1-10}$ alkylidene group, or an optionally substituted saturated or unsaturated $C_{3-10}$ cycloalkylidene group, or $R_1$ and $R_2$ together with the carbon atom to which they are attached represent an optionally substituted saturated or unsaturated organic ring containing 3, 4, 5, 6, 7 or 8 ring carbon atoms and optionally 1, 2 or 3 ring heteroatoms selected from O, N and S;

$R_3$ is selected from the group consisting of $C_{1-10}$ alkyl, optionally substituted $C_{3-10}$ cycloalkyl, $C_{2-10}$ alkenyl, optionally substituted aryl, substituted $C_{1-10}$alkyl, and substituted $C_{2-10}$ alkenyl, wherein in the said substituted alkyl and substituted alkenyl groups one or more substituents, which may be the same or different, are selected from: halo, $C_{1-6}$ alkyl, $C_{3-6}$ cycloalkyl, hydroxy, $C_{1-6}$ alkoxy, $C_{2-6}$ alkenyloxy, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{6-12}$ aryl, $C_{6-12}$ arylamino, di-$C_{6-12}$ arylamino, $C_{6-12}$ aroylamino, di-$C_{6-12}$ aroylamino, $C_{6-12}$ arylamido, carboxy, $C_{1-6}$ alkoxycarbonyl, ($C_{6-12}$ ar)($C_{1-10}$ alkoxy)carbonyl, carbamoyl, and any of the above in which a hydrocarbyl moiety is itself substituted by halo, hydroxy, amino, nitro, carbamoyl or carboxy, but $R_3$ not being phenylethyl;

$R_4$, $R_5$ and $R_6$ are, independently of each other, selected from the group consisting of hydrogen, optionally substituted $C_{1-10}$ alkyl, OH, optionally substituted $C_{1-10}$ alkoxy, halo, optionally substituted aryloxy, optionally substituted ($C_{1-10}$ alkyl)-S—(O)$_n$— where n=0, 1 or 2, optionally substituted aryl-S(O)$_n$— where n=0, 1 or 2, or $R_4$ and $R_5$ together represent an optionally substituted saturated or unsaturated organic chain containing 1, 2, 3, 4, 5, 6 or 7 chain carbon atoms and optionally 1, 2 or 3 chain heteroatoms selected from O, N and S, provided that the chain is at least 3 atoms long;

with the provisos that, when $R_1=R_2$=hydrogen, then:
(i) any optionally substituted $C_{1-10}$ alkyl or optionally substituted $C_{2-10}$ alkenyl for $R_3$ must have a branch point at one or more of the α and β positions counted from the carbonyl group (or tautomeric form thereof) to which $R_3$ is attached;
(ii) when additionally $R_3$ is un-substituted phenyl and $R_6$ is hydrogen, then (a) $R_4$ cannot be a group selected from 4-vinyl or 2-chloro when $R_5$=hydrogen, (b) $R_5$ cannot be 3-methoxy or 3-ethoxy when $R_4$ is 4-hydroxy; and (c) $R_4$ and $R_5$ cannot both be hydrogen; and
(iii) when additionally $R_4$ is 4-methoxy and $R_6$ is hydrogen, then (a) $R_3$ cannot be 2-hydroxy-3,6-dimethoxyphenyl when $R_5$ is 3-methoxy and (b) $R_3$ cannot be 2-hydroxyphenyl or 4-hydroxyphenyl when $R_5$ is hydrogen;
and with the further proviso that, when $R_2=R_5=R_6$=hydrogen, $R_3$ is methyl and $R_4$ is 4-methoxy, then $R_1$ cannot be —CO—CH═CH ($C_6H_4$)OMe in which —($C_6H_4$)OMe represents a 4-methoxyphenyl group;

or a physiologically acceptable salt or complex thereof;
but not including
2-[4-[3-oxo-5-phenyl-2-(3,4,5-trimethoxybenzoyl)-pentyl]-phenoxy]-benzoic acid benzyl ester;
2-[4-[3-oxo-5-phenyl-2-(3,4,5-trimethoxybenzoyl)-pentyl]-phenoxy]-benzoic acid;
1-(2-hydroxy-3-methoxyphenyl)-5-phenylpentane-1,3-dione;
1-(2-hydroxyphenyl)-5-phenylpentane-1,3-dione;
3-acetyl-4-(4-nitro-benzoyl)-7-phenyl-heptane-2,5-dione;
1,9-diphenyl-4-(3-phenylpropyl)-3,5-nonanedione;
1,5-diphenyl-2-benzyl-1,3-pentanedione;
7-methyl-4-(1-methyl-3-phenylpropyl)-1,9-diphenyl-3,5-nonanedione; and
1,7,9-triphenyl-4-(1,3-diphenylpropyl)-3,5-nonanedione.

13. The compound according to claim 12, wherein, independently of each other,
$R_1$ is selected from hydrogen and optionally substituted $C_{1-10}$ alkyl;
$R_2$ is selected from hydrogen and optionally substituted $C_{1-10}$ alkyl;
$R_3$ is selected from optionally substituted $C_{1-10}$ alkyl, optionally substituted $C_{3-10}$ cycloalkyl and optionally substituted aryl;
$R_4$ is hydroxyl or optionally substituted $C_{1-4}$ alkoxy;
$R_5$ is hydroxyl or optionally substituted $C_{1-4}$ alkoxy; and
$R_6$ is hydrogen.

14. The compound according to claim 12, wherein, independently of each other:
$R_1$ is selected from the group consisting of hydrogen, unsubstituted $C_{1-6}$ alkyl and phenyl-substituted $C_{1-6}$ alkyl;
$R_2$ is selected from the group consisting of hydrogen, unsubstituted $C_{1-6}$ alkyl and phenyl-substituted $C_{1-6}$ alkyl;
$R_3$ is selected from the group consisting of unsubstituted $C_{1-6}$ alkyl, ($C_{3-6}$ cycloalkyl)-substituted $C_{1-6}$ alkyl, unsubstituted $C_{3-6}$ cycloalkyl, unsubstituted phenyl, mono or poly phenyl-substituted phenyl, ($C_{1-6}$ alkyl)- substituted phenyl, ($C_{1-6}$ alkoxy)-substituted phenyl, mono or poly halo-substituted phenyl where polyhalo substituents may be the same or different, hydroxyl-substituted phenyl, ($C_{1-6}$ alkoxy)(hydroxyl)-disubstituted phenyl, ($C_{1-6}$ alkoxy) carbonyl-substituted phenyl and unsubstituted naphthyl;

$R_4$ is unsubstituted methoxy;

$R_5$ is hydroxyl; and $R_6$ is hydrogen.

15. The compound according to claim 12, being a compound selected from the group consisting of:

1-(4-Hydroxy-3-methoxyphenyl)-6-methyl-heptane-3,5-dione) (Compound 1);
6,6-Dimethyl-1-(4-hydroxy-3-methoxyphenyl)-heptane-3,5-dione (Compound 2);
7,7-Dimethyl-1-(4-hydroxy-3-methoxyphenyl)-octane-3,5-dione (Compound 3);
1-(4-Hydroxy-3-methoxyphenyl)-4,6,6-trimethyl-heptane-3,5-dione (Compound 4);
1-cyclopropyl-5-(4-hydroxy-3-methoxyphenyl)-pentane-1,3-dione (Compound 5);
5-(4-Hydroxy-3-methoxyphenyl)-1-(1-methylcyclopropyl)-pentane-1,3-dione (Compound 6);
5-(4-Hydroxy-3-methoxyphenyl)-2-methyl-1-(1-methylcyclopropyl)-pentane-1,3-dione (Compound 7);
1-Cyclopentyl-5-(4-hydroxy-3-methoxyphenyl)-pentane-1,3-dione (Compound 8);
1-(4-Hydroxy-3-methoxyphenyl)-6-methyloctane-3,5-dione (Compound 9);
5-(4-Hydroxy-3-methoxy-phenyl)-1-(1-methyl-cyclohexyl)-pentane-1,3-dione (Compound 10);
5-(4-Hydroxy-3-methoxy-phenyl)-2-methyl-1-phenyl-pentane-1,3-dione (Compound 11);
2-Ethyl-5-(4-hydroxy-3-methoxyphenyl)-1-phenyl-pentane-1,3-dione (Compound 12);
2-Benzyl-5-(4-hydroxy-3-methoxyphenyl)-1-phenylpentane-1,3-dione (Compound 13);
5-(4-Hydroxy-3-methoxyphenyl)-2-methyl-1-p-tolyl-pentane-1,3-dione (Compound 14);
1,5-Bis(4-hydroxy-3-methoxyphenyl)-pentane-1,3-dione (Compound 15);
1,5-Bis(4-hydroxy-3-methoxyphenyl)-2-methyl-pentane-1,3-dione (Compound 16);
5-(4-Hydroxy-3-methoxyphenyl)-1-(4-methoxyphenyl)-2-methyl-pentane-1,3-dione (Compound 17);
1-(Biphenyl-4-yl)-5-(4-hydroxy-3-methoxyphenyl)-pentane-1,3-dione (Compound 18);
1-(Biphenyl-2-yl)-5-(4-hydroxy-3-methoxyphenyl)-pentane-1,3-dione (Compound 19);
1-(4-Fluorophenyl)-5-(4-hydroxy-3-methoxyphenyl)-pentane-1,3-dione (Compound 20);
1-(4-Chlorophenyl)-5-(4-hydroxy-3-methoxyphenyl)pentane-1,3-dione (Compound 21);
1-(3-Chlorophenyl)-5-(4-hydroxy-3-methoxyphenyl)pentane-1,3-dione (Compound 22);
1-(3,4-Dihlorophenyl)-5-(4-hydroxy-3-methoxyphenyl)pentane-1,3-dione (Compound 23);
1-(2,4-Dihlorophenyl)-5-(4-hydroxy-3-methoxyphenyl)pentane-1,3-dione (Compound 24);
Methyl 4-(5-(4-hydroxy-3-methoxyphenyl)-3-oxopentanoyl)benzoate (Compound 25);
5-(4-Hydroxy-3-methoxyphenyl)-1-(naphthalene-2-yl)-pentane-1,3-dione (Compound 26);
5-(4-Hydroxy-3-methoxyphenyl)-1-(naphthalene-1-yl)-pentane-1,3-dione (Compound 27);
6-(4-Hydroxy-3-methoxyphenyl)-1-phenyl-hexane-2,4-dione (Compound 28);
6-(4-Hydroxy-3-methoxyphenyl)-1-naphthalen-1-yl-hexane-2,4-dione (Compound 29);
6-(4-Hydroxy-3-methoxyphenyl)-1,1-diphenyl-hexane-2,4-dione (Compound 30);
6-(4-Hydroxy-3-methoxyphenyl)-1,1-dimethyl-1-phenyl-hexane-2,4-dione (Compound 31);
2,2-Dimethyl-5-(4-hydroxy-3-methoxy-phenyl)-1-phenyl-pentane-1,3-dione (Compound 32);
5-(4-Hydroxy-3-methoxyphenyl)-2,2-dimethyl-1-(1-methylcyclopropyl)pentane-1,3-dione (Compound 70);
1-(4-Hydroxy-3-methoxyphenyl)-4,4,6,6-tetramethylheptane-3,5-dione (Compound 71);
1,5-bis(4-Hydroxy-3-methoxyphenyl)-2,2-dimethylpentane-1,3-dione (Compound 72);
1-(4-Fluorophenyl)-5-(4-hydroxy-3-methoxyphenyl)-2,2-dimethylpentane-1,3-dione (Compound 73);
1-(2-Chlorophenyl)-5-(4-hydroxy-3-methoxyphenyl)pentane-1,3-dione (Compound 74);
1-(4-chloro-3-methylphenyl)-5-(4-hydroxy-3-methoxyphenyl)pentane-1,3-dione (Compound 75);
1-(4-Chloro-2-methylphenyl)-5-(4-hydroxy-3-methoxyphenyl)pentane-1,3-dione (Compound 76);
1-(3-chloro-2-methylphenyl)-5-(4-hydroxy-3-methoxyphenyl)pentane-1,3-dione (Compound 77);
1-(3-chloro-4-methylphenyl)-5-(4-hydroxy-3-methoxyphenyl)pentane-1,3-dione (Compound 78);
5-(4-Hydroxy-3-methoxyphenyl)-2,2-dimethyl-1-(naphthalen-2-yl)pentane-1,3-dione (Compound 79);
5-(4-Hydroxy-3-methoxyphenyl)-1-p-tolylpentane-1,3-dione (Compound 80);
5-(4-Hydroxy-3-methoxyphenyl)-2,2-dimethyl-1-p-tolyl-pentane-1,3-dione (Compound 81);
1-(4-Cyanophenyl)-5-(4-hydroxy-3-methoxyphenyl)pentane-1,3-dione (Compound 82);
1-(4-tert-Butylphenyl)-5-(4-hydroxy-3-methoxyphenyl) pentane-1,3-dione (Compound 83);
5-(4-Hydroxy-3-methoxyphenyl)-1-o-tolylpentane-1,3-dione (Compound 84);
5-(4-Hydroxy-3-methoxyphenyl)-1-m-tolylpentane-1,3-dione (Compound 85);
5-(2-Chloro-4-hydroxy-5-methoxyphenyl)-1-(naphthalene-3-yl)pentane-1,3-dione (Compound 86);
5-(4-(2-aminoethoxy)-3-methoxyphenyl)-1-phenylpentane-1,3-dione hydrochloride (Compound 87); and
5-(4-(2-Aminoethoxy)-3-methoxyphenyl)-1-phenylpentane-1,3-dione hydrochloride (Compound 88).

16. A method for preparing a compound of general formula Ia as defined in claim 12 or a salt, complex thereof, which method comprises condensing a compound of general formula III with a compound of general formula IV:

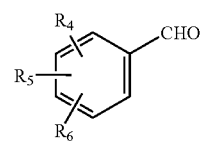

III

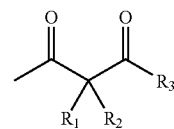

IV wherein $R_1$ to $R_6$ are as defined in the said preceding claim for general formula Ia, optionally in the presence of a chelating agent, to deactivate the carbon between the two carbonyl groups (or other tautomeric form) in formula IV in favour of the terminal methyl carbon atom, to obtain the compound of general formula I after reduction of the resulting double bond.

17. A method of preparing a compound of general formula Ia as defined in claim 12 or a salt, complex thereof, which method comprises selectively reducing the aliphatic carbon-carbon double bond marked * in a compound of general formula II:

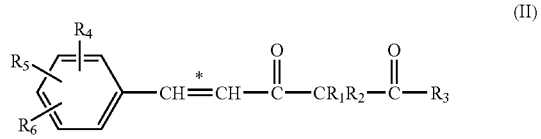

wherein $R_1$ to $R_6$ are as defined in the said preceding claim for general formula Ia, or a salt or complex thereof, to obtain the compound of general formula Ia.

18. The method according to claim 16, wherein the compound of general formula Ia is selected from the group consisting of:
- 1-(4-Hydroxy-3-methoxyphenyl)-6-methyl-heptane-3,5-dione) (Compound 1);
- 6,6-Dimethyl-1-(4-hydroxy-3-methoxyphenyl)-heptane-3,5-dione (Compound 2);
- 7,7-Dimethyl-1-(4-hydroxy-3-methoxyphenyl)-octane-3,5-dione (Compound 3);
- 1-(4-Hydroxy-3-methoxyphenyl)-4,6,6-trimethyl-heptane-3,5-dione (Compound 4);
- 1-cyclopropyl-5-(4-hydroxy-3-methoxyphenyl)-pentane-1,3-dione (Compound 5);
- 5-(4-Hydroxy-3-methoxyphenyl)-1-(1-methylcyclopropyl)-pentane-1,3-dione (Compound 6);
- 5-(4-Hydroxy-3-methoxyphenyl)-2-methyl-1-(1-methylcyclopropyl)-pentane-1,3-dione (Compound 7);
- 1-Cyclopentyl-5-(4-hydroxy-3-methoxyphenyl)-pentane-1,3-dione (Compound 8);
- 1-(4-Hydroxy-3-methoxyphenyl)-6-methyloctane-3,5-dione (Compound 9);
- 5-(4-Hydroxy-3-methoxy-phenyl)-1-(1-methyl-cyclohexyl)-pentane-1,3-dione (Compound 10);
- 5-(4-Hydroxy-3-methoxy-phenyl)-2-methyl-1-phenyl-pentane-1,3-dione (Compound 11);
- 2-Ethyl-5-(4-hydroxy-3-methoxyphenyl)-1-phenyl-pentane-1,3-dione (Compound 12);
- 2-Benzyl-5-(4-hydroxy-3-methoxyphenyl)-1-phenylpentane-1,3-dione (Compound 13);
- 5-(4-Hydroxy-3-methoxyphenyl)-2-methyl-1-p-tolyl-pentane-1,3-dione (Compound 14);
- 1,5-Bis(4-hydroxy-3-methoxyphenyl)-pentane-1,3-dione (Compound 15);
- 1,5-Bis(4-hydroxy-3-methoxyphenyl)-2-methyl-pentane-1,3-dione (Compound 16);
- 5-(4-Hydroxy-3-methoxyphenyl)-1-(4-methoxyphenyl)-2-methyl-pentane-1,3-dione (Compound 17);
- 1-(Biphenyl-4-yl)-5-(4-hydroxy-3-methoxyphenyl)-pentane-1,3-dione (Compound 18);
- 1-(Biphenyl-2-yl)-5-(4-hydroxy-3-methoxyphenyl)-pentane-1,3-dione (Compound 19);
- 1-(4-Fluorophenyl)-5-(4-hydroxy-3-methoxyphenyl)-pentane-1,3-dione (Compound 20);
- 1-(4-Chlorophenyl)-5-(4-hydroxy-3-methoxyphenyl)pentane-1,3-dione (Compound 21);
- 1-(3-Chlorophenyl)-5-(4-hydroxy-3-methoxyphenyl)pentane-1,3-dione (Compound 22);
- 1-(3,4-Dihlorophenyl)-5-(4-hydroxy-3-methoxyphenyl)pentane-1,3-dione (Compound 23);
- 1-(2,4-Dihlorophenyl)-5-(4-hydroxy-3-methoxyphenyl)pentane-1,3-dione (Compound 24);
- Methyl 4-(5-(4-hydroxy-3-methoxyphenyl)-3-oxopentanoyl)benzoate (Compound 25);
- 5-(4-Hydroxy-3-methoxyphenyl)-1-(naphthalene-2-yl)-pentane-1,3-dione (Compound 26);
- 5-(4-Hydroxy-3-methoxyphenyl)-1-(naphthalene-1-yl)-pentane-1,3-dione (Compound 27);
- 6-(4-Hydroxy-3-methoxyphenyl)-1-phenyl-hexane-2,4-dione (Compound 28);
- 6-(4-Hydroxy-3-methoxyphenyl)-1-naphthalen-1-yl-hexane-2,4-dione (Compound 29);
- 6-(4-Hydroxy-3-methoxyphenyl)-1,1-diphenyl-hexane-2,4-dione (Compound 30);
- 6-(4-Hydroxy-3-methoxyphenyl)-1,1-dimethyl-1-phenyl-hexane-2,4-dione (Compound 31);
- 2,2-Dimethyl-5-(4-hydroxy-3-methoxy-phenyl)-1-phenyl-pentane-1,3-dione (Compound 32);
- 5-(4-Hydroxy-3-methoxyphenyl)-1-phenyl-pentane-1,3-dione (Compound 69);
- 5-(4-Hydroxy-3-methoxyphenyl)-2,2-dimethyl-1-(1-methylcyclopropyl)pentane-1,3-dione (Compound 70);
- 1-(4-Hydroxy-3-methoxyphenyl)-4,4,6,6-tetramethylheptane-3,5-dione (Compound 71);
- 1,5-bis(4-Hydroxy-3-methoxyphenyl)-2,2-dimethylpentane-1,3-dione (Compound 72);
- 1-(4-Fluorophenyl)-5-(4-hydroxy-3-methoxyphenyl)-2,2-dimethylpentane-1,3-dione (Compound 73);
- 1-(2-Chlorophenyl)-5-(4-hydroxy-3-methoxyphenyl)pentane-1,3-dione (Compound 74);
- 1-(4-chloro-3-methylphenyl)-5-(4-hydroxy-3-methoxyphenyl)pentane-1,3-dione (Compound 75);
- 1-(4-Chloro-2-methylphenyl)-5-(4-hydroxy-3-methoxyphenyl)pentane-1,3-dione (Compound 76);
- 1-(3-chloro-2-methylphenyl)-5-(4-hydroxy-3-methoxyphenyl)pentane-1,3-dione (Compound 77);
- 1-(3-chloro-4-methylphenyl)-5-(4-hydroxy-3-methoxyphenyl)pentane-1,3-dione (Compound 78);
- 5-(4-Hydroxy-3-methoxyphenyl)-2,2-dimethyl-1-(naphthalen-2-yl)pentane-1,3-dione (Compound 79);
- 5-(4-Hydroxy-3-methoxyphenyl)-1-p-tolylpentane-1,3-dione (Compound 80);
- 5-(4-Hydroxy-3-methoxyphenyl)-2,2-dimethyl-1-p-tolyl-pentane-1,3-dione (Compound 81);
- 1-(4-Cyanophenyl)-5-(4-hydroxy-3-methoxyphenyl)pentane-1,3-dione (Compound 82);
- 1-(4-tert-Butylphenyl)-5-(4-hydroxy-3-methoxyphenyl)pentane-1,3-dione (Compound 83);
- 5-(4-Hydroxy-3-methoxyphenyl)-1-o-tolylpentane-1,3-dione (Compound 84);
- 5-(4-Hydroxy-3-methoxyphenyl)-1-m-tolylpentane-1,3-dione (Compound 85);
- 5-(2-Chloro-4-hydroxy-5-methoxyphenyl)-1-(naphthalene-3-yl)pentane-1,3-dione (Compound 86);
- 5-(4-(2-aminoethoxy)-3-methoxyphenyl)-1-phenylpentane-1,3-dione hydrochloride (Compound 87);
- 5-(4-(2-Aminoethoxy)-3-methoxyphenyl)-1-phenylpentane-1,3-dione hydrochloride (Compound 88);
- 5-(3-Ethoxy-4-hydroxyphenyl)-1-phenylpentane-1,3-dione (Compound 89); and salts and complexes thereof.

19. A compound of general formula IIa:

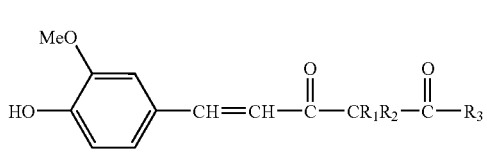

or a salt, complex or protected form thereof;
wherein:

$R_1$ and $R_2$ are, independently of each other, selected from the group consisting of hydrogen, optionally substituted $C_{1-10}$ alkyl, optionally substituted —CO—($C_{1-10}$ alkyl), optionally substituted $C_{3-10}$ cycloalkyl, optionally substituted —CO—($C_{3-10}$ cycloalkyl), optionally substituted $C_{2-10}$ alkenyl, optionally substituted —CO—($C_{2-10}$ alkenyl), optionally substituted aryl and optionally substituted —CO-aryl, or $R_1$ and $R_2$ together represent an optionally substituted saturated or unsaturated $C_{1-10}$ alkylidene group or an optionally substituted saturated or unsaturated organic ring containing 3, 4, 5, 6, 7 or 8 ring carbon atoms and optionally 1, 2 or 3 ring heteroatoms selected from O, N and S;

$R_3$ is selected from the group consisting of $C_{3-10}$ cycloalkyl, $C_{2-10}$ alkenyl, optionally substituted aryl, substituted $C_{1-10}$ alkyl, substituted $C_{3-10}$ cycloalkyl, and substituted $C_{2-10}$ alkenyl, wherein in the said substituted alkyl, substituted cycloalkyl, and substituted alkenyl groups one or more substituents, which may be the same or different, are selected from: halo, $C_{1-6}$ alkyl, $C_{3-6}$ cycloalkyl, hydroxy, $C_{1-6}$ alkoxy, $C_{2-6}$ alkenyloxy, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{6-12}$ aryl, $C_{6-12}$ arylamino, di-$C_{6-12}$ arylamino, $C_{6-12}$ aroylamino, di-$C_{6-12}$ aroylamino, $C_{6-12}$ arylamido, carboxy, $C_{1-6}$ alkoxycarbonyl, ($C_{6-12}$ ar)($C_{1-10}$ alkoxy)carbonyl, carbamoyl, and any of the above in which a hydrocarbyl moiety is itself substituted by halo, hydroxy, amino, nitro, carbamoyl or carboxy, but $R_3$ not being phenyl or substituted phenyl;

with the proviso that, when $R_1=R_2=$hydrogen, then any optionally substituted $C_{1-10}$ alkyl or optionally substituted $C_{2-10}$ alkenyl for $R_3$ must have a branch point at one or more of the α and β positions counted from the carbonyl group (or tautomeric form thereof) to which $R_3$ is attached;

20. The compound according to claim 19, being a compound selected from the group consisting of:

(E)-1-(4-Hydroxy-3-methoxyphenyl)-6-methyl-hept-1-ene-3,5-dione (Compound 33);
(E)-1-(4-Hydroxy-3-methoxyphenyl)-6,6-dimethyl-hept-1-ene-3,5-dione (Compound 34);
(E)-7,7-Dimethyl-1-(4-hydroxy-3-methoxyphenyl)-oct-1-ene-3,5-dione (Compound 35);
(E)-1-(4-Hydroxy-3-methoxyphenyl)-4,6,6-trimethyl-hept-1-ene-3,5-dione (Compound 36);
(E)-1-Cyclopropyl-5-(4-hydroxy-3-methoxyphenyl)-pent-4-ene-1,3-dione (Compound 37);
(E)-5-(4-Hydroxy-3-methoxyphenyl)-1-(1-methylcyclopropyl)-pent-4-ene-1,3-dione (Compound 38);
5-(4-Hydroxy-3-methoxyphenyl)-2-methyl-1-(1-methylcyclopropyl)pent-4-ene-1,3-dione (Compound 39);
(E)-1-Cyclopentyl-5-(4-hydroxy-3-methoxyphenyl)-pent-4-ene-1,3-dione (Compound 40);
(E)-1-(4-Hydroxy-3-methoxyphenyl)-6-methyl-oct-1-ene-3,5-dione (Compound 41);
(E)-5-(4-Hydroxy-3-methoxyphenyl)-1-(1-methylcyclohexyl)-pent-4-ene-1,3-dione (Compound 42);
(E)-5-(4-Hydroxy-3-methoxyphenyl)-2-methyl-1-phenyl-pent-4-ene-1,3-dione (Compound 43);
(E)-2-Ethyl-5-(4-hydroxy-3-methoxyphenyl)-1-phenyl-pent-4-ene-1,3-dione (Compound 44);
(E)-2-Benzyl-5-(4-hydroxy-3-methoxyphenyl)-1-phenyl-pent-4-ene-1,3-dione (Compound 45);
5-(4-Hydroxy-3-methoxyphenyl)-2-methyl-1-p-tolyl-pent-4-ene-1,3-dione (Compound 46);
(E)-1,5-Bis-(4-hydroxy-3-methoxyphenyl)-pent-4-ene-1,3-dione (Compound 47);
(E)-1,5-Bis(4-tert-butyldimethylsilyloxy-3-methoxyphenyl)-2-methylpent-4-ene-1,3-dione (Compound 48);
5-(4-Hydroxy-3-methoxyphenyl)-1-(4-methoxyphenyl)-2-methyl-pent-4-ene-1,3-dione (Compound 49);
(E)-1-(Biphenyl-4-yl)-5-(4-hydroxy-3-methoxyphenyl)-pent-4-ene-1,3-dione (Compound 50);
(E)-1-(Biphenyl-2-yl)-5-(4-hydroxy-3-methoxyphenyl)-pent-4-ene-1,3-dione (Compound 51);
(E)-1-(4-Fluorophenyl)-5-(4-hydroxy-3-methoxyphenyl)-pent-4-ene-1,3-dione (Compound 52);
1-(4-Chlorophenyl)-5-(4-hydroxy-3-methoxyphenyl)pent-4-ene-1,3-dione (Compound 53);
1-(3-Chlorophenyl)-5-(4-hydroxy-3-methoxyphenyl)pent-4-ene-1,3-dione (Compound 54);
1-(3,4-Dichlorophenyl)-5-(4-hydroxy-3-methoxyphenyl)pent-4-ene-1,3-dione (Compound 55);
1-(2,4-Dichlorophenyl)-5-(4-hydroxy-3-methoxyphenyl)pent-4-ene-1,3-dione (Compound 56);
Methyl 4-[(E)-1,3-dioxo-5-(4-hydroxy-3-methoxyphenyl)pent-4-enyl]benzoate (Compound 57);
(E)-5-(4-Hydroxy-3-methoxyphenyl)-1-(naphthalene-2-yl)-pent-4-ene-1,3-dione (Compound 58);
(E)-5-(4-Hydroxy-3-methoxyphenyl)-1-(naphthalene-1-yl)-pent-4-ene-1,3-dione (Compound 59);
(E)-6-(4-Hydroxy-3-methoxyphenyl)-1-phenyl-hex-5-ene-2,4-dione (Compound 60);
6-(4-Hydroxy-3-methoxyphenyl)-1-naphthalen-1-yl-hex-5-ene-2,4-dione (Compound 61);
6-(4-Hydroxy-3-methoxyphenyl)-1,1-diphenylhex-5-ene-2,4-dione (Compound 62);
6-(4-Hydroxy-3-methoxyphenyl)-1,1-dimethyl-1-phenyl-hex-5-ene-2,4-dione (Compound 63);
5-(4-Hydroxy-3-methoxyphenyl)-2,2-dimethyl-1-phenyl-pent-4-ene-1,3-dione (Compound 64);
(E)-5-(4-Hydroxy-3-methoxyphenyl)-1-p-tolyl-pent-4-ene-1,3-dione (Compound 65);
(E)-5-(4-Hydroxy-3-methoxyphenyl)-1-(4-methoxyphenyl)-pent-4-ene-1,3-dione (Compound 66);
(E)-5-(4-Hydroxy-3-methoxyphenyl)-1-(4-iodophenyl)-pent-4-ene-1,3-dione (Compound 67);
(E)-5-(4-hydroxy-3-methoxyphenyl)-2,2-dimethyl-1-(1-methyl-cyclopropyl)pent-4-ene-1,3-dione (Compound 90);
(E)-1-(4-Hydroxy-3-methoxyphenyl)-4,4,6,6-tetramethylhept-1-ene-3,5-dione (Compound 91);
(E)-1,5-bis(4-Hydroxy-3-methoxyphenyl)-2,2-dimethyl-pent-4-ene-1,3-dione (Compound 92);
(E)-1-(4-Fluorophenyl)-5-(4-hydroxy-3-methoxy-phenyl)-2,2-dimethyl-pent-4-ene-1,3-dione (Compound 93);
(E)-1-(2-Chlorophenyl)-5(4-hydroxy-3-methoxyphenyl)pent-4-ene-1,3-dione (Compound 94);

(E)-1-(4-Chloro-3-methylphenyl)-5-(4-hydroxy-3-methoxyphenyl)pent-4-ene-1,3-dione (Compound 95);

(E)-1-(4-Chloro-2-methylphenyl)-5-(4-hydroxy-3-methoxyphenyl)pent-4-ene-1,3-dione (Compound 96);

(E)-1-(3-Chloro-2-methylphenyl)-5-(4-hydroxy-3-methoxyphenyl)pent-4-ene-1,3-dione (Compound 97);

(E)-1-(3-Chloro-4-methylphenyl)-5-(4-hydroxy-3-methoxyphenyl)pent-4-ene-1,3-dione (Compound 98);

(E)-5-(4-Hydroxy-3-methoxyphenyl)-2,2-dimethyl-1-(naphthalene-3-yl)pent-4-ene-1,3-dione (Compound 99);

(E)-5-(4-Hydroxy-3-methoxyphenyl)-2,2-dimethyl-1-p-tolylpent-4-ene-1,3-dione (Compound 100);

(E)-1-(4-Cyanophenyl)-5-(4-hydroxy-3-methoxyphenyl)pent-4-ene-1,3-dione (Compound 101);

(E)-1-(4-tert-Butylphenyl)-5-(4-hydroxy-3-methoxyphenyl)pent-4-ene-1,3-dione (Compound 102);

(E)-5-(4-Hydroxy-3-methoxyphenyl)-1-o-tolylpent-4-ene-1,3-dione (Compound 103);

(E)-5-(4-Hydroxy-3-methoxyphenyl)-1-m-tolylpent-4-ene-1,3-dione (Compound 104); and salts, complexes and protected forms thereof.

21. A method for preparing a compound of general formula I or II

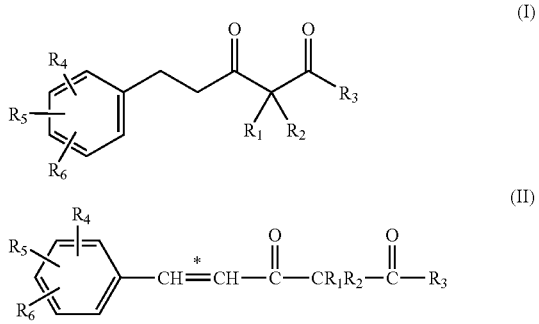

or a salt or complex thereof in which one or both of $R_1$ and $R_2$ is $C_{1-10}$alkyl and the other of $R_1$ and $R_2$, if not $C_{1-10}$alkyl, is a hydrogen atom, the method comprising alkylating the corresponding compound of general formula I or II or salt thereof in which both of $R_1$ and $R_2$ are hydrogen atoms by initially protecting any phenolic groups of the said compound using a base and a protecting group in the presence of a suitable solvent and subsequently reacting the treated compound with an alkylating agent, in the presence of a base, to obtain the alkylated compound, wherein $R_3$-$R_6$ are as defined in claim 1.

22. The method according to claim 21, wherein one of $R_1$ and $R_2$ is $C_{1-10}$alkyl and the other of $R_1$ and $R_2$ is a hydrogen atom.

23. The method according to claim 21, wherein sodium hydride and trimethylsilyl chloride in the presence of a suitable solvent are used for protecting the phenolic groups.

24. The method according to claim 21, wherein an alkyl iodide in the presence of potassium carbonate is used as the alkylating agent.

25. A method for preparing a compound of general formula I or II

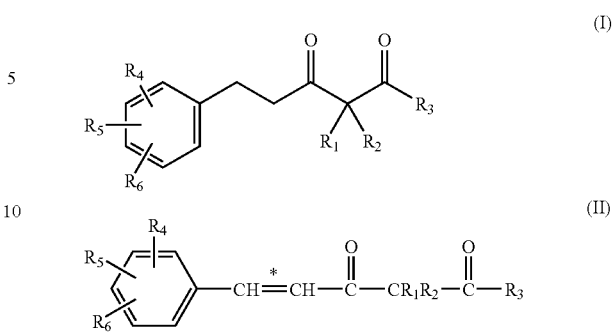

or a salt or complex thereof in which either $R_1$=$R_2$=H or one of $R_1$ and $R_2$ is $C_{1-10}$alkyl or $C_{2-10}$alkenyl (denoted by Alk) and the other of $R_1$ and $R_2$ is a hydrogen atom, the method comprising first preparing the imidazole derivative of a carboxylic acid having the formula HO.OCR$_3$, and then reacting the said imidazole derivative with a ketone having the formula V:

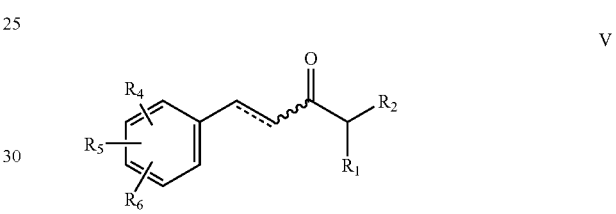

in the presence of base in a suitable solvent, to obtain the desired compound, wherein $R_3$-$R_6$ are as defined in claim 1.

26. A method for obtaining at least one, more preferably at least two, more preferably at least three, and most preferably all, of the following biological activities in human or other tissue in vitro or in vivo: modulation of TRPV1 receptor; modulation of smooth muscle tone; inhibition of tissue remodelling; and anti-inflammatory activity, the method comprising contacting the said tissue in vitro or in vivo with an effective amount of a compound of general formula I as defined in claim 1 or a physiologically acceptable salt or complex thereof.

27. A physiologically unacceptable salt or complex of a compound of general formula I as defined in claim 1.

28. A protected form of a compound of general formula Ia as defined in claim 12.

29. A physiologically unacceptable salt or complex of a compound of general formula Ia as defined in claim 12, or a protected form thereof.

30. A method of preparing a compound of general formula I or a physiologically acceptable salt or complex thereof, comprising subjecting a salt or complex as defined in claim 27 to conditions sufficient to form said compound of general formula I, said conditions comprising salt or ligand displacement.

31. A composition comprising a compound of formula Ia as defined in claim 12 or a physiologically acceptable salt or complex thereof and a physiologically acceptable carrier thereof.

32. The composition according to claim 31, being a foodstuff, food supplement, beverage, beverage supplement or other non-pharmaceutical composition, including, but not limited to, functional foodstuffs and beverages.

33. The composition according to claim 31, wherein the compound of general formula Ia or a physiologically acceptable salt or complex thereof is present in association with one or more additional compounds of general formula I or a physiologically acceptable salts or complexes thereof, or with one or more additional agents having activity against one or more conditions selected from the group consisting of hypersensitivity, smooth muscle disorders, spasmodic conditions, allergic conditions, inflammatory conditions, pain, and side effects of the compound of general formula I.

34. A method of manufacturing a composition as defined in claim 31, the method comprising bringing into admixture the said compound of formula Ia or a physiologically acceptable salt or complex thereof and the physiologically acceptable carrier thereof.

35. The method according to claim 2, wherein, independently of each other,
   $R_1$ is selected from the group consisting of hydrogen and optionally substituted $C_{1-10}$ alkyl;
   $R_2$ is selected from the group consisting of hydrogen and optionally substituted $C_{1-10}$ alkyl;
   $R_3$ is selected from the group consisting of $C_{1-10}$ alkyl, optionally substituted $C_{3-10}$ cycloalkyl, optionally substituted aryl, and $C_{1-10}$ alkyl substituted with one or more substituents, which may be the same or different, selected from: halo, $C_{1-6}$ alkyl, $C_{3-6}$ cycloalkyl, hydroxy, $C_{1-6}$ alkoxy, $C_{2-6}$ alkenyloxy, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{6-12}$ aryl, $C_{6-12}$ arylamino, di-$C_{6-12}$ arylamino, $C_{6-12}$ aroylamino, di-$C_{6-12}$ aroylamino, $C_{6-12}$ arylamido, carboxy, $C_{1-6}$ alkoxycarbonyl, $(C_{6-12}$ ar$)(C_{1-10}$ alkoxy)carbonyl, carbamoyl, and any of the above in which a hydrocarbyl moiety is itself substituted by halo, hydroxy, amino, nitro, carbamoyl or carboxy, but $R_3$ not being phenylethyl;
   $R_4$ is hydroxyl or optionally substituted $C_{1-4}$ alkoxy;
   $R_5$ is hydroxyl or optionally substituted $C_{1-4}$ alkoxy; and
   $R_6$ is hydrogen.

36. The method according to claim 2, wherein, independently of each other:
   $R_1$ is selected from the group consisting of hydrogen, unsubstituted $C_{1-6}$ alkyl and phenyl-substituted $C_{1-6}$ alkyl;
   $R_2$ is selected from the group consisting of hydrogen, unsubstituted $C_{1-6}$ alkyl and phenyl-substituted $C_{1-6}$ alkyl;
   $R_3$ is selected from the group consisting of unsubstituted $C_{1-6}$ alkyl, ($C_{3-6}$ cycloalkyl)-substituted $C_{1-6}$ alkyl, unsubstituted $C_{3-6}$ cycloalkyl, unsubstituted phenyl, mono or poly phenyl-substituted phenyl, ($C_{1-6}$ alkyl)-substituted phenyl, ($C_{1-6}$ alkoxy)-substituted phenyl, mono or poly halo-substituted phenyl where polyhalo substituents may be the same or different, hydroxyl-substituted phenyl, ($C_{1-6}$ alkoxy)(hydroxyl)-disubstituted phenyl, ($C_{1-6}$ alkoxy) carbonyl-substituted phenyl and unsubstituted naphthyl;
   $R_4$ is unsubstituted methoxy;
   $R_5$ is hydroxyl; and $R_6$ is hydrogen.

37. The method according to claim 2, wherein the compound is selected from the group consisting of:
   1-(4-Hydroxy-3-methoxyphenyl)-6-methyl-heptane-3,5-dione) (Compound 1);
   6,6-Dimethyl-1-(4-hydroxy-3-methoxyphenyl)-heptane-3,5-dione (Compound 2);
   7,7-Dimethyl-1-(4-hydroxy-3-methoxyphenyl)-octane-3,5-dione (Compound 3);
   1-(4-Hydroxy-3-methoxyphenyl)-4,6,6-trimethyl-heptane-3,5-dione (Compound 4);
   1-cyclopropyl-5-(4-hydroxy-3-methoxyphenyl)-pentane-1,3-dione (Compound 5);
   5-(4-Hydroxy-3-methoxyphenyl)-1-(1-methylcyclopropyl)-pentane-1,3-dione (Compound 6);
   5-(4-Hydroxy-3-methoxyphenyl)-2-methyl-1-(1-methylcyclopropyl)-pentane-1,3-dione (Compound 7);
   1-Cyclopentyl-5-(4-hydroxy-3-methoxyphenyl)-pentane-1,3-dione (Compound 8);
   1-(4-Hydroxy-3-methoxyphenyl)-6-methyloctane-3,5-dione (Compound 9);
   5-(4-Hydroxy-3-methoxy-phenyl)-1-(1-methyl-cyclohexyl)-pentane-1,3-dione (Compound 10);
   5-(4-Hydroxy-3-methoxy-phenyl)-2-methyl-1-phenyl-pentane-1,3-dione (Compound 11);
   2-Ethyl-5-(4-hydroxy-3-methoxyphenyl)-1-phenyl-pentane-1,3-dione (Compound 12);
   2-Benzyl-5-(4-hydroxy-3-methoxyphenyl)-1-phenylpentane-1,3-dione (Compound 13);
   5-(4-Hydroxy-3-methoxyphenyl)-2-methyl-1-p-tolyl-pentane-1,3-dione (Compound 14);
   1,5-Bis(4-hydroxy-3-methoxyphenyl)-pentane-1,3-dione (Compound 15);
   1,5-Bis(4-hydroxy-3-methoxyphenyl)-2-methyl-pentane-1,3-dione (Compound 16);
   5-(4-Hydroxy-3-methoxyphenyl)-1-(4-methoxyphenyl)-2-methyl-pentane-1,3-dione (Compound 17);
   1-(Biphenyl-4-yl)-5-(4-hydroxy-3-methoxyphenyl)-pentane-1,3-dione (Compound 18);
   1-(Biphenyl-2-yl)-5-(4-hydroxy-3-methoxyphenyl)-pentane-1,3-dione (Compound 19);
   1-(4-Fluorophenyl)-5-(4-hydroxy-3-methoxyphenyl)-pentane-1,3-dione (Compound 20);
   1-(4-Chlorophenyl)-5-(4-hydroxy-3-methoxyphenyl)pentane-1,3-dione (Compound 21);
   1-(3-Chlorophenyl)-5-(4-hydroxy-3-methoxyphenyl)pentane-1,3-dione (Compound 22);
   1-(3,4-Dihlorophenyl)-5-(4-hydroxy-3-methoxyphenyl)pentane-1,3-dione (Compound 23);
   1-(2,4-Dihlorophenyl)-5-(4-hydroxy-3-methoxyphenyl)pentane-1,3-dione (Compound 24);
   Methyl 4-(5-(4-hydroxy-3-methoxyphenyl)-3-oxopentanoyl)benzoate (Compound 25);
   5-(4-Hydroxy-3-methoxyphenyl)-1-(naphthalene-2-yl)-pentane-1,3-dione (Compound 26);
   5-(4-Hydroxy-3-methoxyphenyl)-1-(naphthalene-1-yl)-pentane-1,3-dione (Compound 27);
   6-(4-Hydroxy-3-methoxyphenyl)-1-phenyl-hexane-2,4-dione (Compound 28);
   6-(4-Hydroxy-3-methoxyphenyl)-1-naphthalen-1-yl-hexane-2,4-dione (Compound 29);
   6-(4-Hydroxy-3-methoxyphenyl)-1,1-diphenyl-hexane-2,4-dione (Compound 30);
   6-(4-Hydroxy-3-methoxyphenyl)-1,1-dimethyl-1-phenyl-hexane-2,4-dione (Compound 31);
   2,2-Dimethyl-5-(4-hydroxy-3-methoxy-phenyl)-1-phenyl-pentane-1,3-dione (Compound 32);
   5-(4-Hydroxy-3-methoxyphenyl)-1-phenyl-pentane-1,3-dione (Compound 69);
   5-(4-Hydroxy-3-methoxyphenyl)-2,2-dimethyl-1-(1-methylcyclopropyl)pentane-1,3-dione (Compound 70);
   1-(4-Hydroxy-3-methoxyphenyl)-4,4,6,6-tetramethylheptane-3,5-dione (Compound 71);
   1,5-bis(4-Hydroxy-3-methoxyphenyl)-2,2-dimethylpentane-1,3-dione (Compound 72);

1-(4-Fluorophenyl)-5-(4-hydroxy-3-methoxyphenyl)-2,2-dimethylpentane-1,3-dione (Compound 73);

1-(2-Chlorophenyl)-5-(4-hydroxy-3-methoxyphenyl)pentane-1,3-dione (Compound 74);

1-(4-chloro-3-methylphenyl)-5-(4-hydroxy-3-methoxyphenyl)pentane-1,3-dione (Compound 75);

1-(4-Chloro-2-methylphenyl)-5-(4-hydroxy-3-methoxyphenyl)pentane-1,3-dione (Compound 76);

1-(3-chloro-2-methylphenyl)-5-(4-hydroxy-3-methoxyphenyl)pentane-1,3-dione (Compound 77);

1-(3-chloro-4-methylphenyl)-5-(4-hydroxy-3-methoxyphenyl)pentane-1,3-dione (Compound 78);

5-(4-Hydroxy-3-methoxyphenyl)-2,2-dimethyl-1-(naphthalen-2-yl)pentane-1,3-dione (Compound 79);

5-(4-Hydroxy-3-methoxyphenyl)-1-p-tolylpentane-1,3-dione (Compound 80);

5-(4-Hydroxy-3-methoxyphenyl)-2,2-dimethyl-1-p-tolylpentane-1,3-dione (Compound 81);

1-(4-Cyanophenyl)-5-(4-hydroxy-3-methoxyphenyl)pentane-1,3-dione (Compound 82);

1-(4-tert-Butylphenyl)-5-(4-hydroxy-3-methoxyphenyl)pentane-1,3-dione (Compound 83);

5-(4-Hydroxy-3-methoxyphenyl)-1-o-tolylpentane-1,3-dione (Compound 84);

5-(4-Hydroxy-3-methoxyphenyl)-1-m-tolylpentane-1,3-dione (Compound 85);

5-(2-Chloro-4-hydroxy-5-methoxyphenyl)-1-(naphthalene-3-yl)pentane-1,3-dione (Compound 86);

5-(4-(2-aminoethoxy)-3-methoxyphenyl)-1-phenylpentane-1,3-dione hydrochloride (Compound 87);

5-(4-(2-Aminoethoxy)-3-methoxyphenyl)-1-phenylpentane-1,3-dione hydrochloride (Compound 88); and 5-(3-Ethoxy-4-hydroxyphenyl)-1-phenylpentane-1,3-dione (Compound 89).

\* \* \* \* \*